United States Patent
Maloveste et al.

(10) Patent No.: US 11,155,832 B2
(45) Date of Patent: Oct. 26, 2021

(54) ADENOVECTORS FOR DELIVERY OF THERAPEUTIC GENETIC MATERIAL INTO T CELLS

(71) Applicant: GenVec, Inc., Gaithersburg, MD (US)

(72) Inventors: Sebastien M. Maloveste, Rockville, MD (US); Damodar Ettyreddy, Clarksburg, MD (US); Douglas E. Brough, Gaithersburg, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 16/338,075

(22) PCT Filed: Sep. 29, 2017

(86) PCT No.: PCT/US2017/054397
§ 371 (c)(1),
(2) Date: Mar. 29, 2019

(87) PCT Pub. No.: WO2018/064523
PCT Pub. Date: Apr. 5, 2018

(65) Prior Publication Data
US 2019/0233845 A1    Aug. 1, 2019

Related U.S. Application Data

(60) Provisional application No. 62/402,755, filed on Sep. 30, 2016.

(51) Int. Cl.
*C12N 15/00* (2006.01)
*A61K 39/23* (2006.01)
*C12N 15/86* (2006.01)
*C07K 14/005* (2006.01)

(52) U.S. Cl.
CPC ............ *C12N 15/86* (2013.01); *C07K 14/005* (2013.01); *C12N 2710/10322* (2013.01); *C12N 2710/10343* (2013.01)

(58) Field of Classification Search
None
See application file for complete search history.

(56) References Cited

U.S. PATENT DOCUMENTS

2014/0147463 A1*  5/2014  Radosevic ............... C12N 7/00
424/192.1

FOREIGN PATENT DOCUMENTS

| WO | WO 02/24933 A2 | 3/2002 |
| WO | WO 2013/126712 A1 | 8/2013 |
| WO | WO 2013/181128 A1 | 12/2013 |
| WO | WO 2014/153270 A1 | 9/2014 |

OTHER PUBLICATIONS

Kahl et al., "Potent immune responses and in vitro pro-inflammatory cytokine suppression by a novel adenovirus vaccine vector based on rare human serotype 28," Vaccine, 28:5691-5702 (Year: 2010).*

(Continued)

*Primary Examiner* — M Franco G Salvoza
(74) *Attorney, Agent, or Firm* — Leydig, Voit & Mayer, Ltd.

(57) ABSTRACT

The invention provides adenoviral vectors and compositions for the highly efficient transduction of T cells.

33 Claims, 9 Drawing Sheets

Specification includes a Sequence Listing.

| AdGFP vector | Day 1 | Day 2 | Day5 | Day 7 | Day 13 | Day 19 |
|---|---|---|---|---|---|---|
| Adef | ++ | ++ | ++ | ++ | ++ | + |
| Adf.F(F2KpK7) | + | ++ | ++ | ++ | ++ | 0 |
| Adef.F(RGD) | + | ++ | ++ | ++ | ++ | + |
| Ad28ef | ++ | ++ | ++ | ++ | ++ | + |
| Ad28ef.F(26SK) | +++ | +++ | +++ | +++ | +++ | ++ |
| Ad28ef.H(45)F(45S.45K) | +++ | +++ | +++ | +++ | +++ | ++ |
| Ad28ef.F(Hl4CRGD) | +++ | +++ | +++ | +++ | +++ | + |
| Ad28ef.F(5S) | + | ++ | ++ | ++ | ++ | + |
| Ad35ef | +++ | +++ | ++ | ++ | ++ | + |
| Ad35f.F(sK[C7]-HIRGD) | 0 | 0 | 0 | 0 | 0 | 0 |
| Ad35f.F(s25k-RGD) | 0 | 0 | 0 | 0 | 0 | 0 |
| Ad35f.F(s25k) | 0 | 0 | 0 | 0 | 0 | 0 |
| SAV38ef | + | + | 0 | 0 | 0 | 0 |
| Ad41ef | + | + | + | + | 0 | 0 |
| GC44ef | ++ | ++ | ++ | ++ | ++ | + |
| GC45ef | ++ | ++ | ++ | ++ | ++ | + |
| Ad14ef | +++ | ++++ | +++ | +++ | ++ | + |
| Mock (Uninfected) | 0 | 0 | 0 | 0 | 0 | 0 |

(56) References Cited

OTHER PUBLICATIONS

Kahl et al., "Potent immune responses and in vitro pro-inflammatory cytokine suppression by a novel adenovirus vaccine vector based on rare human serotype 28," *Vaccine*, 28: 5691-5702 (2010).

Sengupta et al., "Enhanced Transduction and Replication of RDG-Fiber Modified Adenovirus in Primary T Cells," *PLoS One*, 6(3): e18091 (2011).

Ueyama et al., "Ocular Localization and Transduction by Adenoviral Vectors Are Serotype-Dependent and Can Be Modified by Inclusion of RGD Fiber Modification," *PLoS One*, 9(9): e108071 (2014).

Wu et al., "Double Modification of Adenovirus Fiber with RGD and Polylysine Motifs Improves Coxsackieviurs-Adenovirus Recepter-Independent Gene Transfer Efficiency," *Human Gene Therapy*, 13:1647-1653 (2002).

Ye et al., "Engineered CD8+ cytotoxic T cells with fiber-modified adenovirus-mediated TNF-α gene transfection counteract immunosuppressive interleukin-10-secreting lung metastasis and solid tumors," *Cancer Gene Therapy*, 14: 661-675 (2007).

Zhang et al., "Chimeric adenoviral vector Ad5F35L containing the Ad5 natural long-shaft exhibits efficient gene transfer into human T lymphocytes," Journal of Virological Methods, 194: 52-29 (2013).

European Patent Office, International Search Report and Written Opinion in International Patent Application No. PCT/US2017/054397 (dated Mar. 20, 2018).

\* cited by examiner

Figure 1

| AdGFP vector | Day 1 | Day 2 | Day5 | Day 7 | Day 13 | Day 19 |
|---|---|---|---|---|---|---|
| Adef | ++ | ++ | ++ | ++ | ++ | + |
| Adf.F(F2KpK7) | + | ++ | ++ | ++ | ++ | 0 |
| Adef.F(RGD) | + | ++ | ++ | ++ | ++ | + |
| Ad28ef | ++ | ++ | ++ | ++ | ++ | + |
| Ad28ef.F(26SK) | +++ | +++ | +++ | +++ | +++ | ++ |
| Ad28ef.H(45)F(45S.45K) | +++ | +++ | +++ | +++ | +++ | ++ |
| Ad28ef.F(HI4CRGD) | +++ | +++ | +++ | +++ | +++ | + |
| Ad28ef.F(5S) | + | ++ | ++ | ++ | ++ | + |
| Ad35ef | +++ | +++ | ++ | ++ | ++ | + |
| Ad35f.F(sK[C7]-HIRGD) | 0 | 0 | 0 | 0 | 0 | 0 |
| Ad35f.F(s25k-RGD) | 0 | 0 | 0 | 0 | 0 | 0 |
| Ad35f.F(s25k) | 0 | 0 | 0 | 0 | 0 | 0 |
| SAV38ef | + | + | 0 | 0 | 0 | 0 |
| Ad41ef | + | + | + | + | 0 | 0 |
| GC44ef | ++ | ++ | ++ | ++ | ++ | + |
| GC45ef | ++ | ++ | ++ | ++ | ++ | + |
| Ad14ef | +++ | ++++ | +++ | +++ | ++ | + |
| Mock (Uninfected) | 0 | 0 | 0 | 0 | 0 | 0 |

Figure 2

| AdGFP vector | GFP (%) |
|---|---|
| Cells only | 0 |
| Adef | 21.4 |
| Ad28ef.F(26SK) | 65.1 |
| Ad28ef.H(45)F(45SK) | 56.9 |
| Ad28ef.F(HI4CRGD) | 41.9 |
| GC44ef | 15.8 |
| GC45ef | 18.0 |
| Ad14ef | 19 |
| Ad35ef | 42.5 |
| GC46ef | 13.3 |

Figure 3

|  | MOI | PU/mL | Total Cell Density | Viable Cell Density | % Viable |
|---|---|---|---|---|---|
| Cells only | NA | NA | 2.80E+06 | 2.7E+06 | 96.1 |
| AdGFP vector | | | | | |
| Adempty | 40,000 | 1.00E+12 | 2.80E+06 | 2.6E+06 | 95.2 |
| Adempty | 4000 | 1.00E+12 | 2.90E+06 | 2.8E+06 | 96.6 |
| Adef | 40,000 | 6.40E+11 | 2.50E+06 | 2.3E+06 | 89.9 |
| Adef | 4000 | 6.40E+11 | 2.60E+06 | 2.4E+06 | 92.7 |
| Ad28ef.H(45)F(45SK) | 40,000 | 5.03E+11 | 1.80E+06 | 1.7E+06 | 92.8 |
| Ad28ef.H(45)F(45SK) | 4000 | 5.03E+11 | 2.70E+06 | 2.5E+06 | 93.9 |
| Ad14ef | 400,000 | 1.34E+12 | 1.70E+06 | 1.5E+06 | 83.9 |
| Ad14ef | 40,000 | 1.34E+12 | 2.20E+06 | 1.9E+06 | 89.3 |
| Ad14ef | 4000 | 1.34E+12 | 2.20E+06 | 2.0E+06 | 92.1 |
| Ad28ef | 4000 | 4.13E+10 | 2.30E+06 | 2.2E+06 | 90.3 |
| Ad28ef.F(26SK) | 4000 | 4.90E+11 | 3.10E+06 | 2.7E+06 | 89.3 |
| Ad28ef.F(HI4CRGD) | 4000 | 2.06E+11 | 2.70E+06 | 2.5E+06 | 92 |
| | | | | | |
| AdLuciferase vector | | | | | |
| Ad14L | 400,000 | 1.45E+12 | 1.50E+06 | 1.5E+06 | 95.5 |
| Ad14L | 40,000 | 1.45E+12 | 2.00E+06 | 1.9E+06 | 95 |
| Ad14L | 4000 | 1.45E+12 | 2.40E+06 | 2.4E+06 | 96.7 |

Figure 4

| AdLuciferase vector | MOI | Relative Luciferase Units |
|---|---|---|
| AdL | 40,000 | 398018 |
| | 40,000 | 254559 |
| | 4000 | 175929 |
| | 4000 | 122359 |
| AdL.F35 | 40,000 | 323111 |
| | 40,000 | 287160 |
| | 4000 | 94200 |
| | 4000 | 57344 |
| Ad28L | 40,000 | 100842 |
| | 40,000 | 83028 |
| | 4000 | 33774 |
| | 4000 | 34849 |
| Ad14L | 400,000 | 57481 |
| | 400,000 | 58034 |
| | 40,000 | 85959 |
| | 40,000 | 81050 |
| | 4000 | 72035 |
| | 4000 | 73024 |
| Cells only | NA | 67 |

Figure 5

| AdGFP vector | MOI | GFP (%) |
|---|---|---|
| Cells only | NA | 0.069 |
| Adempty | 40,000 | 0.058 |
| Adempty | 4000 | 0.053 |
| Adef | 40,000 | 26.6 |
| Adef | 40,000 | 25.3 |
| Adef | 4000 | 16.2 |
| Adef | 4000 | 15.8 |
| Ad28ef.H(45)F(45SK) | 40,000 | 33.1 |
| Ad28ef.H(45)F(45SK) | 40,000 | 31.7 |
| Ad28ef.H(45)F(45SK) | 4000 | 18.3 |
| Ad28ef.H(45)F(45SK) | 4000 | 18.3 |
| Ad14ef | 400,000 | 14.4 |
| Ad14ef | 400,000 | 13.1 |
| Ad14ef | 40,000 | 12.2 |
| Ad14ef | 40,000 | 11.8 |
| Ad14ef | 4000 | 11.1 |
| Ad14ef | 4000 | 11.2 |
| Ad28ef | 4000 | 15.9 |
| Ad28ef | 4000 | 17.5 |
| Ad28ef.F(26SK) | 4000 | 18 |
| Ad28ef.F(26SK) | 4000 | 18.4 |
| Ad28ef.F(HI4CRGD) | 4000 | 13.5 |
| Ad28ef.F(HI4CRGD) | 4000 | 14.8 |

Figure 6

| AdGFP vector | MOI | % GFP | Total Cell Density | %Viability |
|---|---|---|---|---|
| Cells only | NA | 0 | 2.40E+06 | 93 |
| Adempty | 40,000 | 0 | 2.20E+06 | 94 |
| Adempty | 40,000 | 0 | 2.10E+06 | 95 |
| Adempty | 20,000 | 0 | 2.40E+06 | 94 |
| Adempty | 20,000 | 0 | 2.60E+06 | 95 |
| Adempty | 10,000 | 0 | 2.50E+06 | 96 |
| Adempty | 10,000 | 0 | 2.50E+06 | 96 |
| Adempty | 5000 | 0 | 2.50E+06 | 95 |
| Adempty | 5000 | 0 | 2.40E+06 | 96 |
| Adef | 40,000 | 47 | 2.40E+06 | 97 |
| Adef | 40,000 | 46 | 2.50E+06 | 96 |
| Adef | 20,000 | 44 | 2.20E+06 | 96 |
| Adef | 20,000 | 44 | 2.20E+06 | 95 |
| Adef | 10,000 | 42 | 2.50E+06 | 96 |
| Adef | 10,000 | 39 | 2.30E+06 | 95 |
| Adef | 5000 | 36 | 2.20E+06 | 95 |
| Adef | 5000 | 36 | 2.10E+06 | 97 |
| Ad28ef.H(45)F(45SK) | 40,000 | 95 | 9.70E+05 | 89 |
| Ad28ef.H(45)F(45SK) | 40,000 | 97 | 1.40E+06 | 86 |
| Ad28ef.H(45)F(45SK) | 20,000 | 93 | 1.80E+06 | 85 |
| Ad28ef.H(45)F(45SK) | 20,000 | 93 | 1.50E+06 | 89 |
| Ad28ef.H(45)F(45SK) | 10,000 | 86 | 1.80E+06 | 95 |
| Ad28ef.H(45)F(45SK) | 10,000 | 87 | 1.80E+06 | 94 |
| Ad28ef.H(45)F(45SK) | 5000 | 76 | 2.10E+06 | 96 |
| Ad28ef.H(45)F(45SK) | 5000 | 77 | 2.10E+06 | 94 |

SEQUENCE LISTING

```
<160> NUMBER OF SEQ ID NOS: 28

<210> SEQ ID NO 1
<211> LENGTH: 531
<212> TYPE: PRT
<213> ORGANISM: Artificial Sequence
<220> FEATURE:
<223> OTHER INFORMATION: Synthetic

<400> SEQUENCE: 1

Arg Ser Gln Arg Leu Thr Leu Arg Phe Val Pro Val Asp Arg Glu Asp
1               5                   10                  15

Thr Thr Tyr Ser Tyr Lys Ala Arg Phe Thr Leu Ala Val Gly Asp Asn
            20                  25                  30

Arg Val Leu Asp Met Ala Ser Thr Tyr Phe Asp Ile Arg Gly Val Leu
        35                  40                  45

Asp Arg Gly Pro Ser Phe Lys Pro Tyr Ser Gly Thr Ala Tyr Asn Ser
    50                  55                  60

Leu Ala Pro Lys Ser Ala Pro Asn Pro Ser Gln Trp Asp Ala Lys Glu
65                  70                  75                  80
```

```
Lys Glu Gly Val Ala Gln Thr Glu Lys Asn Val Leu Lys Thr Phe Gly
                85                  90                  95

Val Ala Ala Thr Gly Gly Phe Asn Ile Thr Asp Gln Gly Leu Leu Leu
            100                 105                 110

Gly Thr Glu Glu Thr Ala Glu Asn Val Lys Lys Asp Ile Tyr Ala Glu
        115                 120                 125

Lys Thr Phe Gln Pro Glu Pro Gln Val Gly Glu Asn Trp Gln Glu
    130                 135                 140

Ser Glu Ala Phe Tyr Gly Gly Arg Ala Ile Lys Lys Asp Thr Lys Met
145                 150                 155                 160

Lys Pro Cys Tyr Gly Ser Phe Ala Arg Pro Thr Asn Glu Lys Gly Gly
                165                 170                 175

Gln Ala Lys Phe Lys Thr Leu Asp Gly Gln Val Thr Lys Asp Pro Asp
            180                 185                 190

Ile Asp Phe Ala Tyr Phe Asp Val Pro Gly Gly Lys Ala Pro Thr Gly
                195                 200                 205

Ser Ser Leu Pro Glu Glu Tyr Lys Ala Asp Ile Ile Leu Tyr Thr Glu
        210                 215                 220

Asn Val Asn Leu Glu Thr Pro Asp Thr His Ile Val Tyr Lys Pro Gly
225                 230                 235                 240

Lys Glu Asp Asp Asn Ser Glu Ile Asn Leu Thr Gln Gln Ser Met Pro
                245                 250                 255

Asn Arg Pro Asn Tyr Ile Gly Phe Arg Asp Asn Phe Val Gly Leu Met
                260                 265                 270

Tyr Tyr Asn Ser Thr Gly Asn Met Gly Val Leu Ala Gly Gln Ala Ser
            275                 280                 285

Gln Leu Asn Ala Val Asp Leu Gln Asp Arg Asn Thr Glu Leu Ser
    290                 295                 300

Tyr Gln Leu Leu Leu Asp Ser Leu Gly Asp Arg Thr Arg Tyr Phe Ser
305                 310                 315                 320

Met Trp Asn Ser Ala Val Asp Ser Tyr Asp Pro Asp Val Arg Ile Ile
                325                 330                 335

Glu Asn His Gly Val Glu Asp Glu Leu Pro Asn Tyr Cys Phe Pro Leu
            340                 345                 350

Asn Gly Thr Gly Thr Asn Ser Thr Tyr Gln Gly Val Lys Ile Thr Gly
        355                 360                 365

Asn Asn Asp Gly Asp Leu Glu Thr Glu Trp Glu Arg Asp Glu Ala Ile
370                 375                 380

Ser Arg Gln Asn Gln Ile Cys Lys Gly Asn Val Tyr Ala Met Glu Ile
385                 390                 395                 400

Asn Leu Gln Ala Asn Leu Trp Lys Ser Phe Leu Tyr Ser Asn Val Ala
                405                 410                 415

Leu Tyr Leu Pro Asp Ser Tyr Lys Tyr Thr Pro Ala Asn Val Thr Leu
                420                 425                 430

Pro Ala Asn Thr Asn Thr Tyr Glu Tyr Met Asn Gly Arg Val Val Ala
            435                 440                 445

Pro Ser Leu Val Asp Ala Tyr Ile Asn Ile Gly Ala Arg Trp Ser Leu
450                 455                 460

Asp Pro Met Asp Asn Val Asn Pro Phe Asn His His Arg Asn Ala Gly
465                 470                 475                 480

Leu Arg Tyr Arg Ser Met Leu Leu Gly Asn Gly Arg Tyr Val Pro Phe
                485                 490                 495
```

His Ile Gln Val Pro Gln Lys Phe Phe Ala Ile Lys Asn Leu Leu Leu
            500                 505                 510

Leu Pro Gly Ser Tyr Thr Tyr Glu Trp Asn Phe Arg Lys Asp Val Asn
    515                 520                 525

Met Ile Leu
    530

<210> SEQ ID NO 2
<211> LENGTH: 1596
<212> TYPE: DNA
<213> ORGANISM: Artificial Sequence
<220> FEATURE:
<223> OTHER INFORMATION: Synthetic

<400> SEQUENCE: 2

```
ccggtcccag cgtctgacgc tgcgcttcgt gcccgtggat cgcgaggaca ccacgtactc      60
gtacaaggcg cgcttcactc tggccgtggg agacaaccgg gtgctagaca tggccagcac     120
ttactttgac atccgcggcg tcctggaccg cggtcccagc ttcaaaccct actcgggcac     180
ggcttacaac agcctggccc ccaagagcgc tcccaatccc agccagtggg atgcaaagga     240
aaaggaagga gttgcccaaa cagaaaaaaa tgttttaaaa acatttggtg ttgccgctac     300
aggtggtttt aatattacag atcagggttt gttacttgga actgaggaaa cagctgaaaa     360
cgttaaaaag gatatctatg cagagaaaac tttccagcct gaacctcaag ttggtgaaga     420
aaactggcag gaaagtgaag cctttttatgg aggaagggct attaagaaag acaccaaaat     480
gaagccatgc tatggttcat tgccagacc cactaatgaa aaggaggac aggctaaatt     540
taaaacacta gatgggcaag ttacaaagaa tccagatatt gactttgctt actttgacgt     600
ccctggcgga aaagctccaa caggcagtag tctaccggaa gaatacaaag cagatataat     660
tttgtacaca gaaaatgtta atctggaaac accagatact cacatagtgt ataaacctgg     720
caaagaagat gacaattctg aaattaactt aacacaacag tccatgccaa acagacccaa     780
ctacattggc tttagggaca acttgtagg tctcatgtac tacaacagta ctggcaacat     840
gggtgtgctg gctggtcagg cctctcagtt gaatgctgtg gtggacttgc aagacagaaa     900
caccgagctg tcttaccagc tcttgctaga ttctctgggt gacagaacca gatactttag     960
catgtggaac tctgcggttg acagttatga tcccgatgtc aggatcattg agaatcacgg    1020
tgtggaagat gaacttccaa actattgctt cccattgaat ggcactggta ccaattccac    1080
ctatcaaggt gtaaaaatta caggtaataa tgatggcgat cttgaaaccg aatgggaaag    1140
agatgaagca atctctagac aaaaccaaat ctgcaagggc aacgtctatg ccatggagat    1200
caacctccag gccaacctgt ggaagagttt tctgtactcg aacgtagccc tgtacctgcc    1260
tgactcatac aagtacacgc cggccaacgt cacgctgccc gccaacacca acacctacga    1320
gtacatgaac ggccgcgtgg tagcccccctc gctggtggac gcttacatca catcggcgc    1380
ccgctggtcg ctggatccca tggacaatgt aaacccattc aaccaccacc gcaacgcggg    1440
cctgcgctac cgttccatgt tgttgggcaa cggtcgctac gtgcccttcc acatccaagt    1500
gccccaaaag ttctttgcca tcaagaacct gcttctgctc ccgggctcct acacctacga    1560
gtggaacttc cgcaaggacg tcaacatgat cctgca                              1596
```

<210> SEQ ID NO 3
<211> LENGTH: 324
<212> TYPE: PRT
<213> ORGANISM: Artificial Sequence
<220> FEATURE:

<223> OTHER INFORMATION: Synthetic

<400> SEQUENCE: 3

Leu Ser Leu Lys Leu Ala Asp Pro Ile Ala Ile Val Asn Gly Asp Val
1               5                   10                  15

Ser Leu Lys Val Gly Gly Gly Leu Thr Leu Gln Glu Gly Asn Leu Thr
            20                  25                  30

Val Asp Ala Lys Ala Pro Leu Gln Val Ala Asn Asp Asn Lys Leu Glu
        35                  40                  45

Leu Ser Tyr Ala Asp Pro Phe Glu Val Lys Asp Thr Lys Leu Gln Leu
    50                  55                  60

Lys Val Gly His Gly Leu Lys Val Ile Asp Glu Lys Thr Ser Ser Gly
65                  70                  75                  80

Leu Gln Ser Leu Ile Gly Asn Leu Val Val Leu Thr Gly Lys Gly Ile
                85                  90                  95

Gly Thr Gln Glu Leu Lys Asp Lys Asp Glu Thr Lys Asn Ile Gly
            100                 105                 110

Val Gly Ile Asn Val Arg Ile Gly Lys Asn Glu Ser Leu Ala Phe Asp
            115                 120                 125

Lys Asp Gly Asn Leu Val Ala Trp Asp Asn Glu Asn Asp Arg Arg Thr
130                 135                 140

Leu Trp Thr Thr Pro Asp Thr Ser Pro Asn Cys Lys Ile Ser Thr Glu
145                 150                 155                 160

Lys Asp Ser Lys Leu Thr Leu Val Leu Thr Lys Cys Gly Ser Gln Ile
                165                 170                 175

Leu Ala Ser Val Ser Leu Leu Ala Val Ala Gly Ser Tyr Leu Asn Met
            180                 185                 190

Thr Ala Ser Thr Gln Lys Ser Ile Lys Val Ser Leu Met Phe Asp Ser
        195                 200                 205

Lys Gly Leu Leu Met Thr Thr Ser Ser Ile Asp Lys Gly Tyr Trp Asn
    210                 215                 220

Tyr Arg Asn Lys Asn Ser Val Val Gly Thr Ala Tyr Glu Asn Ala Ile
225                 230                 235                 240

Pro Phe Met Pro Asn Leu Val Ala Tyr Pro Arg Pro Asn Thr Pro Asp
                245                 250                 255

Ser Lys Ile Tyr Ala Arg Ser Lys Ile Val Gly Asn Val Tyr Leu Ala
            260                 265                 270

Gly Leu Ala Tyr Gln Pro Ile Val Ile Thr Val Ser Phe Asn Gln Glu
        275                 280                 285

Lys Asp Ala Ser Cys Ala Tyr Ser Ile Thr Phe Glu Phe Ala Trp Asn
    290                 295                 300

Lys Asp Tyr Val Gly Gln Phe Asp Thr Thr Ser Phe Thr Phe Ser Tyr
305                 310                 315                 320

Ile Ala Gln Glu

<210> SEQ ID NO 4
<211> LENGTH: 975
<212> TYPE: DNA
<213> ORGANISM: Artificial Sequence
<220> FEATURE:
<223> OTHER INFORMATION: Synthetic

<400> SEQUENCE: 4
ttgtcactca aactggctga cccaatagcc atcgtcaatg gggatgtctc actcaaggtg      60
ggaggtggac tcactttgca agaaggaaac ctaactgttg atgcaaaggc tccattgcaa     120

```
gttgcaaatg acaacaaatt ggagctttct tatgcagacc catttgaggt taaagacact      180
aagctacaat taaaagtagg tcatggttta aaagtaatag atgaaaaaac ttcttcaggt      240
cttcaaagtc taattggaaa tctcgtagtt ttaacaggaa aaggaattgg cactcaagaa      300
ttaaaagaca agacgatga aactaaaaat ataggagttg aataaatgt gagaataggg        360 aaaaacgaaa gtctggcgtt tgacaaagat ggaaatttgg tagcatggga taatgaaaac     420
gacaggcgca ctctatggac aactccagac acatctccaa attgtaaaat aagtactgaa     480
aaagactcca aacttacttt agtccttact aaatgcggat ctcaaattct agcaagtgtg     540
tctttgcttg ctgtcgctgg aagttatctt aatatgacag ctagtactca aaagagtata     600
aaggtatctt tgatgtttga ctcaaaaggg cttctaatga ctacatcttc tattgataaa     660
ggatattgga attatagaaa taaaaacagc gttgttggaa ctgcttatga aaacgcaatt     720
ccatttatgc caaatttagt ggcttatcca agacctaaca cgccagactc taaaatttat     780
gctagaagca aaattgttgg aaatgtttat ttagcaggtt tggcttacca accaattgtc     840
ataacagtta gttttaatca ggagaaggat gcaagttgtg cttactcaat aacatttgaa     900
tttgcctgga caaagacta cgttggtcaa tttgatacca cctcctttac cttctcttat      960
attgcccaag aatga                                                       975
```

```
<210> SEQ ID NO 5
<211> LENGTH: 134
<212> TYPE: PRT
<213> ORGANISM: Artificial Sequence
<220> FEATURE:
<223> OTHER INFORMATION: Synthetic

<400> SEQUENCE: 5

Met Asn Gly Thr Gly Gly Pro Phe Glu Gly Gly Leu Phe Ser Pro Tyr
1               5                   10                  15

Leu Thr Thr Arg Leu Pro Gly Trp Ala Gly Val Arg Gln Asn Val Met
            20                  25                  30

Gly Ser Thr Val Asp Gly Arg Pro Val Leu Pro Ala Asn Ser Ser Thr
        35                  40                  45

Met Thr Tyr Ala Thr Val Gly Ser Ser Ser Leu Asp Ser Thr Ala Ala
    50                  55                  60

Ala Ala Ala Ala Ala Ala Ala Met Thr Ala Thr Arg Leu Ala Ser Ser
65                  70                  75                  80

Tyr Met Pro Ser Ser Gly Ser Ser Pro Ser Val Pro Ser Ser Ile Ile
                85                  90                  95

Ala Glu Glu Lys Leu Leu Ala Leu Leu Ala Glu Leu Glu Ala Leu Ser
            100                 105                 110

Arg Gln Leu Ala Ala Leu Thr Gln Gln Val Ser Glu Leu Arg Glu Gln
        115                 120                 125

Gln Gln Gln Gln Asn Lys
    130

<210> SEQ ID NO 6
<211> LENGTH: 519
<212> TYPE: PRT
<213> ORGANISM: Artificial Sequence
<220> FEATURE:
<223> OTHER INFORMATION: Synthetic

<400> SEQUENCE: 6

Met Arg Arg Ala Val Val Ser Ser Ser Pro Pro Pro Ser Tyr Glu Ser
```

-continued

```
1               5                   10                  15
Val Met Ala Gln Ala Thr Leu Glu Val Pro Phe Val Pro Arg Tyr
                20                  25                  30
Met Ala Pro Thr Glu Gly Arg Asn Ser Ile Arg Tyr Ser Glu Leu Ala
                35                  40                  45
Pro Gln Tyr Asp Thr Thr Arg Val Tyr Leu Val Asp Asn Lys Ser Ala
    50                  55                  60
Asp Ile Ala Ser Leu Asn Tyr Gln Asn Asp His Ser Asn Phe Leu Thr
65                  70                  75                  80
Thr Val Val Gln Asn Asn Asp Phe Thr Pro Ala Glu Ala Ser Thr Gln
                85                  90                  95
Thr Ile Asn Phe Asp Glu Arg Ser Arg Trp Gly Gly Asp Leu Lys Thr
                100                 105                 110
Ile Leu His Thr Asn Met Pro Asn Val Asn Glu Tyr Met Phe Thr Ser
                115                 120                 125
Lys Phe Lys Ala Arg Val Met Val Ala Arg Lys His Pro Lys Asp Val
            130                 135                 140
Asp Ala Ser Asp Leu Ser Lys Asp Ile Leu Glu Tyr Asp Trp Phe Glu
145                 150                 155                 160
Phe Thr Leu Pro Glu Gly Asn Phe Ser Glu Thr Met Thr Ile Asp Leu
                165                 170                 175
Met Asn Asn Ala Ile Leu Glu Asn Tyr Leu Gln Val Gly Arg Gln Asn
            180                 185                 190
Gly Val Leu Glu Ser Asp Ile Gly Val Lys Phe Asp Ser Arg Asn Phe
        195                 200                 205
Lys Leu Gly Trp Asp Pro Val Thr Lys Leu Val Met Pro Gly Val Tyr
    210                 215                 220
Thr Tyr Glu Ala Phe His Pro Asp Val Val Leu Pro Gly Cys Gly
225                 230                 235                 240
Val Asp Phe Thr Glu Ser Arg Leu Ser Asn Leu Leu Gly Ile Arg Lys
                245                 250                 255
Lys Gln Pro Phe Gln Glu Gly Phe Arg Ile Met Tyr Glu Asp Leu Val
                260                 265                 270
Gly Gly Asn Ile Pro Ala Leu Leu Asn Val Lys Glu Tyr Leu Lys Asp
            275                 280                 285
Lys Glu Glu Ala Gly Thr Ala Asp Ala Asn Thr Ile Lys Ala Gln Asn
    290                 295                 300
Asp Ala Val Pro Arg Gly Asp Asn Tyr Ala Ser Ala Glu Ala Lys
305                 310                 315                 320
Ala Ala Gly Lys Glu Ile Glu Leu Lys Ala Ile Leu Lys Asp Asp Ser
                325                 330                 335
Asn Arg Ser Tyr Asn Val Ile Glu Gly Thr Thr Asp Thr Leu Tyr Arg
            340                 345                 350
Ser Trp Tyr Leu Ser Tyr Thr Tyr Gly Asp Pro Glu Lys Gly Val Gln
        355                 360                 365
Ser Trp Thr Leu Leu Thr Thr Pro Asp Val Thr Cys Gly Ala Glu Gln
    370                 375                 380
Val Tyr Trp Ser Leu Pro Asp Leu Met Gln Asp Pro Val Thr Phe Arg
385                 390                 395                 400
Ser Thr Gln Gln Val Ser Asn Tyr Pro Val Val Gly Ala Glu Leu Met
                405                 410                 415
Pro Phe Arg Ala Lys Ser Phe Tyr Asn Asp Leu Ala Val Tyr Ser Gln
            420                 425                 430
```

```
Leu Ile Arg Ser Tyr Thr Ser Leu Thr His Val Phe Asn Arg Phe Pro
        435                 440                 445

Asp Asn Gln Ile Leu Cys Arg Pro Pro Ala Pro Thr Ile Thr Thr Val
450                 455                 460

Ser Glu Asn Val Pro Ala Leu Thr Asp His Gly Thr Leu Pro Leu Arg
465                 470                 475                 480

Ser Ser Ile Arg Gly Val Gln Arg Val Thr Val Thr Asp Ala Arg Arg
                485                 490                 495

Arg Thr Cys Pro Tyr Val Tyr Lys Ala Leu Gly Ile Val Ala Pro Arg
            500                 505                 510

Val Leu Ser Ser Arg Thr Phe
        515

<210> SEQ ID NO 7
<211> LENGTH: 732
<212> TYPE: PRT
<213> ORGANISM: Artificial Sequence
<220> FEATURE:
<223> OTHER INFORMATION: Synthetic

<400> SEQUENCE: 7

Met Glu Glu Gln Pro Arg Lys Gln Glu Gln Glu Asp Leu Thr Thr
1               5                   10                  15

His Glu Gln Pro Lys Ile Glu Gln Asp Leu Gly Phe Glu Glu Pro Ala
                20                  25                  30

Arg Leu Glu Pro Pro Gln Asp Glu Gln Glu His Glu Gln Asp Ala Gly
            35                  40                  45

Gln Glu Glu Thr Asp Ala Gly Leu Glu His Gly Tyr Leu Gly Gly Glu
        50                  55                  60

Glu Asp Val Leu Leu Lys His Leu Gln Arg Gln Ser Leu Ile Leu Arg
65                  70                  75                  80

Asp Ala Leu Ala Asp Arg Ser Glu Thr Pro Leu Ser Val Glu Glu Leu
                85                  90                  95

Cys Arg Ala Tyr Glu Leu Asn Leu Phe Ser Pro Arg Val Pro Pro Lys
            100                 105                 110

Arg Gln Pro Asn Gly Thr Cys Glu Pro Asn Pro Arg Leu Asn Phe Tyr
        115                 120                 125

Pro Val Phe Ala Val Pro Glu Ala Leu Ala Thr Tyr His Ile Phe Phe
    130                 135                 140

Lys Asn Gln Lys Ile Pro Val Ser Cys Arg Ala Asn Arg Thr Arg Ala
145                 150                 155                 160

Asp Ala Leu Leu Ala Leu Gly Pro Gly Ala His Ile Pro Asp Ile Ala
                165                 170                 175

Ser Leu Glu Glu Val Pro Lys Ile Phe Glu Gly Leu Gly Arg Asp Glu
            180                 185                 190

Thr Arg Ala Ala Asn Ala Leu Lys Glu Thr Ala Glu Glu Gly His
        195                 200                 205

Thr Ser Ala Leu Val Glu Leu Glu Gly Asp Asn Ala Arg Leu Ala Val
    210                 215                 220

Leu Lys Arg Ser Val Glu Leu Thr His Phe Ala Tyr Pro Ala Val Asn
225                 230                 235                 240

Leu Pro Pro Lys Val Met Arg Arg Ile Met Asp Gln Leu Ile Met Pro
                245                 250                 255

His Ile Glu Ala Leu Asp Glu Ser Gln Glu Gln Arg Pro Glu Asp Val
            260                 265                 270
```

```
Arg Pro Val Val Ser Asp Glu Met Leu Ala Arg Trp Leu Gly Thr Arg
        275                 280                 285

Asp Pro Gln Ala Leu Glu Gln Arg Arg Lys Leu Met Leu Ala Val Val
    290                 295                 300

Leu Val Thr Leu Glu Leu Glu Cys Met Arg Arg Phe Phe Ser Asp Pro
305                 310                 315                 320

Glu Thr Leu Arg Lys Val Glu Thr Leu His Tyr Thr Phe Arg His
                325                 330                 335

Gly Phe Val Arg Gln Ala Cys Lys Ile Ser Asn Val Glu Leu Thr Asn
                340                 345                 350

Leu Val Ser Cys Leu Gly Ile Leu His Glu Asn Arg Leu Gly Gln Thr
            355                 360                 365

Val Leu His Ser Thr Leu Lys Gly Glu Ala Arg Arg Asp Tyr Val Arg
        370                 375                 380

Asp Cys Ile Phe Leu Phe Leu Cys His Thr Trp Gln Ala Ala Met Gly
385                 390                 395                 400

Val Trp Gln Gln Cys Leu Glu Asp Glu Asn Leu Lys Glu Leu Asp Lys
                405                 410                 415

Val Leu Ala Arg Asn Leu Lys Lys Leu Trp Thr Gly Phe Asp Glu Arg
            420                 425                 430

Thr Val Ala Ser Asp Leu Ala Gln Ile Val Phe Pro Glu Arg Leu Arg
        435                 440                 445

Gln Thr Leu Lys Gly Gly Leu Pro Asp Phe Met Ser Gln Ser Met Ile
    450                 455                 460

Gln Asn Tyr Arg Thr Phe Ile Leu Glu Arg Ser Gly Met Leu Pro Ala
465                 470                 475                 480

Thr Cys Asn Ala Phe Pro Ser Asp Phe Val Pro Leu Ser Tyr Arg Glu
                485                 490                 495

Cys Pro Pro Pro Leu Trp Ser His Cys Tyr Leu Leu Gln Leu Ala Asn
            500                 505                 510

Tyr Ile Ala Tyr His Ser Asp Val Ile Glu Asp Val Ser Gly Glu Gly
        515                 520                 525

Leu Leu Glu Cys His Cys Arg Cys Asn Leu Cys Ser Pro His Arg Ser
530                 535                 540

Leu Val Cys Asn Pro Gln Leu Leu Ser Glu Thr Gln Val Ile Gly Thr
545                 550                 555                 560

Phe Glu Leu Gln Gly Pro Gln Glu Ser Thr Ala Pro Leu Lys Leu Thr
                565                 570                 575

Pro Gly Leu Trp Thr Ser Ala Tyr Leu Arg Lys Phe Val Pro Glu Asp
            580                 585                 590

Tyr His Ala His Glu Ile Lys Phe Phe Glu Asp Gln Ser Arg Pro Gln
        595                 600                 605

His Ala Asp Leu Thr Ala Cys Val Ile Thr Gln Gly Ala Ile Leu Ala
    610                 615                 620

Gln Leu His Ala Ile Gln Lys Ser Arg Gln Glu Phe Leu Leu Lys Lys
625                 630                 635                 640

Gly Arg Gly Val Tyr Leu Asp Pro Gln Thr Gly Glu Val Leu Asn Pro
                645                 650                 655

Gly Leu Pro Gln His Ala Glu Glu Ala Gly Ala Ala Ser Gly Gly
            660                 665                 670

Asp Gly Arg Arg Met Gly Gln Pro Gly Arg Gly Arg Met Gly Gly
        675                 680                 685
```

-continued

```
Gly Asp Arg Gly Gly Arg Ile Gly Arg Gly Arg Gly Ala Gly Asn
    690             695             700

Arg Ala Ala Arg Arg Thr Ile Arg Ala Gly Ser Pro Gly Gly His
705             710             715             720

Gly Tyr Asn Leu Arg Ser Ser Gly Gln Ala Ser Ser
            725             730

<210> SEQ ID NO 8
<211> LENGTH: 373
<212> TYPE: PRT
<213> ORGANISM: Artificial Sequence
<220> FEATURE:
<223> OTHER INFORMATION: Synthetic

<400> SEQUENCE: 8

Met His Pro Val Leu Arg Gln Met Arg Pro Thr Pro Ala Thr Thr
1               5               10              15

Ala Thr Ala Ala Val Ala Gly Ala Gly Ala Val Ala Pro Pro Gln Thr
            20              25              30

Glu Met Asp Leu Glu Glu Gly Glu Gly Leu Ala Arg Leu Gly Ala Pro
        35              40              45

Ser Pro Glu Arg His Pro Arg Val Gln Leu Gln Lys Asp Val Arg Pro
50              55              60

Ala Tyr Val Pro Pro Gln Asn Leu Phe Arg Asp Arg Ser Gly Glu Glu
65              70              75              80

Pro Glu Glu Met Arg Asp Cys Arg Phe Arg Ala Gly Arg Glu Leu Arg
                85              90              95

Glu Gly Leu Asp Arg Gln Arg Val Leu Arg Asp Glu Asp Phe Glu Pro
            100             105             110

Asn Glu Gln Thr Gly Ile Ser Pro Ala Arg Ala His Val Ala Ala Ala
        115             120             125

Asn Leu Val Thr Ala Tyr Glu Gln Thr Val Lys Gln Glu Arg Asn Phe
130             135             140

Gln Lys Ser Phe Asn Asn His Val Arg Thr Leu Ile Ala Arg Glu Glu
145             150             155             160

Val Ala Leu Gly Leu Met His Leu Trp Asp Leu Ala Glu Ala Ile Val
                165             170             175

Gln Asn Pro Asp Ser Lys Pro Leu Thr Ala Gln Leu Phe Leu Val Val
            180             185             190

Gln His Ser Arg Asp Asn Glu Ala Phe Arg Glu Ala Leu Leu Asn Ile
        195             200             205

Ala Glu Pro Glu Gly Arg Trp Leu Leu Glu Leu Ile Asn Ile Leu Gln
210             215             220

Ser Ile Val Val Gln Glu Arg Ser Leu Ser Leu Ala Glu Lys Val Ala
225             230             235             240

Ala Ile Asn Tyr Ser Val Leu Ser Leu Gly Lys Phe Tyr Ala Arg Lys
                245             250             255

Ile Tyr Lys Thr Pro Tyr Val Pro Ile Asp Lys Glu Val Lys Ile Asp
            260             265             270

Ser Phe Tyr Met Arg Met Ala Leu Lys Val Leu Thr Leu Ser Asp Asp
        275             280             285

Leu Gly Val Tyr Arg Asn Asp Arg Ile His Lys Ala Val Ser Thr Ser
    290             295             300

Arg Arg Arg Glu Leu Ser Asp Arg Glu Leu Met Leu Ser Leu Arg Arg
305             310             315             320
```

Ala Leu Val Gly Gly Ala Ala Gly Gly Glu Glu Ser Tyr Phe Asp Met
            325                 330                 335

Gly Ala Asp Leu His Trp Gln Pro Ser Arg Arg Ala Leu Glu Ala Ala
        340                 345                 350

Tyr Gly Pro Glu Asp Leu Glu Glu Asp Glu Glu Glu Glu Glu Asp Ala
    355                 360                 365

Pro Ala Ala Gly Tyr
    370

<210> SEQ ID NO 9
<211> LENGTH: 3531
<212> TYPE: DNA
<213> ORGANISM: Artificial Sequence
<220> FEATURE:
<223> OTHER INFORMATION: Synthetic

<400> SEQUENCE: 9

| | | | | | |
|---|---|---|---|---|---|
| atggccttgg | ttcaaagtca | cggggccagt | ggtcttcacg | cagaggcggc | agatccagga | 60 |
| tgtcaaccga | cgcgtcgtcg | cgcacgccag | cgctctcagg | gcgcagcacc | gggacctgcc | 120 |
| cgagcgccac | gccgacgtgc | tctgccgcc | cctgcccgcg | gggccggaac | cgccgctgcc | 180 |
| gccgggagcg | cgtccgcgac | accgcttcta | aaagcgcacc | gcggcacggt | cgtggccccg | 240 |
| cgcagctacg | ggctcatgca | atgcgtggac | acggccacca | actcacccgt | agaaatcaag | 300 |
| taccatctgc | atctcaagca | cgccctcacc | cgcctctacg | aggtcaacct | cagaaccctg | 360 |
| cccccggacc | tggatctccg | cgacaccatg | gacagctccc | aactgcgcgc | cctcgtcttc | 420 |
| gctctccgcc | cccgccgcgc | cgagatctgg | acctggctcc | cgcgcgggct | cgtcagcctc | 480 |
| tccgtcctcg | aggagcccca | gggtgagtcc | cacgcaggcg | aacatgaaaa | ccaccagcca | 540 |
| gggccgccac | tcctgaagtt | cctcctcaag | gacgcgctg | tgtatctcgt | ggatgaggta | 600 |
| cagcccgtgc | agcgctgcga | gtactgcgga | cgcttttaca | gcatcagca | cgagtgctcg | 660 |
| gttcgccggc | gggatttcta | ctttcatcac | atcaacagcc | actcgtccaa | ctggtggcag | 720 |
| gaaatccagt | tcttcccaat | cggctctcat | cctcgcacgg | agaggctctt | tgtcacctac | 780 |
| gatgtagaaa | cctacacctg | gatggggtcc | ttcggcaagc | agctcgtccc | cttcatgctg | 840 |
| gtcatgaaat | tctccgggga | ccccgagctg | atcgccctgg | ctcgcgatct | cgccgtgcgc | 900 |
| ttacgctggg | atcgctggga | gcgggacccc | ctcaccttct | actgcgtcac | accagaaaag | 960 |
| atggccgtgg | gccagcagtt | ccgcctctt | cgcgacgagc | tccagaccct | catggcccgc | 1020 |
| gagctctggg | cttccttcat | gcaagccaac | ccacatctcc | aggagtgggc | gctcgagcag | 1080 |
| cacggcctgc | aatgccccga | ggacctcacc | tacgaggagc | tcaaaaagct | gccgcacatc | 1140 |
| aaaggccgcc | cgcgattcat | ggaactctac | atcgtcgggc | acaacatcaa | cggcttcgac | 1200 |
| gagatcgtcc | tcgccgccca | ggtgatcaac | aaccgagcct | ccgtcccggg | ccctttccgc | 1260 |
| atcacccgca | atttcatgcc | gcgggcaggc | aagattctct | tcaatgacgt | cactttcgct | 1320 |
| ctgcctaacc | ccctctcgaa | gaagcgcacc | gatttcgagc | tctgggagca | cggcggctgc | 1380 |
| gacgactcgg | acttcaagta | ccagttcttg | aaagtcatgg | tcagggacac | cttcgccctg | 1440 |
| acgcacacct | cgctccgcaa | ggccgctcaa | gcttacgccc | tccccgtgga | aagggctgc | 1500 |
| tgtccctaca | aggccgtgaa | ccatttctac | atgctgggct | cttaccgtgc | ggacgatcga | 1560 |
| ggattcccgc | tccgggagta | ctggaaggat | gacgaggagt | acgccctcaa | ccgcgagctg | 1620 |
| tgggagaaga | aggagaagc | gggttatgac | atcatccgcg | aaacgctgga | ctactgcgcc | 1680 |
| atggacgtcc | tcgtcaccgc | cgagctcgtc | gccaagctgc | aagactccta | cgcgcacttc | 1740 |

| | | | | |
|---|---|---|---|---|
| atccgcgact | cggtccgcct | gccccacgcc | cactttaaca | tcttccaacg gccaccatc | 1800 |
| tcctccaact | cgcacgccat | ctttcgccag | atcgtcttcc | gcgccgagca gcccagcgc | 1860 |
| accaatctcg | gcccctcctt | cttggcccc | tcgcacgagt | tgtatgacta cgtgcgcgcc | 1920 |
| agcatccgcg | gggggcgctg | ttatcccacc | tacatcggca | tcctctcgga gcccatctat | 1980 |
| gtctatgaca | tctgcggcat | gtacgcctcc | gccctcacgc | atcccatgcc ctggggtccg | 2040 |
| cccctcaacc | cctacgagcg | agcgctggcc | gcccgcgagt | ggcagatggc cttggatgat | 2100 |
| gcatcctcaa | aaatcgatta | ttttgacaag | gaactctgtc | cgggcatctt caccatcgat | 2160 |
| gcggaccccc | ctgacgagca | cctcctggat | gtgctgcccc | cgttctgctc gcgcaagggt | 2220 |
| ggcagactct | gctggaccaa | cgagcccctg | cgcggcgagg | tggccaccag cgtggacctg | 2280 |
| gtcaccctgc | ataaccgcgg | ctggcgcgtc | aggatcgtgc | ccgacgagcg caccaccgtc | 2340 |
| ttccccgaat | ggaagtgcgt | cgcgcgcgag | tatgtccagc | tcaacatcgc ggccaaggag | 2400 |
| cgcgccgacc | gtgacaaaaa | tcagaccatg | agatccatcg | ccaagcttct ctccaacgcc | 2460 |
| ctctatggct | cctttgccac | caagcttgac | aataaaaaaa | tagtcttttc tgaccagatg | 2520 |
| gatgaaagtc | tcctaaaaag | catcgcggca | gggcaagcca | acatcaaatc ctcctcgttt | 2580 |
| ctagaaactg | acaacctgag | tgccgaggtc | atgcccgctc | tcgagaggga atacctaccc | 2640 |
| caacagctgg | cgctcgtgga | cagcgacgcg | aagagagtg | aggacgagca cagacccgcc | 2700 |
| cccttttata | ccccccgtc | ggggacccc | ggtcacgtgg | cctacaccta caagccaatc | 2760 |
| accttcttgg | atgcggagga | gggggacatg | tgcttgcaca | cggtggaaaa ggtggacccc | 2820 |
| ctggtggaca | acgaccgcta | cccctcgcac | gtggcctcct | ttgtcttggc gtggacgcgc | 2880 |
| gccttcgtct | cagagtggtc | cgaatttctc | tacgaggagg | accgcgggac gcccctgcag | 2940 |
| gacaggccaa | tcaagtccat | ctacggggac | accgacagcc | tgtttgtcac cgagcgcgga | 3000 |
| cacagactca | tggagacgcg | aggtaagaag | cgcatcaaaa | agaacggggg aaaactggtt | 3060 |
| tttgaccccg | aacaacccga | gctcacctgg | ctcgtcgagt | gcgagaccgt ctgcgcccac | 3120 |
| tgcggagcgg | acgcgttcgc | ccccgagtcc | gtctttctcg | cacccaagct atacgccctg | 3180 |
| caatccctcc | tctgtcccgc | ctgtgggcgc | tcttccaagg | gcaagctccg cgccaagggc | 3240 |
| cacgccgccg | aggccctcaa | ctacgagctc | atggtcaact | gctatctcgc cgacgcgcag | 3300 |
| ggcgaagacc | gtgcccgttt | cagcaccagc | aggatgagtc | tcaagcgaac ccttgcaagc | 3360 |
| gcccagcccg | ggcccaccc | cttcaccgtg | acggagacaa | ccctcacgcg gaccctgaga | 3420 |
| ccctggaagg | acatgacgct | ggccgcgctg | gacgcccatc | gtctcgtgcc ctacagtcgc | 3480 |
| agtcgtccca | accccgaaa | cgaggaagtc | tgctggatcg | agatgccgta g | 3531 |

<210> SEQ ID NO 10
<211> LENGTH: 28607
<212> TYPE: DNA
<213> ORGANISM: Artificial Sequence
<220> FEATURE:
<223> OTHER INFORMATION: Synthetic

<400> SEQUENCE: 10

| | | | | |
|---|---|---|---|---|
| catcatcaat | aatatacccc | acaaagtaaa | caaaagttaa | tatgcaaatg agcttttgaa | 60 |
| tttagggcgg | ggccgtcgct | gattggccgt | tgcaagaacc | gttagtgacg tcacgacgca | 120 |
| cggccgacgc | tcgccgcgga | ggcgtggcct | agcccggaag | caagtcgcgg ggctgatgac | 180 |
| gtataaaaaa | gcggacttta | gacccggaaa | cggccgattt | tcccgcggcc acgcccggat | 240 |

```
atgaggtaat tctgggcgga tgcaagtgaa attaggtcat tttggcgcga aaactgaatg      300
aggaagtgaa aagcgaaaaa taccggtccc tcccagggcg gaatatttac cgagggccga      360
gagactttga ccgattacgt gggggtttcg attgcggtgt tttttcgcg aatttccgcg       420 tccgtgtcaa agtccggtgt ttatgtcaca gatcagctga tagctgctgt tggagaacga      480
tgccttctcc agggtgaacc tgaacggcat ctttgacatg gatgtctcgg tgtacaagat      540
cctgagatac gatgagacca agtccagggt gcgcgcttgc gagtgcgggg gcagacacac      600
caggatgcag ccagtggccc tggatgtgac cgaggagctg agaccagacc acctggtgat      660
ggcctgtacc gggaccgagt tcagctccag tggggaggac acagattaga ggtaggtttt      720
tgagtagtgg gcgtggctaa tgtgagtata aaggtgggtg tcttacgagg gtcttttgc       780 ttttctgcag acatcatgaa cgggaccggc gggcccttcg aagggggggct ttttagccct     840 tatttgacaa cccgcctgcc gggatgggcc ggagttcgtc agaatgtgat gggatcgacg      900
gtggatgggc gcccagtgct tccagcaaat tcctcgacca tgacctacgc gaccgtgggg      960
agctcgtcgc tcgacagcac cgccgcagcc gcggcagccg cagccgccat gacagcgacg      1020
agactggcct cgagctacat gcccagcagc ggcagcagcc cctctgtgcc cagttccatc      1080
atcgccgagg agaaactgct ggccctgctg gccgagctgg aagccctgag ccgccagctg      1140
gccgccctga cccagcaggt gtctgagctc cgcgagcagc agcagcagca aaataaatga      1200
ttcaataaac acagattctg attcaaacag caaagcatct ttattattta ttttttcgcg      1260
cgcggtaggc cctggtccac ctctcccgat cattgagagt gcggtggatt ttttccagga     1320
cccggtagag gtgggattgg atgttgaggt acatgggcat gagcccgtcc ggggggtgga     1380
ggtagcacca ctgcatggcc tcgtgctctg gggtcgtgtt gtagatgatc cagtcatagc     1440
aggggcgctg ggcgtggtgc tggatgatgt ctttaaggag gagactgatg gccacgggga     1500
gccccttggt gtaggtgttg gcaaagcggt tgagctggga aggatgcatg cgggggggaga    1560 tgatgtgcag tttggcctgg atcttgaggt tggcaatgtt gccgcccaga tcccgcctgg     1620
ggttcatgtt gtgcaggacc accaggacgg tgtagcccgt gcacttgggg aacttatcat     1680
gcaacttgga agggaatgcg tggaagaatt tggagacgcc cttgtgcccg cccaggtttt     1740
ccatgcactc atccatgatg atggcgatgg gcccgtgggc tgcggctttg gcaaagacgt     1800
ttctggggtc agagacatcg taattatgct cctgggtgag atcgtcataa gacatttaa      1860 tgaatttggg gcggagggtg ccagattggg ggacgatggt tccctcgggc cccggggcga     1920
agttcccctc gcagatctgc atctcccagg ctttcatctc ggagggggggg atcatgtcca    1980 cctgcggggc tatgaaaaaa acggtttccg gggcggggt gatgagctgc gaggagagca      2040
ggtttcttaa cagctgggac ttgccgcacc cggtcgggcc gtatatgacc ccgatgacgg     2100
gttgcaggtg gtagttcaag gacatgcagc tgccgtcgtc ccggaggagg ggggccacct    2160
cgttgagcat gtctctgact tggaggtttt cccggacgag ctcgccgagg aggcggtccc     2220
cgcccagcga gagcagctct tgcagggaag caaagttttt caggggcttg agcccgtcgg    2280
ccatgggcat cttggcgagg gtctgcgaga ggagctccag gcggtcccag agctcggtga    2340
cgtgctctac ggcatctcga tccagcagac ttcctcgttt cggggttgg gacgactgcg     2400 actgtagggc acgagacgat gggcgtccag gcggccagc gtcatgtcct tccagggtct     2460
cagggtccgc gtgaggggtt gtctccgtcac ggtgaagggg tgggcccgg gctgggcgct    2520 tgcaagggtt cgcttgagac tcatcctgct ggtgctgaaa cggcacggt cttcgccctg     2580 cgcgtcggcg agatagcagt tgaccatgag ctcgtagttg agggcctcgg cggcgtggcc    2640
```

```
cttggcgcgg agcttgccct tggaagagcg cccacaggcg ggacagagga gggattgcag   2700
ggcgtatagc ttgggtgcga gaaagacgga ctcggggcg aacgcgtccg ctccgcagtg    2760
ggcgcagacg gtctcgcact cgacgagcca ggtgagctcg ggttgttcgg ggtcaaaaac   2820
cagttttccc ccgttctttt tgatgcgctt cttacctcgc gtctccatga gtctgtgtcc   2880
gcgctcggtg acaaacaggc tgtcggtgtc cccgtagatg gacttgattg gcctgtcctg   2940
caggggcgtc ccgcggtcct cctcgtagag aaattcggac cactctgaga cgaaggcgcg   3000
cgtccacgcc aagacaaagg aggccacgtg cgaggggtag cggtcgttgt ccaccagggg   3060
gtccaccttt tccaccgtgt gcaagcacat gtcccctcc tccgcatcca agaaggtgat    3120
tggcttgtag gtgtaggcca cgtgaccggg ggtccccgac ggggggtat aaaaggggc     3180 gggtctgtgc tcgtcctcac tctcttccgc gtcgctgtcc acgagcgcca gctgttgggg   3240
taggtattcc ctctcgagag cgggcatgac ctcggcactc aggttgtcag tttctagaaa   3300
cgaggaggat ttgatgttgg cttgccctgc cgcgatgctt tttaggagac tttcatccat   3360
ctggtcagaa aagactattt ttttattgtc aagcttggtg gcaaaggagc catagagggc   3420
gttggagaga agcttggcga tggatctcat ggtctgattt ttgtcacggt cggcgcgctc   3480
cttggccgcg atgttgagct ggacatactc gcgcgcgacg cacttccatt cggggaagac   3540
ggtggtgcgc tcgtcgggca cgatcctgac gcgccagccg cggttatgca gggtgaccag   3600
gtccacgctg gtggccacct cgccgcgcag gggctcgttg gtccagcaga gtctgccacc   3660
cttgcgcgag cagaacgggg gcagcacatc caggaggtgc tcgtcagggg ggtccgcatc   3720
gatggtgaag atgcccggac agagttcctt gtcaaaataa tcgattttg aggatgcatc    3780 atccaaggcc atctgccact cgcgggcggc cagcgctcgc tcgtagggggt tgaggggcgg   3840 accccagggc atgggatgcg tgaggcgga ggcgtacatg ccgcagatgt catagacata    3900
gatgggctcc gagaggatgc cgatgtaggt gggataacag cgccccccgc ggatgctggc   3960
gcgcacgtag tcatacaact cgtgcgaggg ggccaagaag gagggggccga gattggtgcg   4020 ctggggctgc tcggcgcgga agacgatctg gcgaaagatg gcgtgcgagt tggaggagat   4080
ggtgggccgt tggaagatgt taaagtgggc gtggggcagg cggaccgagt cgcggatgaa   4140
gtgcgcgtag gagtcttgca gcttggcgac gagctcggcg gtgacgagga cgtccatggc   4200
gcagtagtcc agcgtttcgc ggatgatgtc ataacccgct tctcctttct tctcccacag   4260
ctcgcggttg agggcgtact cctcgtcatc cttccagtac tcccggagcg ggaatcctcg   4320
atcgtccgca cggtaagagc ccagcatgta gaaatggttc acggccttgt agggacagca   4380
gcccttctcc acggggaggg cgtaagcttg agcggccttg cggagcgagg tgtgcgtcag   4440
ggcgaaggtg tccctgacca tgactttcaa gaactgtac ttgaagtccg agtcgtcgca    4500
gccgccgtgc tcccagagct cgaaatcggt gcgcttcttc gagagggggt taggcagagc   4560
gaaagtgacg tcattgaaga gaatcttgcc tgcccgcgc atgaaattgc gggtgatgcg    4620
gaaagggccc gggacggagg ctcggttgtt gatcacctgg gcggcgagga cgatctcgtc   4680
gaagccgttg atgttgtgcc cgacgatgta gagttccatg aatcgcgggc ggcctttgat   4740
gtgcggcagc ttttttgagct cctcgtaggt gaggtcctcg gggcattgca ggccgtgctg   4800
ctcgagcgcc cactcctgga gatgtgggtt ggcttgcatg aaggaagccc agagctcgcg   4860
ggccatgagg gtctggagct cgtcgcgaaa gaggcggaac tgctggccca cggccatctt   4920
ttctggtgtg acgcagtaga aggtgagggg gtcccgctcc cagcgatccc agcgtaagcg   4980
```

```
cacggcgaga tcgcgagcca gggcgatcag ctcggggtcc ccggagaatt tcatgaccag    5040
catgaagggg acgagctgct tgccgaagga ccccatccag gtgtaggttt ctacatcgta    5100
ggtgacaaag agcctctccg tgcgaggatg agagccgatt gggaagaact ggatttcctg    5160
ccaccagttg gacgagtggc tgttgatgtg atgaaagtag aaatcccgcc ggcgaaccga    5220
gcactcgtgc tgatgcttgt aaaagcgtcc gcagtactcg cagcgctgca cgggctgtac    5280
ctcatccacg agatacacag cgcgtccctt gaggaggaac ttcaggagtg gcggccctgg    5340
ctggtggttt tcatgttcgc ctgcgtggga ctcaccctgg ggctcctcga ggacggagag    5400
gctgacgagc ccgcgcggga gccaggtcca gatctcggcg cggcggggc ggagagcgaa    5460 gacgagggcg cgcagttggg agctgtccat ggtgtcgcgg agatccaggt ccgggggcag    5520
ggttctgagg ttgacctcgt agaggcgggt gagggcgtgc ttgagatgca gatggtactt    5580
gatttctacg ggtgagttgg tggccgtgtc cacgcattgc atgagcccgt agctgcgcgg    5640
ggccacgacc gtgccgcggt gcgcttttag aagcggtgtc gcggacgcgc tcccggcggc    5700
agcggcggtt ccgccccgc gggcaggggc ggcagaggca cgtcgcgtg gcgctcgggc    5760 aggtcccggt gctgcgccct gagagcgctg gcgtgcgcga cgacgcgtcg gttgacatcc    5820
tggatctgcc gcctctgcgt gaagaccact ggccccgtga ctttgaacct gaaagacagt    5880
tcaacagaat caatctcggc gtcattgacg gcggcctgac gcaggatctc ttgcacgtcg    5940
cccgagttgt cctggtaggc gatttcggac atgaactgct cgatctcctc ctcctggaga    6000
tcgccgcggc cagcgcgctc gacggtggcg gcgaggtcat tcgagatgcg acccatgagc    6060
tgcgagaagg cgcccaggcc gctctcgttc cagacgcggc tgtagaccac gtccccgtcg    6120
gcgtcgcgcg cgcgcatgac cacctgcgcg aggttgagct ccacgtgccg cgtgaagacg    6180
gcgtagttgc gcaggcgctg gaagaggtag ttgagggtgg tggcgatgtg ctcggtgacg    6240
aagaagtaca tgatccagcg gcgcagggc atctcgctga tgtcgccgat ggcctccagc    6300
ctttccatgg cctcgtagaa atccacgcg aagttgaaaa actgggcgtt gcgggccgag    6360
accgtgagct cgtcttccaa gagccggatg agctcggcga tggtggcgcg cacctcgcgc    6420
tcgaaacccc cggggcctc ctcctcttcc tcttcttcca tgacgacctc ttcttctatt    6480
tcttcctctg ggggcggtgg tggtggcggg gcccgacgac gacggcggcg caccgggaga    6540
cggtcgacga agcgctcgat catctccccg cggcggcgac gcatggtttc ggtgacggcg    6600
cgaccccgtt cgcgaggacg cagcgtgaag acgccgccgg tcatctcccg gtaatggggc    6660
gggtccccgt tgggcagcga gagggcgctg acgatgcatc ttatcaattg cggtgtaggg    6720
gacgtgagcg cgtcgagatc gaccggatcg gagaatcttt cgaggaaagc gtctagccaa    6780
tcgcagtcgc aaggtaagct caaacacgta gcagccctgt ggacgctgtt agaattgcgg    6840
ttgctgatga tgtaattgaa gtaggcgttt ttaaggcggc ggatggtggc gaggaggacc    6900
aggtccttgg gtcccgcttg ctggatgcgg agccgctcgg ccatgcccca ggcctggccc    6960
tgacaccggc tcaggttctt gtagtagtca tgcatgagcc tttcaatgtc atcactggcg    7020
gaggcggagt cttccatgcg ggtgaccccg acgcccctga gcggctgcac gagcgccagg    7080
tcggcgacga cgcgctcggc gaggatggcc tgttgcacgc gggtgagggt gtcctggaag    7140
tcgtccatgt cgacgaagcg gtggtaggcc cctgtgttga tggtgtaggt gcagttggcc    7200
atgagcgacc agttgacggt ctgcaggccg ggttgcacga cctcggagta cctgatccgc    7260
gagaaggcgc gcgagtcgaa gacgtagtcg ttgcaggtgc gcacgaggta ctggtagccg    7320
actaggaagt gcggcggcgg ctggcggtag agtggccagc gctgggtggc cggcgctccc    7380
```

```
ggggccaggt cctcgagcat gaggcggtgg tagccgtaga ggtagcggga catccaggtg    7440
atgccggcgg cagtggtgga ggcgcgcggg aactcgcgga cgcggttcca gatgttgcgc    7500
agcggcagga aatagtccat ggtcggcacg gtctggccgg tgagacgcgc gcagtcattg    7560
acgctctaga ggcaaaaacg aaagcggttg agcgggctct tcctccgtag cctggcggaa    7620
cgcaaacggg ttaggccgcg tgtgtacccc ggttcgagtc ccctcgaatc aggctggagc    7680
cgcgactaac gtggtattgg cactcccgtc tcgacccgag cccgatagcc gccaggatac    7740
ggcggagagc ccttttttgcc ggccgagggg agtcgctaga cttgaaagcg gccgaaaacc   7800
ctgccgggta gtggctcgcg cccgtagtct ggagaagcat cgccagggtt gagtcgcggc    7860
agaacccggt tcgcggacgg ccgcggcgag cgggacttgg tcaccccgcc gatttaaaga    7920
cccacagcca gccgacttct ccagttacgg gagcgagccc ccttttttct ttttgccaga    7980
tgcatcccgt cctgcgccaa atgcgtccca ccccccggc gaccaccgcg accgcggccg     8040
tagcaggcgc cggcgctgta gccccgccac agacagagat ggacttggaa gagggcgaag    8100
ggctggcgag actgggggcg ccgtccccgg agcgacaccc ccgcgtgcag ctgcagaagg    8160
acgtgcgccc ggcgtacgtg cctccgcaga acctgttcag ggaccgcagc ggggaggagc    8220
ccgaggagat gcgcgactgc cggtttcggg cgggcaggga gctgcgcgag ggcctggacc    8280
gccagcgcgt gctgcgcgac gaggatttcg agccgaacga gcagacgggg atcagccccg    8340
cgcgcgcgca cgtggcggcg gccaacctgg tgacggccta cgagcagacg gtgaagcagg    8400
agcgcaactt ccaaaagagt ttcaacaacc acgtgcgcac cctgatcgcg cgcgaggagg    8460
tggccctggg cttgatgcac ctgtgggacc tggcggaggc catcgtgcag aacccggaca    8520
gcaagcctct gacggcgcag ctgttcctgg tggtgcagca cagcagggac aacgaggcgt    8580
tcagggaggc gctgctgaac atcgccgagc ccgagggtcg ctggctgctg agctgattta   8640
acatcttgca gagcatcgta gtgcaggagc gcagcttgag cctggccgag aaggtggcgg    8700
cgatcaacta ctcggtgctg agcctgggca agttttacgc gcgcaagatt tacaagacgc    8760
cgtatgtgcc catagacaag gaggtgaaga tagacagctt ttacatgcgc atggcgctca    8820
aggtgctgac gctgagcgac gacctgggcg tgtaccgcaa cgaccgcatc cacaaggccg    8880
tgagcacgag ccggcggcgc gagctgagcg accgcgagct gatgctgagc ctgcgccggg    8940
cgctggtagg gggcgccgcc ggcggcgagg agtcctactt cgacatgggg gcggacctgc    9000
attggcagcc gagccggcgc gccttggagg ccgcctacgg tccagaggac ttggaagagg    9060
atgaggaaga ggaggaggat gcaccccgctg cggggtactg acgcctccgt gatgtgtttt   9120
tagatgtccc agcaagcccc ggaccccgcc ataagggcgg cgctgcaaag ccagccgtcc    9180
ggtctagcat cggacgactg ggaggccgcg atgcaacgca tcatggccct gacgaccgc    9240
aaccccgagt cctttagaca acagccgcag gccaacagac tctcggccat tctggaggcg    9300
gtggtccccct ctcggaccaa ccccacgcac gagaaggtgc tggcgatcgt gaacgcgctg   9360
gcggagaaca aggccatccg tcccgacgag gccgggctgg tgtacaacgc cctgctggag    9420
cgcgtgggcc gctacaacag cacgaacgtg cagtccaacc tggaccggct ggtgacggac    9480
gtgcgcgagg ccgtggcgca gcgcgagcgg ttcaagaacg agggcctggg ctcgctggtg    9540
gcgctgaacg ccttcctggc gacgcagccg gcgaacgtgc cgcgcgggca ggacgattac    9600
accaacttta tcagcgcgct gcggctgatg gtgaccgagg tgcccagag cgaggtgtac    9660
cagtcggggcc ctgactactt tttccagacg agccggcagg gcttgcagac ggtgaacctg    9720
```

-continued

```
agtcaggctt tcaagaacct gcgcgggctg tggggcgtgc aggcgcccgt gggcgaccgg    9780
tcgacggtga gcagcttgct gacgcccaac tcgcggctgc tgctgttgct gatcgcgccc    9840
tttactgaca gcggcagcgt aaaccgcaac tcgtacctgg gccacctgct gacgctgtac    9900
cgcgaggcca taggccaggc acaggtggac gagcagacct tccaggaaat tacgagcgtg    9960
agccgcgcgc tggggcagaa cgacaccgac agtctgaggg ccaccctgaa cttttttgctg    10020 accaatagac agcagaagat cccggcgcag tacgcactgt cggccgagga ggaaaggatc    10080
ctgagatatg tgcagcagag cgtagggctg ttcctgatgc aggagggtgc caccccccagc    10140 gccgcgctgg acatgaccgc gcgcaacatg gaacctagca tgtacgccgc caaccggccg    10200
ttcatcaata agctgatgga ctacctgcac cgcgcggcgg ccatgaacac ggactacttt    10260
accaacgcca tcctgaaccc gcactggctc ccgccgccgg gtttctacac gggcgagtac    10320
gacatgcccg accccaacga cgggttcctg tgggacgacg tggacagcgc ggtgttctcg    10380
ccggcctttc aaaagcgtca ggaggcgccg ccgagcgagg gcgcggtggg gagaagcccc    10440
tttcctagct tagggagttt gcatagcttg ccgggctcgg tgaacagcgg cagggtgagc    10500
cggccgcgct tgctgggcga ggacgagtac ctgaacgact cgctactgca gccgccgcgg    10560
gccaagaacg ccatggccaa taacgggata gagagtctgg tggacaaaact gaaccgctgg    10620 aagacctacg ctcaggacca tagggacgcg cccgcgccgc ggcgacagcg ccacgaccgg    10680
cagcggggcc tggtgtggga cgacgaggac tcggccgacg atagcagcgt gttggacttg    10740
ggcgggagcg gtggggccaa cccgttcgca catctgcagc ccaaactggg gcggcggatg    10800
ttttgaaatg caaaataaaa ctcaccaagg ccatagcgtg cgttctcttc cttgttagag    10860
atgaggcgcg cggtggtgtc ttcctctcct cctccctcgt acgagagcgt gatggcgcag    10920
gcgaccctgg aggttccgtt tgtgcctccg cggtatatgg ctcctacgga gggcagaaac    10980
agcattcgtt actcggagct ggctccgcag tacgacacca ctcgcgtgta cttggtggac    11040
aacaagtcgg cggacatcgc ttctctgaac taccaaaacg accacagcaa cttcctgacc    11100
acggtggtgc agaacaacga tttcaccccc gccgaggcca gcacgcagac gataaatttt    11160
gacgagcggt cgcggtgggg cggtgatctg aagaccattc tgcacaccaa catgcccaat    11220
gtgaacgagt acatgttcac cagcaagttt aaggcgcggg tgatggtggc tagaaagcat    11280
cccaaagatg tagatgccag tgatttaagc aaggatatct tagagtatga ttggtttgag    11340
tttaccctgc ccgagggcaa cttttccgag accatgacca tagacctgat gaacaacgcc    11400
atcttggaaa actacttgca agtggggcgg caaaatggcg tgctggagag cgatatcggt    11460
gtcaagtttg acagcaggaa tttcaagctg ggctgggacc cggtgaccaa gctggtgatg    11520
cctggggtct acacctacga ggccttccac ccggacgtgg tgctgctgcc gggctgcggg    11580
gtggacttca ccgagagtcg tctgagcaac ctcctgggca ttcgcaagaa gcaacctttc    11640
caagagggct tcagaatcat gtatgaggat ctagtagggg gcaacatccc cgccctcctg    11700
aatgtcaagg agtatctgaa ggataaggaa gaagctggca cagcagatgc aaataccatt    11760
aaggctcaga atgatgcagt cccaagagga gataactatg catcagcggc agaagccaaa    11820
gcagcaggaa aagaaattga gttgaaggcc attttgaaag atgattcaaa cagaagctac    11880
aatgtgatcg agggaaccac agacaccctg taccgcagtt ggtacctgtc ctataccctac    11940 ggtgatcccg agaagggagt gcagtcgtgg acactgctta ccaccccgga cgtcacctgc    12000
ggcgcggagc aagtctactg gtcgctgccg gacctcatgc aagaccccgt caccttccgc    12060
tctacccagc aagtcagcaa ctaccccgtg gtcggcgccg agctcatgcc tttccgcgcc    12120
```

```
aagagctttt acaacgacct cgccgtctac tctcagctca tccgcagcta cacctccctc    12180
acccacgtct tcaaccgctt ccccgacaac cagatcctct gccgcccgcc cgcgccaccc    12240
atcaccaccg tcagtgaaaa cgtgcctgct ctcacagatc acgggacgct accgctgcgc    12300
agcagtatcc gcggagtcca gcgagtgacc gtcactgacg cccgtcgccg cacctgtccc    12360
tacgtctaca aggccctggg catagtcgcg ccgcgcgtgc tttccagtcg caccttctaa    12420
aaaatgtcta ttctcatctc gcccagcaat aacaccggct ggggtcttac taggcccagc    12480
accatgtacg gaggagccaa gaagcgctcc cagcagcacc ccgtccgcgt ccgcggccac    12540
ttccgcgctc cctggggcgc ttacaagcgc gggcggactt ccaccgccgc cgtgcgcacc    12600
accgtcgacg acgtcatcga ctcggtggtc gccgacgcgc gcaactatac ccccgccccc    12660
tccaccgtgg acgcggtcat cgacagcgtg gtggccgatg cacgcgacta tgccagacgc    12720
aagagccggc ggcgacggat cgccaggcgc caccggagca cgcccgccat gcgcgccgcc    12780
cgggctctgc tgcgccgcgc cagacgcacg ggccgccggg ccatgatgcg agccgcgcgc    12840
cgcgctgcca ctgcacccac ccccgcaggc aggactcgca gacgagcggc cgccgccgcc    12900
gccgcggcca tttctagcat gaccagaccc aggcgcggaa acgtgtactg ggtgcgcgac    12960
tccgtcacgg gcgtgcgcgt gcccgtgcgc accgtcctc ctcgtccctg atctaatgct    13020
tgtgtcctcc cccgcaagcg acgatgtcaa agcgcaaaat caaggaggag atgctccagg    13080
tcgtcgcccc ggagatttac ggaccccgg accagaaacc ccgcaaaatc aagcgggtta    13140
aaaaaaagga tgaggtggac gaggggggcag tagagtttgt gcgcgagttc gctccgcggc    13200
ggcgcgtaaa ttggaagggg cgcagggtgc agcgcgtgtt gcggcccggc acggcggtgg    13260
tgttcacgcc cggcgagcgg tcctcggtca ggagcaagcg tagctatgac gaggtgtacg    13320
gcgacgacga catcctggac caggcggcgg agcgggcggg cgagttcgcc tacgggaagc    13380
ggtcgcgcga agaggagctg atctcgctgc cgctggacga aagcaacccc acgccgagcc    13440
tgaagcccgt gaccctgcag caggtgctgc cccaggcgat gctgctgccg agccgcgggg    13500
tcaagcgcga gggcgagagc atgtacccga ccatgcagat catggtgccc aagcgccggc    13560
gcgtggagga cgtgctggac accgtgaaaa tggatgtgga gcccgaggtc aaggtgcgcc    13620
ccatcaagca ggtggcgccg ggcctgggcg tgcagaccgt ggacattcag atccccaccg    13680
acatggatgt cgacaaaaaa ccctcgacca gcatcgaggt gcagactgac ccctggctcc    13740
cagcctccac cgctaccgtc tctacttcta ccgccgccac ggctaccgag cctacaagga    13800
ggcgaagatg gggcgccgcc agccggctga tgcccaacta cgtgttgcat ccttccatca    13860
tcccgacgcc gggctaccgc ggcacccggt actacgccag ccgcaggcgc ccagccagca    13920
aacgccgccg ccgcaccgcc acccgccgcc gtctggcccc cgcccgcgtg cgccgcgtaa    13980
ccacgcgccg gggccgctcg ctcgttctgc ccaccgtgcg ctaccacccc agcatccttt    14040
aatccgtgtg ctgtgatact gttgcagaga gatggctctc acttgccgcc tgcgcatccc    14100
cgtcccgaat taccgaggaa gatcccgccg caggagaggc atggcaggca gcggcctgaa    14160
ccgccgccgg cggcgggcca tgcgcaggcg cctgagtggc ggctttctgc ccgcgctcat    14220
ccccataatc gccgcggcca ttggcacgat cccgggcata gcttccgttg cgctgcaggc    14280
gtcgcagcgc cgttgatgtg cgaataaagc ctctttagac tctgacacac ctggtcctgt    14340
atatttttag aatggaagac atcaattttg cgtccctggc tccgcggcac ggcacgcggc    14400
cgttcatggg cacctggaac gagatcggca ccagccagct gaacgggggc gccttcaatt    14460
```

```
ggagcagtgt ctggagcggg cttaaaaatt tcggctcgac gctccggacc tatgggaaca    14520
aggcctggaa tagtagcacg gggcagttgt taagggaaaa gctcaaagac cagaacttcc    14580
agcaaaaggt ggtggacggc ctggcctcgg gcattaacgg ggtggtggac atcgcgaacc    14640
aggccgtgca gcgcgagata aacagccgcc tggacccgcg gccgcccacg gtggtggaga    14700
tggaagatgc aactcttccg ccgcccaaag gcgagaagcg cccgcggccc gacgcggagg    14760
agacgatcct gcaggtggac gagccgcccc cgtacgagga ggccgtcaag gccggcatgc    14820
ccaccacgcg catcatcgcg ccgctggcca cgggtgtaat gaaacccgcc acccttgacc    14880
tgcctccacc acccacgccc gctccaccga aggcagctcc ggtcgtgcag gccccccgg     14940 tggcgaccgc cgtgcgccgc gtccccgccc gccgccaggc ccagaactgg cagagcacgc    15000
tgcacagtat cgtgggcctg ggagtgaaaa gtctgaagcg ccgccgatgc tattgagaga    15060
gaggaaagag gacactaaag ggagagctta acttgtatgt gccttaccgc cagagaacgc    15120
gcgaagatgg ccaccccctc gatgatgccg cagtgggcgt acatgcacat cgccgggcag    15180
gacgcctcgg agtacctgag cccgggtctg gtgcagtttg cccgcgccac cgacacgtac    15240
ttcagcctgg gcaacaagtt taggaacccc acggtggctc ccaccacga tgtgaccacg     15300 gaccggtccc agcgtctgac gctgcgcttc gtgcccgtgg atcgcgagga caccacgtac    15360
tcgtacaagg cgcgcttcac tctggccgtg ggagacaacc gggtgctaga catggccagc    15420
acttactttg acatccgcgg cgtcctggac cgcggtccca gcttcaaacc ctactcgggc    15480
acggcttaca acagcctggc ccccaagagc gctcccaatc ccagccagtg ggatgcaaag    15540
gaaaaggaag gagttgccca acagaaaaaa atgttttaa aaacatttgg tgttgccgct     15600
acaggtggtt ttaatattac agatcagggt ttgttacttg gaactgagga aacagctgaa    15660
aacgttaaaa aggatatcta tgcagagaaa actttccagc ctgaacctca agttggtgaa    15720
gaaaactggc aggaaagtga agcctttat ggaggaaggg ctattaagaa agacaccaaa     15780
atgaagccat gctatggttc atttgccaga cccactaatg aaaaaggagg acaggctaaa    15840
tttaaaacac tagatgggca agttacaaaa gatccagata ttgactttgc ttactttgac    15900
gtccctggcg gaaaagctcc aacaggcagt agtctaccgg aagaatacaa agcagatata    15960
attttgtaca cagaaaatgt taatctggaa acaccagata ctcacatagt gtataaacct    16020
ggcaaagaag atgacaattc tgaaattaac ttaacacaac agtccatgcc aaacagaccc    16080
aactacattg ctttaggga caactttgta ggtctcatgt actacaacag tactggcaac    16140
atgggtgtgc tggctggtca ggcctctcag ttgaatgctg tggtggactt gcaagacaga    16200
aacaccgagc tgtcttacca gctcttgcta gattctctgg gtgacagaac cagatacttt    16260
agcatgtgga actctgcggt tgacagttat gatcccgatg tcaggatcat tgagaatcac    16320
ggtgtggaag atgaacttcc aaactattgc ttcccattga atggcactgg taccaattcc    16380
acctatcaag gtgtaaaaat tacaggtaat aatgatggcg atcttgaaac cgaatgggaa    16440
agagatgaag caatctctag acaaaaccaa atctgcaagg gcaacgtcta tgccatggag    16500
atcaacctcc aggccaacct gtggaagagt tttctgtact cgaacgtagc cctgtacctg    16560
cctgactcat acaagtacac gccggccaac gtcacgctgc ccgccaacac caacacctac    16620
gagtacatga acggccgcgt ggtagccccc tcgctggtgg acgcttacat caacatcggc    16680
gcccgctggt cgctggatcc catggacaat gtaaacccat tcaaccacca ccgcaacgcg    16740
ggcctgcgct accgttccat gttgttgggc aacggtcgct acgtgccctt ccacatccaa    16800
gtgccccaaa agttctttgc catcaagaac ctgcttctgc tcccgggctc ctacacctac    16860
```

```
gagtggaact tccgcaagga cgtcaacatg atcctgcaga gttccctcgg aaacgatctg   16920
cgcgtcgacg gcgcctccgt ccgcttcgac agcgtcaacc tctacgccac cttcttcccc   16980
atggcgcaca acaccgcctc caccctggaa gccatgctgc gcaacgacac caacgaccag   17040
tccttcaacg actacctctc ggccgccaac atgctctacc ccatcccggc caaggccacc   17100
aacgtgccca tctccatccc ctcacgcaac tgggccgcct ccgcggctg gagtttcacc    17160 aggctcaaga ccaaggaaac tccctcgcta ggctcgggtt tcgacccata ctttgtctac   17220
tcgggctcca tccctatct cgacgggacc ttctacctca atcacacctt caagaaggtc    17280
tccatcatgt tcgactcctc ggtcagctgg cccggcaacg accggctgct cacgccgaac   17340
gagttcgaga tcaagcgcag cgtcgacggg gagggctaca acgtggccca atgcaacatg   17400
accaaggact ggttcctcgt ccagatgctc tcccactaca acatcggcta ccagggcttc   17460
cacgtgcccg agggctacaa ggaccgcatg tactccttct ccgcaacttc cagcccatg    17520 agcaggcagg tggtcgatga gatcaactac aaggactaca aggccgtcac cctgcccttc   17580
cagcacaaca actcgggctt caccggctac ctcgcaccca ccatgcgtca ggggcagccc   17640
taccccgcca acttccccta cccgctcatc ggccagacag ccgtgccctc cgtcacccag   17700
aaaaagttcc tctgcgacag ggtcatgtgg cgcatcccct ctccagcaa cttcatgtcc    17760 atgggcgccc tcaccgacct gggtcagaac atgctctacg ccaactcggc ccatgcgctc   17820
gacatgacct tcgaggtgga ccccatggat gagcccaccc tcctctatct tctcttcgaa   17880
gttttcgacg tggtcagagt gcaccagccg caccgcggcg tcatcgaggc cgtctacctg   17940
cgcacgccct tctccgccgg aaacgccacc acataagcat gagcggctcc agcgaaagag   18000
agctcgcggc catcgtgcgc gacctgggct gcgggcccta cttttgggc acccacgaca    18060 agcgcttccc tggcttcctc gccggcgaca agctggcctg cgccatcgtc aacacggccg   18120
gccgcgagac cggaggcgtg cactggctcg ccttcggctg gaaccgcgc tcgcgcacct    18180 gctacatgtt cgacccattt gggttctcgg accgccggct caagcagatt tacagcttcg   18240
agtacgaggc tatgctgcgc cgaagcgccc tggcttcctc gccagaccgc tgtctcagcc   18300
tcgagcagtc cacccagacc gtgcagggggc ccgactccgc cgcctgcgga cttttctgtt   18360
gcatgttctt gcatgccttc gtgcactggc ccgaccgacc catggacggg aaccccacca   18420
tgaacttgct gacggggtgt cccaacggca tgctacaatc gccacaggtg ctgcccaccc   18480
tccggcgcaa ccaggaggag ctctaccgct tcctcgcgcg ccactcccct tactttcgat   18540
cccaccgcgc cgccatcgaa cacgccaccg cttttgacaa aatgaaacaa ctgcgtgtat   18600
ctcaataaac agcacttttta ttttacatgc actggagtat atgcaagtta tttaaaagtc   18660
gaaggggttc tcgcgctcgt cgttgtgcgc gcgctgggg agggccacgt tgcggtactg    18720
atacttgggc tgccacttga actcggggat caccagtttg ggcactgggg tctcggggaa   18780
ggtctcgctc cacatgcgcc ggctcatctg cagggcgccc agtatgtccg gggcggagat   18840
cttgaaatcg cagttggggc cggtgctctg cgcgcgcgag ttgcggtaca cggggttgca   18900
gcactggaac accatcagac tggggtactt cacactggcc agcacgctct tgtcgctgat   18960
ctgatccttg tccaggtcct cggcgttgct caggccgaac ggggtcatct tgcacagctg   19020
gcggcccagg aagggcacgc tctgaggctt gtggttacac tcgcagtgca cgggcatcag   19080
catcatcccc gcaccgcgct gcatattcgg gtagagggcc ttgacaaagg ccagagatctg   19140 cttgaaagct tgctgggcct tggcccccctc gctgaagaac agaccacagc tcttcccgct   19200
```

```
gaactggtta ttcccgcacc cggcatcatg cacgcagcag cgcgcgtcat ggctggtcag    19260
ttgcaccacg ctccgtcccc agcggttctg ggtcaccttg gccttgctgg gttgctcctt    19320
caacgcgcgc tgcccgttct cgctggtcac atccatctcc accacgtggt ccttgtggat    19380
catcaccgtc ccatgcagac acttgagctg gccttccacc tcggtgcagc cgtgatccca    19440
cagggcgcat ccggtgcact cccaattctt gtgtgcgatc ccgctgtggc tgaagatgta    19500
accttgcaac atgcggccca tgacggtgct aaatgctttc tgggtggtga aggtcagttg    19560
catcccgcgg acctcctcgt tcatccaggt ctggcacatc ttctggaaga tctcggtctg    19620
ctcgggcatg agcttgtaag catcgcgcag gccgctgtcg acgcggtagc gttccatcag    19680
tacgttcatg gtatccatgc ccttctccca ggacgagacc agaggcagac tcaggggtt    19740
gcgcacgttc aggacacctg gggtcgcggg ctcgacgatg cgttttccgt ccttgtcttc    19800
cttcaacaga accggaggct ggctgaatcc cactcccacg atcacggcat cttcctgggg    19860
catctcttcg tcggggtcta ccttggtcac atgcttggtc tttctggctt gcttcttttt    19920
tggaggactg tccacgggga ccacgtcctc ctcggaagac ccggagccca cccgctgata    19980
ctttcggcgc ttggtgggca gaggaggtgg cggcgagggg ctcctctcct gctccggcgg    20040
atagcgcgcc gacccgtggc cccggggcgg agtggcctct cggtccatga accggcgcac    20100
gtcctgactg ccgccggcca ttatttccta ggggaagatg gaggagcagc cgcgtaagca    20160
ggagcaggag gaggacttaa ccacccacga gcaacccaaa atcgagcagg acctgggctt    20220
cgaagagccg gctcgtctag aaccccaca ggatgaacag gagcacgagc aagacgcagg    20280
ccaggaggag accgacgctg ggctcgagca tggctacctg ggaggagagg aggatgtgct    20340
gctgaaacac ctgcagcgcc agtccctcat cctccgggat gccctggccg accggagcga    20400
aacccccctc agcgtcgagg agctgtgtcg ggcctacgag ctcaacctat tctcgccgcg    20460
cgtgcccccc aaacgccagc ccaacggcac atgcgagccc aacccgcgtc tcaacttcta    20520
tcccgtcttt gcggtccccg aggcccttgc cacctatcac atcttttttca agaaccaaaa    20580
gatccccgtc tcctgtcgcg ccaaccgcac ccgcgccgac cgctcctcg ctctggggcc    20640
cggcgcacac atacctgata tcgcttccct ggaagaggtg cccaagatct tcgaagggct    20700
cggtcgggac gagacgcgcg cggcgaacgc tctgaaagaa acagcagagg aagagggtca    20760
cactagcgcc ctggtagagt tggaaggcga caacgctagg ctggccgtgc tcaagcgcag    20820
tgtcgagctc acccacttcg cctaccccgc cgtcaacctc ccgcccaagg tcatgcgtcg    20880
catcatggat cagctcatca tgccccacat cgaggccctc gatgaaagtc aggagcagcg    20940
cccccgaggac gtccggcccg tggtcagcga cgagatgctc gcgcgctggc tcggaacccg    21000
cgaccccag gctttggaac agcggcgcaa actcatgctg gccgtggtcc tggtcaccct    21060
cgagctcgaa tgcatgcgcc gcttcttcag cgaccccgag accctacgca aagtcgagga    21120
aaccctgcac tacactttca gacacggctt cgtcaggcag gcctgcaaga tctccaacgt    21180
ggagctgacc aacctggtct cctgcctggg tatccttcac gagaaccgcc tggggcagac    21240
cgtgctccac tctaccctga agggcgaggc gcgtcgggac tatgtccgcg actgcatctt    21300
tctctttctc tgccacacat ggcaagcggc catgggcgtg tggcagcagt gtctcgagga    21360
cgagaacctg aaggagctgg acaaggttct tgctagaaac cttaaaaagc tgtggacggg    21420
cttcgacgag cgcaccgtcg cctcggacct ggcccagatc gtcttcccccg agcgcctgag    21480
gcagacgctg aaaggcgggc tgccagactt catgagccag agcatgatac aaaactaccg    21540
cactttcatt ctcgagcgat ctggaatgct gcccgccacc tgcaacgcct tcccctccga    21600
```

```
ctttgtcccg ctgagctacc gcgagtgtcc cccgccgctg tggagccatt gctacctctt    21660
gcagctggcc aactacatcg cctaccactc ggacgtgatc gaggacgtga gcggcgaggg    21720
gcttctcgag tgccactgcc gctgcaacct gtgctccccg caccgctccc tggtctgcaa    21780
cccccagctc ctgagcgaga cccaggtcat cggtaccttc gagctgcaag gtccgcagga    21840
gtccaccgct ccgctgaaac tcacgccggg gttgtggact tccgcgtacc tgcgcaaatt    21900
tgtacccgag gactaccacg cccatgagat aaagttcttc gaggaccaat cgcgtccgca    21960
gcacgcggat ctcacggcct gcgtcatcac ccagggcgcg atcctcgccc aattgcacgc    22020
catccaaaaa tcccgccaag agtttcttct gaaaaagggt agaggggtct acctggaccc    22080
ccagacgggc gaggtgctca acccgggtct cccccagcat gccgaggaag aagcaggagc    22140
cgctagtgga ggagatggaa gaagaatggg acagccaggc agaggaggac gaatgggagg    22200
aggagacaga ggaggaagaa ttggaagagg tggaagagga gcaggcaaca gagcagcccg    22260
tcgccgcacc atccgcgccg gcagccccgg cggtcacgga tacaacctcc gcagctccgg    22320
ccaagcctcc tcgtagatgg gatcgagtga agggtgacgg taagcacgag cggcagggct    22380
accgatcatg gagggcccac aaagccgcga tcatcgcctg cttgcaagac tgcgggggga    22440
acatcgcttt cgcccgccgc tacctgctct tccaccgcgg ggtgaacatc ccccgcaacg    22500
tgttgcatta ctaccgtcac cttcacagct aagaaaaaat cagaagtaag aggagtcgcc    22560
ggaggaggcc tgaggatcgc ggcgaacgag cccttgacca ccagggagct gaggaaccgg    22620
atcttcccca ctctttatgc cattttcag cagagtcgag gtcagcagca agagctcaaa    22680
gtaaaaaacc ggtctctgcg ctcgctcacc cgcagttgct tgtaccacaa aaacgaagat    22740
cagctgcagc gcactctcga agacgccgag gctctgttcc acaagtactg cgcgctcact    22800
cttaaagact aaggcgcgcc caccccggaaa aaaggcggga attacctcat cgccaccatg    22860
agcaaggaga ttcccacccc ttacatgtgg agctatcagc cccagatggg cctggccgcg    22920
ggcgcctccc aagactactc cacacgcatg aactggctca gtgccggccc ctcgatgatc    22980
tcacgggtca acggggtccg cagtcatcga aaccagatat tgttggagca ggcggcggtc    23040
acctccacgc ccagggcaaa gctcaacccg cgtaattggc cctccaccct ggtgtatcag    23100
gaaatccccg ggccgactac cgtactactt ccgcgtgacg cactggccga agtccgcatg    23160
actaactcag gtgtccagct ggccggcggc gcttcccggt gccgctccg cccacaatcg    23220 ggtataaaaa ccctggtgat ccgaggcaga ggcacacagc tcaacgacga gttggtgagc    23280
tcttcgatcg gtctgcgacc ggacggagtg ttccaactag ccggagccgg gagatcctcc    23340
ttcactccca accaggccta cctgaccttg cagagcagct cttcggagcc tcgctccgga    23400
ggcatcggaa ccctccagtt cgtggaggag tttgtgccct cggtctactt caacccctc    23460 tcgggatcgc caggcctcta cccggacgag ttcataccga acttcgacgc agtgagagaa    23520
gcggtggacg gctacgactg aatgtcccat ggtgactcgg ctgagctcgc tcggttgagg    23580
catctggacc actgccgccg cctgcgctgc ttcgcccggg agagctgcgg actcatctac    23640
tttgagtttc ccgaggagca ccccaacggc cctgcacacg gagtgcgaat caacgtagag    23700
ggcaccaccg agtctcacct ggtcaggttc ttcacccagc aacccttcct ggtcgagcgg    23760
gaccggggcg ccaccaccta caccgtctac tgcatctgtc ctaacccgaa gttgcatgag    23820 aattttttgct gtactctttg tggtgagttt aataaaagct gaactaagaa cctactttgg    23880
aatcccttgt cgtcatcctc gaaacaagac cgtcttcttt accaaccaga ccaaggttcg    23940
```

```
tctgaactgc acaaccaaca ggaagtacct tctctggact ttccaaaaca cctcactcgc   24000
tgttgtcaat acccgtgacg acgtcaaccc catagtcatc acccagcagt cgggcgagac   24060
caacggctgc atccactgct cctgcgaaag ccccgagtgc atctactccc tcctcaagac   24120
cctttgcgga ctccgcgacc tcctccccat gaactgatgt tgattaaaag cccaaaaacc   24180
aatcataccc ttcccccatt tccccatccc caattactca taagaataaa tcattggaac   24240
taatcattca ataagatca cttacttgaa atctgaaagt atgtctctgg tgtagttgtt   24300
cagcagcacc tcggtaccct cctcccagct ctggtactcc agtccccggc gggcggcgaa   24360
cttcctccac accttgaaag ggatgtcaaa ttcctggtcc acaattttca ttgtcttccc   24420
tctcagatga caaagaggct ccgggtggaa gatgacttca accccgtcta ccctatggc   24480 tacgcgcgga atcagaatat cccttcctc actcccccct tgtttcttc cgatggattc   24540 caaaacttcc cacccggggt attgtcactc aaactggctg acccaatagc catcgtcaat   24600
ggggatgtct cactcaaggt gggaggtgga ctcactttgc aagaaggaaa cctaactgtt   24660
gatgcaaagg ctccattgca agttgcaaat gacaacaaat tggagctttc ttatgcagac   24720
ccatttgagg ttaaagacac taagctacaa ttaaaagtag gtcatggttt aaaagtaata   24780
gatgaaaaaa cttcttcagg tcttcaaagt ctaattggaa atctcgtagt tttaacagga   24840
aaaggaattg gcactcaaga attaaaagac aaagacgatg aaactaaaaa tataggagtt   24900
ggaataaatg tgagaatagg gaaaaacgaa agtctggcgt ttgacaaaga tggaaatttg   24960
gtagcatggg ataatgaaaa cgacaggcgc actctatgga caactccaga cacatctcca   25020
aattgtaaaa taagtactga aaaagactcc aaacttactt tagtccttac taaatgcgga   25080
tctcaaattc tagcaagtgt gtctttgctt gctgtcgctg gaagttatct taatatgaca   25140
gctagtactc aaaagagtat aaaggtatct ttgatgtttg actcaaaagg gcttctaatg   25200
actacatctt ctattgataa aggatattgg aattatagaa ataaaaacag cgttgttgga   25260
actgcttatg aaaacgcaat tccatttatg ccaaatttag tggcttatcc aagacctaac   25320
acgccagact ctaaaattta tgctagaagc aaaattgttg gaaatgttta tttagcaggt   25380
ttggcttacc aaccaattgt cataacagtt agttttaatc aggagaagga tgcaagttgt   25440
gcttactcaa taacatttga atttgcctgg aacaaagact acgttggtca atttgatacc   25500
acctccttta ccttctctta tattgcccaa gaatgaaaga ccaataaacg tgtttttcat   25560
ttgaaaattt tcatgtatct ttattgattt ttacaccagc acgggtagtc agtctcccac   25620
caccagccca tttcacagtg taaacaattc tctcagcacg ggtggcctta aatagggga   25680 tgttctgatt agtgcgggaa ctgaacttgg ggtctataat ccacacagtt tcctggcgag   25740
ccaaacgggg gtcggtgatt gagatgaagc cgtcctctga aaagtcatcc aagcgggcct   25800
cgcagtccaa ggtcacagtc tggtggaatg agaagaacgc acagattcat actcggaaaa   25860
caggatgggc tgtgcctct ccatcagcgc cctcaacagt ctttgccgcc ggggctcggt   25920
gcggctgctg cagatgggat cgggatcgca agtctctctg actatgatcc ccacagcctt   25980
cagcatcagt ctcctggtgc gtcgggcaca gcaccgcatc ctgatctcgc tcatgttctc   26040
acagtaagtg cagcacataa tcaccatgtt attcagcagc ccataattca ggatgctcca   26100
gccaaagctc atgttgggga tgatggaacc cacgtgacca tcataccaga tgcggcagta   26160
tatcaggtgc ctgcccctca tgaacacact gcccatatac atgatctctt tgggcatgtt   26220
tctgttcaca atctgccggt accagggaa tcgctggttg aacatgcacc cgtaaatgac   26280
tctcctgaac cacacggcca gcagggtgcc tcccgcccga cactgcaggg agcccgggga   26340
```

```
tgaacagtgg caatgcagga tccagcgctc gtacccgctc accatctgag ctctcaccaa    26400
gtccagggta gcaggacaca ggcacactga catacatctt tttaaaattt ttatttcctc    26460
tggggacagg atcatatccc aggggactgg aaactcttgg agcagggtaa agccagcagc    26520
acatggcaat ccacggacag aacttacatt atgataatct gcatgatcac aatcgggcaa    26580
cagagggtgt tgttcagtca gagaggccct ggtctcctca tcagatcgtg gtaaacgggc    26640
cctgcgatat ggatgatggc ggagcaagct cgactgatcc tcggtttgca ttgtagtgga    26700
ttctcttgcg taccttgtcg tacttctgcc agcagaaatg ggcccttgaa cagcagatac    26760
ctctccttct cctgtctttc cgctgctgac gctcagtcat ccaactgaag tacagccatt    26820
cccgcaggtt ctcgagcagc tcctcagcat ctgatgaaac aaaagttctg tccatgcgga    26880
ttccccttaa cacatcagcc aggacattgt aggccatccc aatccagtta atgcagcctg    26940
gtctatcatt cagaggaggt gggggaagaa ctggaagaac cattttttatt ccaagcggtc    27000 tcgaaggatg ataaagtgca agtcacgcag gtgacacgt tccccgccgc tgtgctggtg    27060
gaaacagaca gccaggtcaa aacctactct attttcaagg tgctcgactg tggcttcgag    27120
cagtggctct acgcgtacat ccagcataag aatcacatta aaggctggcc ctccatcgat    27180
ttcatcaatc atcaggttac actcattcac cattcccagg taattctcat ttttccagcc    27240
ttgaattatt tctacaaatt gttggtgtaa gtccactccg cacatgtgga aaagttccca    27300
cagcgccccc tccactttca taatcaggca gaccttcata atagcaacag atctggctgc    27360
tccaccacct gcagcgtgtt caaaacaaca agattcaatg agtttctgcc ctctgccctg    27420
agctcgcgtc tcagcgtcag ctgtaaaaag tcactcaagt cctcggccac tacagatgcc    27480
aattcagagc cagggctaag cgtgggactg gcaagcgtga tggagtactt taatgctcca    27540
aagctagcac ccaaaaactg cacgctggaa taagctctct ttgtgtcacc ggtgattcct    27600
tccaaaaggt gagtgataaa gcgaggtagg tgctctctaa tcatagcagt aatggaaaag    27660
tcctctaaat aagtcactag ggccccaggg accacaatgt ggtagctgac agcgcgtcgc    27720
tcaagcatgg ttagtagaga tgagagtctg aaaaacagaa agcatgcact aaaccagagt    27780
ggcaagtctt actgaaggaa aaatcactct ctccagcagc aaagtgccca ctgggtggcc    27840
ctctcggaca tacaaaaatc gatccgtgtg gttaaagagc agcacagtta gctactgtct    27900
tctcccagca aagatcacat cggactgggt tagtatgccc ctggaatggt agtcattcaa    27960
ggccataaat ctgccttggt agccattagg aatcagcacg ctcactctca agtgaaccaa    28020
aaccacccca tgcggaggaa tgtggaaaga ttcgggggcaa aagaaattat atctattgct    28080
agtcccttcc tggacgggag cgattcctcc agggctatct atgaaagcat acagagattc    28140
agccatagct cagcccgctt accagtagac agagagcaca gcagtacaag cgccaacagc    28200
agcgactgac tacccactaa cccagctccc tatttaaagg caccttacac tgacgtaatg    28260
accaaaggtc taaaaacccc gccaaaaaaa aacacacacg ccctgggtgt ttttcgcgaa    28320
aacacttccg cgttctcact tcctcgtatc gatttcgtga ctcaacttcc gggttcccac    28380
gttacgtcac ttctgccctt acatgtaact cagccgtagg gtgccatctt gcccacgtcc    28440
aagatggctt ccatgtccgg ccacgcctcc gcggcgaccg tcagccgtgc gtcgtgacgt    28500
cactaacggt tcttgcaacg gccaatcagc gacggccccg ccctaaattc aaaagctcat    28560
ttgcatatta acttttgttt actttgtggg gtatattatt gatgatg                 28607
```

<210> SEQ ID NO 11

<211> LENGTH: 374
<212> TYPE: PRT
<213> ORGANISM: Artificial Sequence
<220> FEATURE:
<223> OTHER INFORMATION: Synthetic

<400> SEQUENCE: 11

```
Met Ala Lys Arg Leu Arg Val Glu Asp Asp Phe Asn Pro Val Tyr Pro
1               5                   10                  15

Tyr Gly Tyr Ala Arg Asn Gln Asn Ile Pro Phe Leu Thr Pro Pro Phe
                20                  25                  30

Val Ser Ser Asp Gly Phe Lys Asn Phe Pro Pro Gly Val Leu Ser Leu
            35                  40                  45

Lys Leu Ala Asp Pro Ile Thr Ile Asn Asn Gly Asp Val Ser Leu Lys
    50                  55                  60

Val Gly Gly Gly Leu Ala Val Glu Gln Gln Thr Gly Asn Leu Ser Val
65                  70                  75                  80

Asn Pro Asp Ala Pro Leu Gln Val Ala Ser Asp Lys Leu Gln Leu Ala
                85                  90                  95

Leu Ala Pro Pro Phe Glu Val Arg Asp Gly Lys Leu Ala Leu Lys Ala
                100                 105                 110

Gly Asn Gly Leu Lys Val Leu Asp Asn Ser Ile Thr Gly Leu Thr Gly
            115                 120                 125

Leu Leu Asn Thr Leu Val Val Leu Thr Gly Arg Gly Ile Gly Thr Glu
130                 135                 140

Glu Leu Lys Asn Asp Asp Gly Val Thr Asn Lys Gly Val Gly Leu Arg
145                 150                 155                 160

Val Arg Leu Gly Asp Asp Gly Gly Leu Thr Phe Asp Lys Lys Gly Asp
                165                 170                 175

Leu Val Ala Trp Asn Lys Lys Asp Asp Arg Arg Thr Leu Trp Thr Thr
                180                 185                 190

Pro Asp Thr Ser Pro Asn Cys Lys Met Ser Thr Glu Lys Asp Ser Lys
            195                 200                 205

Leu Thr Leu Thr Leu Thr Lys Cys Gly Ser Gln Val Leu Gly Asn Val
210                 215                 220

Ser Leu Leu Ala Val Thr Gly Glu Tyr His Gln Met Thr Ala Thr Thr
225                 230                 235                 240

Lys Lys Asp Val Lys Ile Ser Leu Leu Phe Asp Glu Asn Gly Ile Leu
                245                 250                 255

Leu Pro Ser Ser Ser Leu Ser Lys Asp Tyr Trp Asn Tyr Arg Ser Asp
                260                 265                 270

Asp Ser Ile Val Ser Gln Lys Tyr Asn Asn Ala Val Pro Phe Met Pro
            275                 280                 285

Asn Leu Thr Ala Tyr Pro Lys Pro Ser Ala Gln Asn Ala Lys Asn Tyr
290                 295                 300

Ser Arg Thr Lys Ile Ile Ser Asn Val Tyr Leu Gly Ala Leu Thr Tyr
305                 310                 315                 320

Gln Pro Val Ile Ile Thr Ile Ala Phe Asn Gln Glu Thr Glu Asn Gly
                325                 330                 335

Cys Ala Tyr Ser Ile Thr Phe Phe Thr Trp Gln Lys Asp Tyr Ser
            340                 345                 350

Ala Gln Gln Phe Asp Val Thr Ser Phe Thr Phe Ser Tyr Leu Thr Gln
            355                 360                 365

Glu Asn Lys Asp Lys Asp
    370
```

<210> SEQ ID NO 12
<211> LENGTH: 177
<212> TYPE: DNA
<213> ORGANISM: Artificial Sequence
<220> FEATURE:
<223> OTHER INFORMATION: Synthetic

<400> SEQUENCE: 12

```
atggccaccc cctcgatgat gccgcagtgg gcgtacatgc acatcgccgg gcaggacgcc      60
tcggagtacc tgagcccggg tctggtgcag tttgcccgcg ccaccgacac gtacttcagc     120
ctgggcaaca agtttaggaa ccccacggtg gctcccaccc acgatgtgac cacggac       177
```

<210> SEQ ID NO 13
<211> LENGTH: 1590
<212> TYPE: DNA
<213> ORGANISM: Artificial Sequence
<220> FEATURE:
<223> OTHER INFORMATION: Synthetic

<400> SEQUENCE: 13

```
cggtcccagc gtctgacgct gcgcttcgtg cccgtggatc gcgaggacac cacgtactcg      60
tacaaggcgc gcttcactct ggccgtggga gacaaccggg tgctagacat ggccagcact     120
tactttgaca tccgcggcgt cctggaccgc ggtcccagct tcaaacccta ctcgggcacg     180
gcttacaaca gcctggcccc caagagcgct cccaatccca gccagtggga tgcaaaggaa     240
aaggaaggag ttgcccaaac agaaaaaaat gttttaaaaa catttggtgt tgccgctaca     300
ggtggtttta atattacaga tcagggtttg ttacttggaa ctgaggaaac agctgaaaac     360
gttaaaaagg atatctatgc agagaaaact ttccagcctg aacctcaagt tggtgaagaa     420
aactggcagg aaagtgaagc ttttatgga ggaagggcta ttaagaaga caccaaaatg      480 aagccatgct atggttcatt tgccagaccc actaatgaaa aaggaggaca ggctaaattt     540
aaaacactag atgggcaagt tacaaaagat ccagatattg actttgctta ctttgacgtc     600
cctggcggaa aagctccaac aggcagtagt ctaccggaag aatacaaagc agatataatt     660
ttgtacacag aaaatgttaa tctggaaaca ccagatactc acatagtgta taaacctggc     720
aaagaagatg acaattctga aattaactta acacaacagt ccatgccaaa cagacccaac     780
tacattggct ttagggacaa cttttgtaggt ctcatgtact acaacagtac tggcaacatg     840
ggtgtgctgg ctggtcaggc ctctcagttg aatgctgtgg tggacttgca agacagaaac     900
accgagctgt cttaccagct cttgctagat tctctgggtg acagaaccag atactttagc     960
atgtggaact ctgcggttga cagttatgat cccgatgtca ggatcattga aatcacggt      1020 gtggaagatg aacttccaaa ctattgcttc ccattgaatg gcactggtac caattccacc     1080
tatcaaggtg taaaaattac aggtaataat gatggcgatc ttgaaaccga atgggaaaga     1140
gatgaagcaa tctctagaca aaaccaaatc tgcaagggca acgtctatgc catggagatc     1200
aacctccagg ccaacctgtg gaagagtttt ctgtactcga acgtagccct gtacctgcct     1260
gactcataca gtacacgcc ggccaacgtc acgctgcccg ccaacaccaa cacctacgag     1320
tacatgaacg gccgcgtggt agcccccctcg ctggtggacg cttacatcaa catcggcgcc     1380
cgctggtcgc tggatcccat ggacaatgta aacccattca accaccaccg caacgcgggc     1440
ctgcgctacc gttccatgtt gttgggcaac ggtcgctacg tgcccttcca catccaagtg     1500
ccccaaaagt tctttgccat caagaacctg cttctgctcc cgggctccta cacctacgag     1560
```

| | |
|---|---:|
| tggaacttcc gcaaggacgt caacatgatc | 1590 |

<210> SEQ ID NO 14
<211> LENGTH: 1083
<212> TYPE: DNA
<213> ORGANISM: Artificial Sequence
<220> FEATURE:
<223> OTHER INFORMATION: Synthetic

<400> SEQUENCE: 14

| | |
|---|---:|
| ctgcagagtt ccctcggaaa cgatctgcgc gtcgacggcg cctccgtccg cttcgacagc | 60 |
| gtcaacctct acgccacctt cttccccatg gcgcacaaca ccgcctccac cctggaagcc | 120 |
| atgctgcgca acgacaccaa cgaccagtcc ttcaacgact acctctcggc cgccaacatg | 180 |
| ctctacccca tcccggccaa ggccaccaac gtgcccatct ccatcccctc acgcaactgg | 240 |
| gccgccttcc gcggctggag tttcaccagg ctcaagacca aggaaactcc ctcgctaggc | 300 |
| tcgggtttcg acccatactt tgtctactcg ggctccatcc cctatctcga cgggaccttc | 360 |
| tacctcaatc acaccttcaa gaaggtctcc atcatgttcg actcctcggt cagctggccc | 420 |
| ggcaacgacc ggctgctcac gccgaacgag ttcgagatca agcgcagcgt cgacggggag | 480 |
| ggctacaacg tggcccaatg caacatgacc aaggactggt cctcgtccca gatgctctcc | 540 |
| cactacaaca tcggctacca gggcttccac gtgcccgagg gctacaagga ccgcatgtac | 600 |
| tccttcttcc gcaacttcca gcccatgagc aaggcaggtg gtcgatgagat caactacaag | 660 |
| gactacaagg ccgtcaccct gcccttccag cacaacaact cgggcttcac cggctacctc | 720 |
| gcacccacca tgcgtcaggg gcagccctac cccgccaact tcccctaccc gctcatcggc | 780 |
| cagacagccg tgccctccgt cacccagaaa agttcctct gcgacagggt catgtggcgc | 840 |
| atccccttct ccagcaactt catgtccatg ggcgccctca ccgacctggg tcagaacatg | 900 |
| ctctacgcca actcggccca tgcgctcgac atgaccttcg aggtggaccc catggatgag | 960 |
| cccacccctcc tctatcttct cttcgaagtt ttcgacgtgg tcagagtgca ccagccgcac | 1020 |
| cgcggcgtca tcgaggccgt ctacctgcgc acgcccttct ccgccggaaa cgccaccaca | 1080 |
| taa | 1083 |

<210> SEQ ID NO 15
<211> LENGTH: 2850
<212> TYPE: DNA
<213> ORGANISM: Artificial Sequence
<220> FEATURE:
<223> OTHER INFORMATION: Synthetic

<400> SEQUENCE: 15

| | |
|---|---:|
| atggccaccc cctcgatgat gccgcagtgg gcgtacatgc acatcgccgg gcaggacgcc | 60 |
| tcggagtacc tgagcccggg tctggtgcag tttgcccgcg ccaccgacac gtacttcagc | 120 |
| ctgggcaaca gtttaggaa ccccacggtg gctcccaccc acgatgtgac cacgaccgg | 180 |
| tcccagcgtc tgacgctgcg cttcgtgccc gtggatcgcg aggacaccac gtactcgtac | 240 |
| aaggcgcgct tcactctggc cgtgggagac aaccgggtgc tagacatggc cagcacttac | 300 |
| tttgacatcc gcgcgtcct ggaccgcggt cccagcttca aaccctactc gggcacggct | 360 |
| tacaacagcc tggcccccaa gagcgctccc aatcccagcc agtgggatgc aaaggaaaag | 420 |
| gaaggagttg cccaaacaga aaaaatgtt ttaaaaacat tggtgttgc cgctacaggt | 480 |
| ggttttaata ttacagatca gggttgtta cttggaactg aggaaacagc tgaaaacgtt | 540 |
| aaaaaggata tctatgcaga gaaaactttc cagcctgaac ctcaagttgg tgaagaaaac | 600 |

```
tggcaggaaa gtgaagcctt ttatggagga agggctatta agaaagacac caaaatgaag    660
ccatgctatg gttcatttgc cagacccact aatgaaaaag gaggacaggc taaatttaaa    720
acactagatg ggcaagttac aaaagatcca gatattgact ttgcttactt tgacgtccct    780
ggcggaaaag ctccaacagg cagtagtcta ccggaagaat acaaagcaga tataattttg    840
tacacagaaa atgttaatct ggaaacacca gatactcaca tagtgtataa acctggcaaa    900
gaagatgaca attctgaaat taacttaaca caacagtcca tgccaaacag acccaactac    960
attggcttta gggacaactt tgtaggtctc atgtactaca acagtactgg caacatgggt   1020
gtgctggctg tcaggcctc tcagttgaat gctgtggtgg acttgcaaga cagaaacacc    1080
gagctgtctt accagctctt gctagattct ctgggtgaca gaaccagata ctttagcatg   1140
tggaactctg cggttgacag ttatgatccc gatgtcagga tcattgagaa tcacggtgtg   1200
gaagatgaac ttccaaacta ttgcttccca ttgaatggca ctggtaccaa ttccacctat   1260
caaggtgtaa aaattacagg taataatgat ggcgatcttg aaaccgaatg ggaaagagat   1320
gaagcaatct ctagacaaaa ccaaatctgc aagggcaacg tctatgccat ggagatcaac   1380
ctccaggcca acctgtggaa gagttttctg tactcgaacg tagccctgta cctgcctgac   1440
tcatacaagt acacgccggc caacgtcacg ctgcccgcca acaccaacac ctacgagtac   1500
atgaacggcc gcgtggtagc cccctcgctg gtggacgctt acatcaacat cggcgcccgc   1560
tggtcgctgg atcccatgga caatgtaaac ccattcaacc accaccgcaa cgcgggcctg   1620
cgctaccgtt ccatgttgtt gggcaacggt cgctacgtgc ccttccacat ccaagtgccc   1680
caaaagttct ttgccatcaa gaacctgctt ctgctcccgg gctcctacac ctacgagtgg   1740
aacttccgca aggacgtcaa catgatcctg cagagttccc tcggaaacga tctgcgcgtc   1800
gacggcgcct ccgtccgctt cgacagcgtc aacctctacg ccaccttctt ccccatggcg   1860
cacaacaccg cctccaccct ggaagccatg ctgcgcaacg acaccaacga ccagtccttc   1920
aacgactacc tctcggccgc caacatgctc taccccatcc cggccaaggc caccaacgtg   1980
cccatctcca tccccctcac gcaactgggc gccttccgcg gctggagttt caccaggctc   2040
aagaccaagg aaaactccct gctaggctcg ggtttcgacc catactttgt ctactcgggc   2100
tccatcccct atctcgacgg gaccttctac ctcaatcaca ccttcaagaa ggtctccatc   2160
atgttcgact cctcggtcag ctggcccggc aacgaccggc tgctcacgcc gaacgagttc   2220
gagatcaagc gcagcgtcga cggggagggc tacaacgtgg cccaatgcaa catgaccaag   2280
gactggttcc tcgtccagat gctctcccac tacaacatcg gctaccaggg cttccacgtg   2340
cccgagggct acaaggaccg catgtactcc ttcttccgca acttccagcc catgagcagg   2400
caggtggtcg atgagatcaa ctacaaggac tacaaggccg tcaccctgcc cttccagcac   2460
aacaactcgg gcttcaccgg ctacctcgca cccaccatgc gtcaggggca ccctaccccc   2520
gccaacttcc cctacccgct catcggccag acagccgtgc cctccgtcac ccagaaaaag   2580
ttcctctgcg acagggtcat gtggcgcatc cccttctcca gcaacttcat gtccatgggc   2640
gccctcaccg acctgggtca gaacatgctc tacgccaact cggcccatgc gctcgacatg   2700
accttcgagg tggaccccat ggatgagccc accctcctct atcttctctt cgaagttttc   2760
gacgtggtca gagtgcacca gccgcaccgc ggcgtcatcg aggccgtcta cctgcgcacg   2820
cccttctccg ccggaaacgc caccacataa                                     2850
```

<210> SEQ ID NO 16

```
<211> LENGTH: 135
<212> TYPE: DNA
<213> ORGANISM: Artificial Sequence
<220> FEATURE:
<223> OTHER INFORMATION: Synthetic

<400> SEQUENCE: 16
atgacaaaga ggctccgggt ggaagatgac ttcaaccccg tctacccta tggctacgcg      60 cggaatcaga atatcccctt cctcactccc ccctttgttt cttccgatgg attccaaaac     120
ttcccacccg gggta                                                      135

<210> SEQ ID NO 17
<211> LENGTH: 429
<212> TYPE: DNA
<213> ORGANISM: Artificial Sequence
<220> FEATURE:
<223> OTHER INFORMATION: Synthetic

<400> SEQUENCE: 17
ttgtcactca aactggctga cccaatagcc atcgtcaatg gggatgtctc actcaaggtg      60
ggaggtggac tcactttgca agaaggaaac ctaactgttg atgcaaaggc tccattgcaa     120
gttgcaaatg acaacaaatt ggagctttct tatgcagacc catttgaggt taaagacact     180
aagctacaat aaaagtagg tcatggttta aaagtaatag atgaaaaac ttcttcaggt       240 cttcaaagtc taattggaaa tctcgtagtt ttaacaggaa aaggaattgg cactcaagaa     300
ttaaaagaca agacgatga aactaaaaat ataggagttg aataaatgt gagaataggg       360 aaaaacgaaa gtctggcgtt tgacaaagat ggaaatttgg tagcatggga taatgaaaac     420
gacaggcgc                                                             429

<210> SEQ ID NO 18
<211> LENGTH: 546
<212> TYPE: DNA
<213> ORGANISM: Artificial Sequence
<220> FEATURE:
<223> OTHER INFORMATION: Synthetic

<400> SEQUENCE: 18
actctatgga caactccaga cacatctcca aattgtaaaa taagtactga aaaagactcc      60
aaacttactt tagtccttac taaatgcgga tctcaaattc tagcaagtgt gtctttgctt     120
gctgtcgctg gaagttatct taatatgaca gctagtactc aaaagagtat aaaggtatct     180
ttgatgtttg actcaaaagg gcttctaatg actacatctt ctattgataa aggatattgg     240
aattatagaa ataaaaacag cgttgttgga actgcttatg aaaacgcaat tccatttatg     300
ccaaatttag tggcttatcc aagacctaac acgccagact ctaaaattta tgctagaagc     360
aaaattgttg gaaatgttta tttagcaggt ttggcttacc aaccaattgt cataacagtt     420
agttttaatc aggagaagga tgcaagttgt gcttactcaa taacatttga atttgcctgg     480
aacaaagact acgttggtca atttgatacc acctccttta ccttctccta tatcgcccaa     540
gaatga                                                                546

<210> SEQ ID NO 19
<211> LENGTH: 1110
<212> TYPE: DNA
<213> ORGANISM: Artificial Sequence
<220> FEATURE:
<223> OTHER INFORMATION: Synthetic

<400> SEQUENCE: 19
```

```
atgacaaaga ggctccgggt ggaagatgac ttcaaccccg tctacccta tggctacgcg    60 cggaatcaga atatcccctt cctcactccc ccctttgttt cttccgatgg attccaaaac   120
ttcccacccg gggtattgtc actcaaactg gctgacccaa tagccatcgt caatggggat   180
gtctcactca aggtgggagg tggactcact ttgcaagaag aaacctaac tgttgatgca    240 aaggctccat tgcaagttgc aaatgacaac aaattggagc tttcttatgc agacccattt   300
gaggttaaag acactaagct acaattaaaa gtaggtcatg gtttaaaagt aatagatgaa   360
aaaacttctt caggtcttca aagtctaatt ggaaatctcg tagttttaac aggaaaagga   420
attggcactc aagaattaaa agacaaagac gatgaaacta aaaatatagg agttggaata   480
aatgtgagaa tagggaaaaa cgaaagtctg gcgtttgaca agatggaaa tttggtagca    540 tgggataatg aaaacgacag gcgcactcta tggacaactc cagacacatc tccaaattgt   600
aaaataagta ctgaaaaaga ctccaaactt actttagtcc ttactaaatg cggatctcaa   660
attctagcaa gtgtgtcttt gcttgctgtc gctggaagtt atcttaatat gacagctagt   720
actcaaaaga gtataaaggt atctttgatg tttgactcaa aagggcttct aatgactaca   780
tcttctattg ataaaggata ttggaattat agaaataaaa acagcgttgt tggaactgct   840
tatgaaaacg caattccatt tatgccaaat ttagtggctt atccaagacc taacacgcca   900
gactctaaaa tttatgctag aagcaaaatt gttggaaatg tttatttagc aggtttggct   960
taccaaccaa ttgtcataac agttagtttt aatcaggaga aggatgcaag ttgtgcttac  1020
tcaataacat ttgaatttgc ctggaacaaa gactacgttg gtcaatttga taccacctcc  1080
tttaccttct cctatatcgc ccaagaatga                                    1110

<210> SEQ ID NO 20
<211> LENGTH: 135
<212> TYPE: DNA
<213> ORGANISM: Artificial Sequence
<220> FEATURE:
<223> OTHER INFORMATION: Synthetic

<400> SEQUENCE: 20
atgacaaaga ggctccgggt ggaagatgac ttcaaccccg tctacccta tggctacgcg    60 cggaatcaga atatcccctt cctcactccc ccctttgttt cttccgatgg attccaaaac   120
ttcccacctg gggtc                                                    135

<210> SEQ ID NO 21
<211> LENGTH: 405
<212> TYPE: DNA
<213> ORGANISM: Artificial Sequence
<220> FEATURE:
<223> OTHER INFORMATION: Synthetic

<400> SEQUENCE: 21
ctgtcactca aactggctga cccaatcacc atcgctaatg ggatgtctc actcaagttg     60 ggaggcggac tgacggtgga aaaagagtct ggaaacttaa ctgtgaaccc taaggctccc   120
ttgcaagttg caagtggaca attggaatta gcatatgatt ctccatttga tgttaaaaac   180
aatatgctta ctcttaaagc aggtcacggc ttagcagtta taacgaaaga caatactgat   240
ttacaaccac taatgggcac acttgttgtt ttaactggca aaggcattgg cactggcaca   300
agtgctcacg gtgaaccat agatgtgaga ataggaaaaa acggaagtct ggcatttgac    360
aaaaatggag atttggtggc ctgggataaa gaaaatgaca ggcgc                   405
```

<210> SEQ ID NO 22
<211> LENGTH: 567
<212> TYPE: DNA
<213> ORGANISM: Artificial Sequence
<220> FEATURE:
<223> OTHER INFORMATION: Synthetic

<400> SEQUENCE: 22

| | | | | | |
|---|---|---|---|---|---|
| actctatgga | caactccaga | cacatctcca | aattgcaaaa | tgagtgaagt | caaagactca | 60 |
| aagcttactc | ttattcttac | aaaatgcgga | agtcaaattc | taggaagtgt | atctttgctt | 120 |
| gctgtaaaag | gagaatatca | aaatatgact | gccagtacta | ataagaatgt | aaaaataaca | 180 |
| ctgctatttg | atgctaatgg | agtcttgtta | gaaggatcca | gtcttgataa | agagtactgg | 240 |
| aactttagaa | acaatgattc | tactgtgtct | ggaaaatatg | aaaatgctgt | tccgttcatg | 300 |
| cctaacataa | cagcttataa | acccgtcaat | tctaaaagct | atgccagaag | tcacatattt | 360 |
| ggaaatgtat | atattgatgc | taagccatat | aatccagtgg | ttattaaaat | tagcttcaat | 420 |
| caagagacac | aatgtgattg | ccgcggtgat | tgttttttgta | acaattgtgt | ctattctata | 480 |
| tcatttgact | acacttgctc | taaagagtat | acaggtatgc | aattcgatgt | tacatctttc | 540 |
| accttctcct | atatcgccca | agaatga | | | | 567 |

<210> SEQ ID NO 23
<211> LENGTH: 1107
<212> TYPE: DNA
<213> ORGANISM: Artificial Sequence
<220> FEATURE:
<223> OTHER INFORMATION: Synthetic

<400> SEQUENCE: 23

| | | | | | |
|---|---|---|---|---|---|
| atgacaaaga | ggctccgggt | ggaagatgac | ttcaaccccg | tctacccta | tggctacgcg | 60 |
| cggaatcaga | atatcccctt | cctcactccc | ccctttgttt | cttccgatgg | attccaaaac | 120 |
| ttcccacctg | gggtcctgtc | actcaaactg | gctgacccaa | tcaccatcgc | taatggggat | 180 |
| gtctcactca | agttgggagg | cggactgacg | gtggaaaaag | agtctggaaa | cttaactgtg | 240 |
| aaccctaagg | ctcccttgca | agttgcaagt | ggacaattgg | aattagcata | tgattctcca | 300 |
| tttgatgtta | aaacaatat | gcttactctt | aaagcaggtc | acggcttagc | agttgtaacg | 360 |
| aaagacaata | ctgatttaca | accactaatg | ggcacacttg | ttgttttaac | tggcaaaggc | 420 |
| attggcactg | gcacaagtgc | tcacggtgga | accatagatg | tgagaatagg | aaaaaacgga | 480 |
| agtctggcat | ttgacaaaaa | tggagatttg | gtggcctggg | ataaagaaaa | tgacaggcgc | 540 |
| actctatgga | caactccaga | cacatctcca | aattgcaaaa | tgagtgaagt | caaagactca | 600 |
| aagcttactc | ttattcttac | aaaatgcgga | agtcaaattc | taggaagtgt | atctttgctt | 660 |
| gctgtaaaag | gagaatatca | aaatatgact | gccagtacta | ataagaatgt | aaaaataaca | 720 |
| ctgctatttg | atgctaatgg | agtcttgtta | gaaggatcca | gtcttgataa | agagtactgg | 780 |
| aactttagaa | acaatgattc | tactgtgtct | ggaaaatatg | aaaatgctgt | tccgttcatg | 840 |
| cctaacataa | cagcttataa | acccgtcaat | tctaaaagct | atgccagaag | tcacatattt | 900 |
| ggaaatgtat | atattgatgc | taagccatat | aatccagtgg | ttattaaaat | tagcttcaat | 960 |
| caagagacac | aatgtgattg | ccgcggtgat | tgttttttgta | acaattgtgt | ctattctata | 1020 |
| tcatttgact | acacttgctc | taaagagtat | acaggtatgc | aattcgatgt | tacatctttc | 1080 |
| accttctcct | atatcgccca | agaatga | | | | 1107 |

-continued

```
<210> SEQ ID NO 24
<211> LENGTH: 405
<212> TYPE: DNA
<213> ORGANISM: Artificial Sequence
<220> FEATURE:
<223> OTHER INFORMATION: Synthetic

<400> SEQUENCE: 24
ctgtcactca aactggctga cccaatcacc atcgctaatg␣ gggatgtctc␣ actcaagttg      60 ggaggcggac tgacggtgga aaaagagtct ggaaacttaa␣ ctgtgaaccc␣ taaggctccc    120 ttgcaagttg caagtggaca attggaatta gcatatgatt␣ ctccatttga␣ tgttaaaaac    180 aatatgctta ctcttaaagc aggtcacggc ttagcagttg␣ taacgaaaga␣ caatactgat    240 ttacaaccac taatgggcac acttgttgtt␣ taactggca␣ aaggcattgg␣ cactggcaca    300 agtgctcacg gtggaaccat agatgtgaga␣ ataggaaaaa␣ acggaagtct␣ ggcatttgac    360 aaaaatggag atttggtggc␣ ctgggataaa␣ gaaaatgaca␣ ggcgc                   405

<210> SEQ ID NO 25
<211> LENGTH: 567
<212> TYPE: DNA
<213> ORGANISM: Artificial Sequence
<220> FEATURE:
<223> OTHER INFORMATION: Synthetic

<400> SEQUENCE: 25
actctatgga caactccaga cacatctcca aattgcaaaa␣ tgagtgaagt␣ caaagactca     60 aagcttactc ttattcttac aaaatgcgga agtcaaattc␣ taggaagtgt␣ atctttgctt    120 gctgtaaaag gagaatatca aaatatgact gccagtacta␣ ataagaatgt␣ aaaaataaca    180 ctgctatttg atgctaatgg agtcttgtta gaaggatcca␣ gtcttgataa␣ agagtactgg    240 aactttagaa acaatgattc tactgtgtct ggaaaatatg␣ aaaatgctgt␣ tccgttcatg    300 cctaacataa cagcttataa acccgtcaat␣ tctaaaagct␣ atgccagaag␣ tcacatattt    360 ggaaatgtat atattgatgc taagccatat aatccagtgg␣ ttattaaaat␣ tagcttcaat    420 caagagacac aatgtgattg ccgcggtgat tgtttttgta␣ acaattgtgt␣ ctattctata    480 tcatttgact acacttgctc taaagagtat␣ acaggtatgc␣ aattcgatgt␣ tacatctttc    540 accttctcct atatcgccca agaatga                                          567

<210> SEQ ID NO 26
<211> LENGTH: 1107
<212> TYPE: DNA
<213> ORGANISM: Artificial Sequence
<220> FEATURE:
<223> OTHER INFORMATION: Synthetic

<400> SEQUENCE: 26
atgacaaaga ggctccgggt ggaagatgac ttcaaccccg␣ tctaccccta␣ tggctacgcg     60 cggaatcaga atatcccctt cctcactccc␣ ccctttgttt␣ cttccgatgg␣ attccaaaac    120 ttcccacctg gggtcctgtc actcaaactg gctgacccaa␣ tcaccatcgc␣ taatggggat    180 gtctcactca agttgggagg cggactgacg gtggaaaaag␣ agtctggaaa␣ cttaactgtg    240 aaccctaagg ctcccttgca agttgcaagt ggacaattgg␣ aattagcata␣ tgattctcca    300 tttgatgtta aaaacaatat␣ gcttactctt aaagcaggtc␣ acggcttagc␣ agttgtaacg    360 aaagacaata ctgatttaca accactaatg␣ gcacacttg␣ ttgttttaac␣ tggcaaaggc    420 attggcactg gcacaagtgc tcacggtgga accatagatg␣ tgagaatagg␣ aaaaacgga    480
```

```
agtctggcat ttgacaaaaa tggagatttg gtggcctggg ataaagaaaa tgacaggcgc     540
actctatgga caactccaga cacatctcca aattgcaaaa tgagtgaagt caaagactca     600
aagcttactc ttattcttac aaaatgcgga agtcaaattc taggaagtgt atctttgctt     660
gctgtaaaag gagaatatca aaatatgact gccagtacta ataagaatgt aaaaataaca     720
ctgctatttg atgctaatgg agtcttgtta gaaggatcca gtcttgataa agagtactgg     780
aactttagaa acaatgattc tactgtgtct ggaaaatatg aaaatgctgt tccgttcatg     840
cctaacataa cagcttataa acccgtcaat tctaaaagct atgccagaag tcacatattt     900
ggaaatgtat atattgatgc taagccatat aatccagtgg ttattaaaat tagcttcaat     960
caagagacac aatgtgattg ccgcggtgat tgtttttgta acaattgtgt ctattctata    1020
tcatttgact acacttgctc taaagagtat acaggtatgc aattcgatgt tacatctttc    1080
accttctcct atatcgccca agaatga                                        1107

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Cys Asp Cys Arg Gly Asp Cys Phe Cys
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic

<400> SEQUENCE: 28

Lys Lys Lys Lys Lys Lys Lys
1               5
```

ADENOVECTORS FOR DELIVERY OF THERAPEUTIC GENETIC MATERIAL INTO T CELLS

CROSS-REFERENCE TO RELATED APPLICATIONS

This patent application is the U.S. National Phase of PCT/US2017/054397, filed Sep. 29, 2017, which claims the benefit of U.S. Provisional Patent Application No. 62/402,755, filed Sep. 30, 2016, which are incorporated by reference in their entirety.

SEQUENCE LISTING

Incorporated by reference in its entirety herein is a nucleotide/amino acid sequence listing submitted concurrently herewith and identified as follows: One 90,586 Byte ASCII (Text) file named "742385_ST25.txt," created on Mar. 29, 2019.

BACKGROUND OF THE INVENTION

Delivering therapeutic genetic material into primary T cells is a valuable approach to engineer more potent immune effector T cells to treat cancer and infectious disease indications, or repair a T cell immunodeficiency genetic disorder. Such therapeutic transgenes introduced into T cells can enable them to perform new functions to address unmet medical needs.

Several means are commonly used to transduce therapeutic genetic material into T expanded/activated cells: retrovector, lentivector, adenovector, and a vast array of nanoparticles. The use of lentivectors is the standard approach in the field, but has many disadvantages. For example, since lentivectors are incorporated into the genome of the targeted cell, the expression of the therapeutic genetic material is very long-lasting and can result in on-target off-tumor toxicities. mRNA electroporation is an alternative to lentivectors which avoids the on-target off-tumor toxicities, but the number of T cell injections to reach efficacy is extremely high.

It has been shown that a chimeric adenovector Ad5F35, corresponding to an Ad5 vector displaying a F35 knob, can be transduced into dividing CD4 and CD8 T cells. However, only a fraction of T cells, which were activated by either phytohemagluttinin or anti-CD3 and CD28 costimulation for 3 to 15 days, ended up transduced by this Ad5F35 chimeric vector when administered at reasonable adenoviral vector doses.

Thus, there is a desire for vectors with higher levels of transduction efficiency to support high quality production of engineered therapeutic T cells.

BRIEF SUMMARY OF THE INVENTION

The invention provides a serotype 28 adenoviral vector comprising (i) at least a portion of an adenovirus serotype 26 fiber protein in place of at least a portion of a corresponding endogenous serotype 28 fiber protein and (ii) an exogenous nucleic acid sequence.

The invention provides a serotype 28 adenoviral vector comprising (i) a fiber protein containing a high affinity RGD ligand and (ii) an exogenous nucleic acid sequence.

The invention also provides cells (e.g., T cells) comprising the vectors and compositions (e.g., pharmaceutical compositions) comprising the vectors or cells.

Additionally, the invention provides a method of transducing T cells comprising contacting the T cells with (a) a serotype 28 adenoviral vector comprising at least a portion of an adenovirus serotype 26 fiber protein in place of at least a portion of a corresponding endogenous serotype 28 fiber protein and an exogenous nucleic acid sequence; (b) a serotype 28 adenoviral vector comprising a fiber protein containing a high affinity RGD ligand and an exogenous nucleic acid sequence; (c) a serotype 28 adenoviral vector comprising at least a portion of an adenovirus serotype 45 hexon protein in place of at least a portion of a corresponding endogenous serotype 28 hexon protein an exogenous nucleic acid sequence; (d) a serotype 28 adenoviral vector comprising at least a portion of an adenovirus serotype 45 fiber protein in place of at least a portion of a corresponding endogenous serotype 28 fiber protein and an exogenous nucleic acid sequence; (e) a serotype 28 adenoviral vector comprising at least a portion of an adenovirus serotype 45 hexon protein in place of at least a portion of a corresponding endogenous serotype 28 hexon protein, at least a portion of an adenovirus serotype 45 fiber protein in place of at least a portion of a corresponding endogenous serotype 28 fiber protein, and an exogenous nucleic acid sequence; or (f) a serotype 35 adenoviral vector comprising an exogenous nucleic acid sequence, thereby transducing T cells with the vector.

BRIEF DESCRIPTION OF THE SEVERAL VIEWS OF THE DRAWINGS

FIG. 1 is a table summarizing the results of experiments to identify T cell transducing adenoviral vectors. The GFP expressing vectors were evaluated for transduction of T cells using a UV microscope to determine a relative transduction score. A ++ relative transduction score was given to the Ad5 sample at day 1 post transduction and all other observations were compared to this initial benchmark. An observation of GFP positive cells above the Ad5 percentage was given as +++ or ++++ depending on GFP expression levels. An observation below the Ad5 transduction level was given a + or zero dependent on results observed.

FIG. 2 is a table summarizing the results of experiments to quantify the level of T cell transduction of adenoviral vectors using flow cytometry. T cells were transduced with GFP-expressing adenoviral vectors, and GFP expression was measured with a BD FACS Canto II instrument and the data were analyzed by using FlowJo software.

FIG. 3 is a table summarizing the results of experiments analyzing T cell viability and density 48 hours after infection with the adenoviral vectors.

FIG. 4 is a table summarizing the results of experiments to determine the optimal multiplicity of infection (MOI) of the luciferase-expressing adenoviral vectors. T cells were transduced with luciferase-expressing adenoviral vectors in duplicate at the indicated MOI. The T cells were harvested 48 hours after transduction and transduction level was determined based on the relative luciferase units detected.

FIG. 5 is a table summarizing the results of experiments to determine the optimal MOI of the GFP-expressing adenoviral vectors. T cells were transduced with GFP expressing adenoviral vectors in duplicate at the indicated MOI. The T cells were harvested 48 hours after transduction and transduction level was determined by GFP expression using flow cytometry. GFP expression was measured with a BD FACS Canto II instrument and the data were analyzed by using FlowJo software.

FIG. 6 is a table summarizing the results of experiments to determine the optimal MOI of the GFP-expressing adenoviral vectors. T cells were transduced with GFP expressing adenoviral vectors in duplicate at the indicated MOI. The T cells were harvested 48 hours after transduction and analyzed for cell viability, cell density and GFP expression. Adenoviral transduction level was determined by GFP expression using flow cytometry measured with a BD FACS Canto II instrument and the data were analyzed by using FlowJo software.

DETAILED DESCRIPTION OF THE INVENTION

Figure 7:
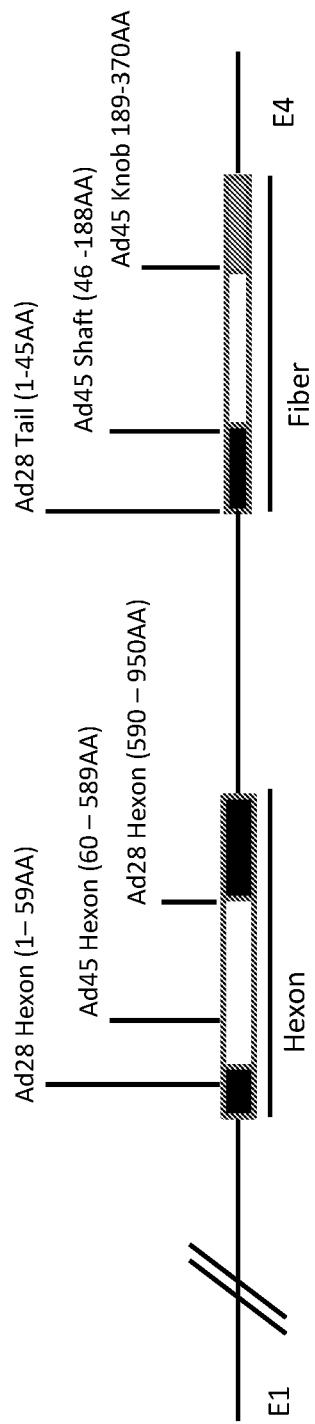
FIG. 7 is a schematic of a serotype 28 adenoviral (Ad28) vector comprising (i) a portion of a serotype 45 adenoviral (Ad45) hexon protein in place of a portion of a corresponding endogenous Ad28 hexon protein and (ii) a portion of an Ad45 fiber protein in place of a portion of a corresponding endogenous Ad28 fiber protein. The Ad28/Ad45 hexon protein is encoded by the nucleic acid sequence of SEQ ID NO: 15. The Ad28/Ad45 fiber protein is encoded by the nucleic acid sequence of SEQ ID NO: 19.

The invention provides adenoviral vector compositions that have high transduction efficiencies into ex vivo stimulated and dividing human primary T cells, and have optimal transgene expression for engineered T cells. The transgene desirably is chimeric antigen receptor (CAR) capable of recognizing cancer and/or infected cells and mediating the death of the cells.

Since adenoviral vectors do not integrate into the genome of cells, the integrating vector-related effects observed with lentiviral vectors, such as chromosomal positional effects (i.e., insertion of an external strong promoter/enhancer at the vicinity of proto-oncogenes) and the risk of endogenous gene disruption (i.e., insertional mutagenesis) are not observed. Additionally, on-target off-tumor effects (i.e., the targeting of healthy tissue) is reduced relative to lentiviral vectors.

In a first embodiment, the adenoviral vector is a serotype 28 adenoviral vector comprising (i) at least a portion of an adenovirus serotype 26 fiber protein in place of at least a portion of a corresponding endogenous serotype 28 fiber protein and (ii) an exogenous nucleic acid sequence.

In a second embodiment, the adenoviral vector is a serotype 28 adenoviral vector comprising (i) a fiber protein containing a high affinity RGD ligand and (ii) an exogenous nucleic acid sequence.

In a third embodiment, the adenoviral vector is a serotype 28 adenoviral vector comprising an exogenous nucleic acid sequence and one of (i)-(iii): (i) at least a portion of an adenovirus serotype 45 hexon protein in place of at least a portion of a corresponding endogenous serotype 28 hexon protein; (ii) at least a portion of an adenovirus serotype 45 fiber protein in place of at least a portion of a corresponding endogenous serotype 28 fiber protein, or (iii) at least a portion of an adenovirus serotype 45 hexon protein in place of at least a portion of a corresponding endogenous serotype 28 hexon protein and at least a portion of an adenovirus serotype 45 fiber protein in place of at least a portion of a corresponding endogenous serotype 28 fiber protein.

In a fourth embodiment, the adenoviral vector is a serotype 35 adenoviral vector comprising an exogenous nucleic acid sequence.

The term "adenoviral vector," as used herein, refers to an adenovirus in which the adenoviral genome has been manipulated to accommodate a nucleic acid sequence that is non-native (i.e., exogenous) with respect to the adenoviral genome. Adenovirus is a medium-sized (90-100 nm), non-enveloped icosohedral virus containing approximately 36 kb of double-stranded DNA. There are 49 human adenoviral serotypes, categorized into 6 subgenera (A through F) based on nucleic acid comparisons, fiber protein characteristics, and biological properties (Crawford-Miksza et al., *J. Virol.,* 70: 1836-1844 (1996)). The group C viruses (e.g., serotypes 2 and 5, or Ad2 and Ad5) are well characterized, and currently are employed for gene transfer studies, including human gene therapy trials (see, e.g., Rosenfeld et al., *Science,* 252: 431-434 (1991); Rosenfeld et al., *Cell,* 68: 143-155 (1992); Zabner, *Cell,* 75: 207-216 (1993); Crystal et al., *Nat. Gen.,* 8: 42-51 (1994); Yei et al., *Gene Therapy,* 1: 192-200 (1994); Chen et al., *Proc. Natl. Acad. Sci.,* 91: 3054-3057 (1994); Yang et al., *Nat. Gen.,* 7: 362-369 (1994); Zabner et al., *Nat. Gen.,* 6: 75-83 (1994)). Typically, an adenoviral vector is generated by introducing one or more mutations (e.g., deletion, insertion, or substitution) into the adenoviral genome of the adenovirus so as to accommodate the insertion of a non-native nucleic acid sequence, for example, for gene transfer, into the adenovirus.

The adenovirus capsid mediates the key interactions of the early stages of the infection of a cell by the virus, and is required for packaging adenovirus genomes at the end of the adenovirus life cycle. The capsid comprises 252 capsomeres, which includes 240 hexons, 12 penton base proteins, and 12 fibers (Ginsberg et al., *Virology,* 28: 782-83 (1966)). In one embodiment of the invention, one or more capsid proteins (also referred to herein as "coat" proteins) of the adenoviral vector can be manipulated to alter the binding specificity or recognition of the vector for a viral receptor on a potential host cell. Such manipulations can include deletion of regions of the fiber or penton, insertions of various native or non-native ligands into portions of the capsid proteins, and the like. Manipulation of capsid proteins can broaden the range of cells infected by the adenoviral vector or enable targeting of the adenoviral vector to a specific cell type.

The adenoviral vector of the invention can comprise a modified hexon protein. The adenovirus hexon protein is the largest and most abundant protein in the adenovirus capsid. The hexon protein is essential for virus capsid assembly, determination of the icosahedral symmetry of the capsid (which in turn defines the limits on capsid volume and DNA packaging size), and integrity of the capsid. In addition, the hexon protein is a primary target for modification in order to reduce neutralization of adenoviral vectors (see, e.g., Gall et al., *J. Virol.,* 72: 10260-264 (1998), and Rux et al., *J. Virol.,* 77(17): 9553-9566 (2003)). The major structural features of the hexon protein are shared by adenoviruses across serotypes, but the hexon protein differs in size and immunological properties between serotypes (Jornvall et al., *J. Biol. Chem.,* 256(12): 6181-6186 (1981)). A comparison of 15 adenovirus hexon proteins reveals that the predominant antigenic and serotype-specific regions of the hexon protein appear to be in loops 1 and 2 (i.e., LI or l1, and LII or l2, respectively), within which are seven to nine discrete hypervariable regions (HVR1 to HVR 7 or HVR9) varying in length and sequence between adenoviral serotypes (Crawford-Miksza et al., *J. Virol.*, 70(3): 1836-1844 (1996), and Bruder et al., *PLoS ONE*, 7(4): e33920 (2012)).

The hexon protein of the adenoviral vector can be "modified" in that it comprises a non-native amino acid sequence in addition to or in place of a wild-type hexon amino acid sequence of the adenoviral vector. In this respect, at least a portion of the wild-type hexon protein (e.g., the entire hexon protein) of the adenoviral vector desirably is removed and replaced with a corresponding portion of a hexon protein from another adenovirus.

For example, a portion of the wild-type hexon protein of a serotype 28 adenoviral vector can be removed and replaced with a corresponding portion of a hexon protein from any group D adenovirus (such as those described herein). In particular, a portion of the wild-type hexon protein of a serotype 28 adenoviral vector can be removed and replaced with a corresponding portion of a hexon protein from serotype 45 adenovirus (i.e., a serotype 28 adenoviral vector comprises at least a portion of an adenovirus serotype 45 hexon protein in place of at least a portion of the endogenous serotype 28 hexon protein). Any suitable amino acid residue(s) of a wild-type hexon protein of the serotype 28 adenoviral vector can be modified or removed, so long as viral capsid assembly is not impeded. Similarly, amino acids can be added to the hexon protein as long as the structural integrity of the capsid is maintained. In a preferred embodiment, at least 50% (e.g., at least 55%, at least 60%, at least 65%, at least 70%, at least 75%, at least 80%, at least 85%, at least 90%, at least 95%, or 100%) of the endogenous Ad28 hexon protein is modified or removed.

A "portion" of an amino acid sequence comprises at least three amino acids (e.g., about 3 to about 800 amino acids). Preferably, a "portion" comprises 10 or more (e.g., 10 or more, 15 or more, 20 or more, 25 or more, 30 or more, 40 or more, 50 or more, or 100 or more) amino acid residues, but less than the entire wild-type hexon protein (e.g., 900 or less, 800 or less, 700 or less, 600 or less, 500 or less, 400 or less, 300 or less, 200 or less, or 100 or less amino acid residues). For example, a portion can be about 10 to about 700 amino acids (e.g., about 10, 100, 300, 500, or 600 amino acids), about 10 to about 500 amino acids (e.g., about 20, 50, 200, or 400 amino acids), or about 10 to about 300 amino acids (e.g., about 15, 40, 60, 70, 90, 150, 250, or 290 amino acids), or a range defined by any two of the foregoing values. More preferably, a "portion" comprises no more than about 600 amino acids (e.g., about 10 to about 550 amino acids, about 10 to about 500 amino acids, or about 50 to about 300 amino acids, or a range defined by any two of the foregoing values).

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. Preferably, a portion of a nucleic acid sequence is about 10 to about 3500 nucleotides (e.g., about 10, 20, 30, 50, 100, 300, 500, 700, 1000, 1500, 2000, 2500, or 3000 nucleotides), about 10 to about 1000 nucleotides (e.g., about 25, 55, 125, 325, 525, 725, or 925 nucleotides), or about 10 to about 500 nucleotides (e.g., about 15, 30, 40, 50, 60, 70, 80, 90, 150, 175, 250, 275, 350, 375, 450, 475, 480, 490, 495, or 499 nucleotides), or a range defined by any two of the foregoing values. More preferably, a "portion" of a nucleic acid sequence comprises no more than about 3200 nucleotides (e.g., about 10 to about 3200 nucleotides, about 10 to about 3000 nucleotides, or about 30 to about 500 nucleotides, or a range defined by any two of the foregoing values).

Desirably, the portion of an adenovirus serotype 45 hexon protein comprises at least one hypervariable region (HVR) in place of an endogenous Ad28 HVR. Thus, at least one HVR of the hexon protein of the serotype 28 adenoviral vector is removed and replaced with at least one HVR from a wild-type serotype 45 adenovirus. In one embodiment, the serotype 28 adenoviral vector can comprise one or more of HVR1, HVR2, HVR3, HVR4, HVR5, HVR6, HVR7, HVR8, or HVR9 of a wild-type serotype 45 adenovirus hexon protein in place of the corresponding endogenous Ad28 HVR. Preferably, two or more (e.g., 2, 3, 4, 5, 6, 7, 8, or 9) HVRs of the hexon protein of the serotype 28 adenoviral vector are removed and replaced with corresponding HVRs from a serotype 45 adenovirus. More preferably, the inventive serotype 28 adenoviral vector comprises all nine HVRs of a serotype 45 hexon protein in place of the corresponding endogenous Ad28 HVRs. In one embodiment, the entire wild-type hexon protein of the serotype 28 adenoviral vector is replaced with the entire hexon protein of a serotype 45 adenovirus.

Nucleic acid sequences that encode all or a portion of a serotype 28 or 45 adenovirus hexon protein are publicly available (see, e.g., GenBank Accession Nos. DQ149626.1 or AB330126.1, or AB330107). Amino acid sequences that comprise a full-length serotype 28, 45, or 26 adenovirus hexon protein, or portions thereof, also are publicly available (see, e.g., GenBank Accession Nos. ABA00010.1 or BAG48822). In one embodiment, the portion of an adenovirus serotype 45 hexon protein comprises, for example, the amino acid sequence of SEQ ID NO: 1, and a nucleic acid sequence that encodes a portion of a serotype 45 adenovirus hexon protein comprises, for example, SEQ ID NO: 2.

In another embodiment, the portion of an adenovirus serotype 45 hexon protein comprises an amino acid sequence that is at least 91.4% identical (e.g., at least 91.5% identical, at least 92% identical, at least 92.5% identical, at least 93% identical, at least 93.5% identical, at least 94% identical, at least 94.5% identical, at least 95% identical, at least 95.5% identical, at least 96% identical, at least 96.5% identical, at least 97% identical, at least 97.5% identical, at least 98% identical, at least 98.5% identical, at least 99% identical, or at least 99.5% identical) to SEQ ID NO: 1.

Nucleic acid or amino acid sequence "identity," as described herein, can be determined by comparing a nucleic acid or amino acid sequence of interest to a reference nucleic acid or amino acid sequence. The number of nucleotides or amino acid residues that have been changed and/or modified (such as, e.g., by point mutations, insertions, or deletions) in the reference sequence so as to result in the sequence of interest are counted. The total number of such changes is subtracted from the total length of the sequence of interest, and the difference is divided by the length of the sequence of interest and expressed as a percentage. A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 215(3): 403-410 (1990); Beigert et al., *Proc. Natl. Acad. Sci. USA*, 106(10): 3770-3775 (2009); Durbin et al., eds., *Biological Sequence Analysis: Probalistic Models of Proteins and Nucleic Acids*, Cambridge University Press, Cambridge, U.K. (2009), Soding, *Bioinformatics*, 21(7): 951-960 (2005); Altschul et al., *Nucleic Acids Res.*, 25(17): 3389-3402 (1997); and Gusfield, *Algorithms on Strings, Trees and Sequences*, Cambridge University Press, Cambridge, U.K. (1997)).

In a particular embodiment, the serotype 28 adenoviral vector comprises a nucleic acid sequence encoding a hexon protein that comprises a first portion of an Ad28 hexon protein, a second portion of an Ad45 hexon protein, and a third portion of an Ad28 hexon. The nucleic acid sequence encoding the hexon protein comprises the nucleic acid sequences of SEQ ID NOs: 12, 13, and 14, respectively. The nucleic acid sequence of the Ad28/Ad45 hexon protein can comprise the nucleic acid sequence of SEQ ID NO: 15, wherein SEQ ID NO: 15 contains SEQ ID NOs: 12, 13, and 14, and wherein the nucleic acid sequence of SEQ ID NO: 12 (Ad28 hexon) corresponds to residues 1-177 (encoding amino acids 1-59) of SEQ ID NO: 15; the nucleic acid sequence of SEQ ID NO: 13 (Ad45 hexon) corresponds to residues 178-1767 (encoding amino acids 60-589) of SEQ ID NO: 15; and the nucleic acid sequence of SEQ ID NO: 14 (Ad28 hexon) corresponds to residues 1768-2850 (encoding amino acids 590-950) of SEQ ID NO: 15, such that the nucleic acid sequence of SEQ ID NO: 15 contains 2850 nucleotides encoding 950 amino acids (including the stop codon).

The adenoviral vector of the invention also can comprise a modified fiber protein. The adenovirus fiber protein is a homotrimer of the adenoviral polypeptide IV that has three domains: the tail, shaft, and knob (Devaux et al., *J. Molec. Biol.*, 215: 567-88 (1990), and Yeh et al., *Virus Res.*, 33: 179-98 (1991)). The fiber protein mediates primary viral binding to receptors on the cell surface via the knob and the shaft domains (Henry et al., *J. Virol.*, 68(8): 5239-46 (1994)). The amino acid sequences for trimerization are located in the knob, which appears necessary for the amino terminus of the fiber (the tail) to properly associate with the penton base (Novelli et al., *Virology*, 185: 365-76 (1991)). In addition to recognizing cell receptors and binding the penton base, the fiber contributes to serotype identity. Fiber proteins from different adenoviral serotypes differ considerably (see, e.g., Green et al., *EMBO J.*, 2: 1357-65 (1983), Chroboczek et al., *Virology*, 186: 280-85 (1992), and Signas et al., *J. Virol.*, 53: 672-78 (1985)). Thus, the fiber protein has multiple functions that are key to the life cycle of adenovirus.

The fiber protein is "modified" in that it comprises a non-native amino acid sequence, in addition to or in place of a wild-type fiber amino acid sequence of the inventive serotype 28 adenoviral vector. In this respect, a portion of the wild-type fiber protein (e.g., the fiber tail, the fiber shaft, the fiber knob, or the entire fiber protein) of the inventive serotype 28 adenoviral vector can be removed and replaced with a corresponding portion of a fiber protein from another adenovirus.

For example, a portion of the wild-type fiber protein of the inventive serotype 28 adenoviral vector can be removed and replaced with a corresponding portion of a fiber protein from any group D adenovirus. In particular, a portion of the wild-type fiber protein of a serotype 28 adenoviral vector can be removed and replaced with a corresponding portion of a fiber protein from serotype 45 or serotype 26 adenovirus (i.e., a serotype 28 adenoviral vector comprises at least a portion of an adenovirus serotype 45 or serotype 26 fiber protein in place of at least a portion of the endogenous serotype 28 fiber protein). Any suitable amino acid residue (s) of a wild-type fiber protein of the serotype 28 adenoviral vector that mediates or assists in the interaction between the fiber knob and the native cellular receptor can be modified or removed, so long as the fiber protein is able to trimerize. Similarly, amino acids can be added to the fiber knob as long as the fiber protein retains the ability to trimerize. In a preferred embodiment, at least 75% (e.g., at least 80%, at least 85%, at least 90%, at least 95%, or 100%) of the endogenous Ad28 fiber protein is modified or removed.

Nucleic acid sequences that encode all or a portion of a serotype 28, 45, or 26 adenovirus fiber protein are publicly available (see, e.g., GenBank Accession Nos. AB361404.1, Y14242.1, FM210554.1, and AB361421.1 and residues 30962-32086 of GenBank Accession No. EF153474.1). Amino acid sequences that comprise a full-length serotype 28, 45, or 26 adenovirus fiber protein, or portions thereof, also are publicly available (see, e.g., GenBank Accession Nos. ACQ91171, CAR66130.1, BAG71098.1, CAH18767.1 and ABO61321.1). In one embodiment, the portion of an adenovirus serotype 45 fiber protein comprises the amino acid sequence of SEQ ID NO: 3, and a nucleic acid sequence that encodes a portion of a serotype 45 adenovirus fiber protein comprises, for example, SEQ ID NO: 4. In another embodiment, the portion of an adenovirus serotype 26 fiber protein comprises the amino acid sequence of SEQ ID NO: 11. In a further embodiment, the portion of an adenovirus serotype 45 or 26 fiber protein comprises an amino acid sequence that is at least 67% identical (e.g., at least 68% identical, at least 69% identical, at least 70% identical, at least 71% identical, at least 72% identical, at least 73% identical, at least 74% identical, at least 75% identical, at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, or at least 99% identical) to SEQ ID NO: 3 or SEQ ID NO: 11, respectively.

In a particular embodiment, the serotype 28 adenoviral vector comprises a nucleic acid sequence encoding a fiber protein that comprises a first portion of an Ad28 fiber (tail) protein, a second portion of an Ad45 fiber (shaft) protein, and a third portion of an Ad45 fiber (knob) protein. The nucleic acid sequence encoding the fiber protein comprises the nucleic acid sequences of SEQ ID NOs: 16, 17, and 18, respectively. The nucleic acid sequence of the Ad28/Ad45 fiber protein can comprise the nucleic acid sequence of SEQ ID NO: 19, wherein SEQ ID NO: 19 contains SEQ ID NOs: 16, 17, and 18, and wherein the nucleic acid sequence of SEQ ID NO: 16 (Ad28 fiber (tail)) corresponds to residues 1-135 (encoding amino acids 1-45) of SEQ ID NO: 19; the nucleic acid sequence of SEQ ID NO: 17 (Ad45 fiber (shaft)) corresponds to residues 136-564 (encoding amino acids 46-188) of SEQ ID NO: 19; and the nucleic acid sequence of SEQ ID NO: 18 (Ad45 fiber (knob)) corresponds to residues 565-1110 (encoding amino acids 189-370) of SEQ ID NO: 19, such that the nucleic acid sequence of SEQ ID NO: 19 contains 1110 nucleotides encoding 370 amino acids (including the stop codon).

Figure 8:
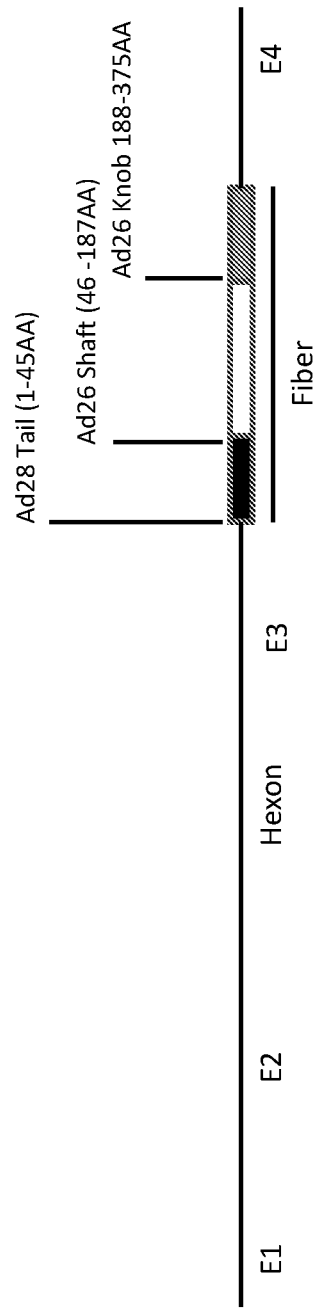
FIG. 8 is a schematic of an Ad28 vector comprising a portion of an Ad36 fiber protein in place of a portion of a corresponding endogenous serotype Ad28 fiber protein (Ad28F(26SK)). The Ad28/Ad26 fiber protein is encoded by the nucleic acid sequence of SEQ ID NO: 23.

In another particular embodiment, the serotype 28 adenoviral vector comprises a nucleic acid sequence encoding a fiber protein that comprises a first portion of an Ad28 fiber (tail) protein, a second portion of an Ad26 fiber (shaft) protein, and a third portion of an Ad26 fiber (knob) protein. The nucleic acid sequence encoding the fiber protein can comprise the nucleic acid sequences of SEQ ID NOs: 20, 21, and 22, respectively. The nucleic acid sequence of the Ad28/Ad26 fiber protein can comprise the nucleic acid sequence of SEQ ID NO: 23, wherein SEQ ID NO: 23 contains SEQ ID NOs: 20, 21, and 22, and wherein the nucleic acid sequence of SEQ ID NO: 20 (Ad28 fiber (tail)) corresponds to residues 1-135 (encoding amino acids 1-45) of SEQ ID NO: 23; the nucleic acid sequence of SEQ ID NO: 21 (Ad26 fiber (shaft) protein) corresponds to residues 136-561 (encoding amino acids 46-187) of SEQ ID NO: 23; and the nucleic acid sequence of SEQ ID NO: 22 (Ad26 fiber (knob)) corresponds to residues 562-1125 (encoding amino acids 188-375) of SEQ ID NO: 23, such that the nucleic acid sequence of SEQ ID NO: 23 contains 1125 nucleotides encoding 375 amino acids (including the stop codon). An exemplary schematic of an Ad28/Ad26 fiber protein is depicted in FIG. 8.

Figure 9:
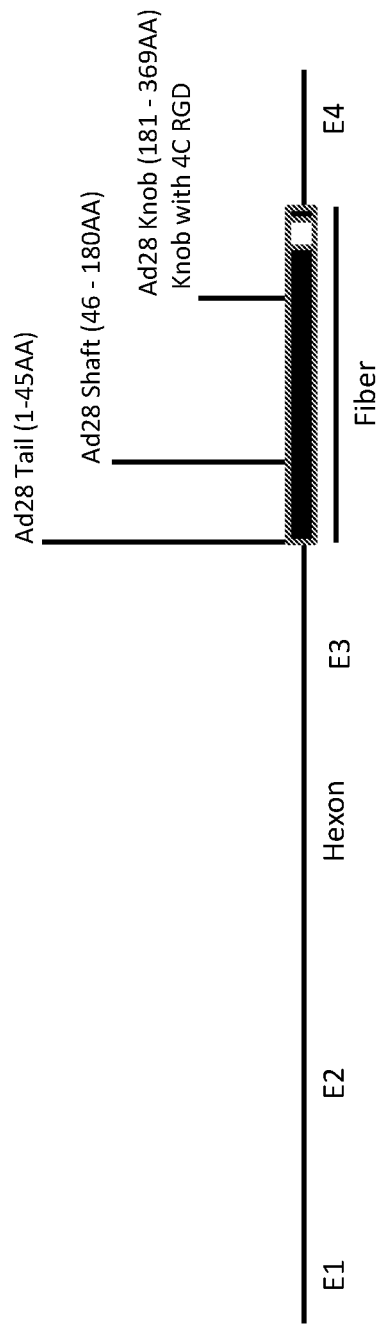
FIG. 9 is a schematic of an Ad28 vector comprising a fiber protein containing a high affinity RGD ligand (Ad28F (RGD)). The Ad28F(RGD) fiber protein is encoded by the nucleic acid sequence of SEQ ID NO: 26.

The adenoviral vector fiber also can be modified with RGD, pK7, or a related modification to increase tropism and delivery capability into dividing human T cells. Inclusion of the pK7 peptide (SEQ ID NO: 28) targets heparan sulfate-containing receptors. The RGD peptide (SEQ ID NO: 27) is the binding motif of fibronectin to cell adhesion molecules, and inclusion of the RGD peptide targets $\alpha_v$ integrins. When the adenoviral vector fiber is modified to include the RGD peptide, the RGD peptide can be in any suitable portion of the fiber protein, such as the HI loop of fiber. In a particular embodiment, the serotype 28 adenoviral vector can comprise a first portion of an Ad28 fiber (tail) protein, a second portion of an Ad28 fiber (shaft) protein, and a third portion of a modified Ad28 fiber (knob) protein comprising RGD. The nucleic acid sequence encoding the fiber protein can comprise the nucleic acid sequences of SEQ ID NOs: 20, 24, and 25, respectively. The nucleic acid sequence of the Ad28 fiber with RGD-modified knob can comprise the nucleic acid sequence of SEQ ID NO: 26, wherein SEQ ID NO: 26 contains SEQ ID NOs: 20, 24, and 25, and wherein the nucleic acid sequence of SEQ ID NO: 20 (Ad28 fiber (tail)) corresponds to residues 1-135 (encoding amino acids 1-45) of SEQ ID NO: 26, the nucleic acid sequence of SEQ ID NO: 24 (Ad28 fiber (shaft) protein) corresponds to residues 136-540 (encoding amino acids 46-180) of SEQ ID NO: 26, and the nucleic acid sequence of SEQ ID NO: 25 (Ad28 fiber (knob) containing 4C RGD) corresponds to residues 541-1107 (encoding amino acids 181-369) of SEQ ID NO: 26, such that the nucleic acid sequence of SEQ ID NO: 26 contains 1107 nucleotides encoding 369 amino acids (including the stop codon). An exemplary schematic of an Ad28 fiber with an RGD modification is depicted in FIG. 9.

The serotype 28 adenoviral vector can comprise the aforementioned modified hexon protein, the aforementioned modified fiber protein, or the modified hexon protein and the modified fiber protein. For example, the serotype 28 adenoviral vector can comprise at least a portion of an adenovirus serotype 45 hexon protein in place of at least a portion of the endogenous serotype 28 hexon protein, or at least a portion of an adenovirus serotype 45 or serotype 26 fiber protein in place of at least a portion of the endogenous serotype 28 fiber protein. Alternatively, the serotype 28 adenoviral vector can comprise at least a portion of an adenovirus serotype 45 hexon protein in place of at least a portion of the endogenous serotype 28 hexon protein, and at least a portion of an adenovirus serotype 45 fiber protein in place of at least a portion of the endogenous serotype 28 fiber protein. An exemplary schematic of an Ad28 vector containing portions of Ad45 hexon and Ad45 fiber is depicted in FIG. 7. Such an adenoviral vector is described in U.S. Patent Application Publication 2015/0167018.

Modifications to adenovirus coat proteins, including methods for generating chimeric hexon and fiber proteins, are described in, for example, e.g., U.S. Pat. Nos. 5,543,328; 5,559,099; 5,712,136; 5,731,190; 5,756,086; 5,770,442; 5,846,782; 5,871,727; 5,885,808; 5,922,315; 5,962,311; 5,965,541; 6,057,155; 6,127,525; 6,153,435; 6,329,190; 6,455,314; 6,465,253; 6,576,456; 6,649,407; and 6,740,525; U.S. Patent Application Publications 2001/0047081 A1, 2002/0099024 A1, 2002/0151027 A1, 2003/0022355 A1, and 2003/0099619 A1, and International Patent Application Publications WO 1996/007734, WO 1996/026281, WO 1997/020051, WO 1998/007865, WO 1998/007877, WO 1998/040509, WO 1998/054346, WO 2000/015823, WO 2001/058940, and WO 2001/092549.

The adenoviral vector can be replication-competent, conditionally replication-competent, or replication-deficient.

A replication-competent adenoviral vector can replicate in typical host cells, i.e., cells typically capable of being infected by an adenovirus. A replication-competent adenoviral vector can have one or more mutations as compared to the wild-type adenovirus (e.g., one or more deletions, insertions, and/or substitutions) in the adenoviral genome that do not inhibit viral replication in host cells. For example, the adenoviral vector can have a partial or entire deletion of the adenoviral early region known as the E3 region, which is not essential for propagation of the adenoviral genome.

A conditionally-replicating adenoviral vector is an adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. In such an embodiment, replication requires the presence or absence of specific factors that interact with the transcription control sequence. Conditionally-replicating adenoviral vectors are further described in U.S. Pat. No. 5,998,205.

A replication-deficient adenoviral vector is an adenoviral vector that requires complementation of one or more gene functions or regions of the adenoviral genome that are required for replication, as a result of, for example, a deficiency in the one or more replication-essential gene function or regions, such that the adenoviral vector does not replicate in typical host cells, especially those in a human to be infected by the adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions may be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

Whether the adenoviral vector is replication-competent or replication-deficient, the adenoviral vector retains at least a portion of the adenoviral (e.g., Ad28 or Ad35) genome. The adenoviral vector can comprise any portion of the adenoviral (e.g., Ad28 or Ad35) genome, including protein coding and non-protein coding regions. Desirably, the adenoviral vector comprises at least one nucleic acid sequence that encodes an adenoviral (e.g., Ad28 or Ad35) protein. The adenoviral vector can comprise any suitable adenovirus protein, or a nucleic acid sequence that encodes any suitable adenovirus protein, such as, for example, a protein of any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions).

The adenoviral vector desirably comprises one or more amino acid sequences of the pIX protein, the penton protein, the p100 protein, the L1 52/55K protein of an adenovirus (e.g., Ad28 or Ad35), or any combination of the foregoing. The adenoviral vector can comprise a full-length amino acid sequence of the adenovirus (e.g., Ad28 or Ad35) protein. Alternatively, the adenoviral vector can comprise a portion of a full-length amino acid sequence of an adenovirus (e.g., Ad28 or Ad35) protein. An amino acid sequence of a serotype 28 adenovirus pIX protein comprises, for example, SEQ ID NO: 5. An amino acid sequence of a serotype 28 adenovirus penton protein comprises, for example, SEQ ID NO: 6. An amino acid sequence of a serotype 28 adenovirus p100 protein comprises, for example, SEQ ID NO: 7. An amino acid sequence of a serotype 28 adenovirus L1 52/55K protein comprises, for example, SEQ ID NO: 8. The adenoviral vector also desirably comprises a nucleic acid sequence encoding a DNA polymerase protein of a serotype 28 adenovirus or a portion thereof. A nucleic acid sequence encoding a DNA polymerase of a serotype 28 adenovirus comprises, for example, SEQ ID NO: 9. The adenoviral vector desirably comprises/encodes one or more of SEQ ID NOs: 5-9.

In another embodiment, the invention provides a virus-like particle comprising one or more amino acid sequences of the pIX protein, the penton protein, the p100 protein, the L1 52/55K protein of an adenovirus (e.g., Ad28), or any combination of the foregoing, as well as the serotype 45 hexon protein and/or the serotype 45 fiber protein described herein. A "virus-like particle" consists of one or more viral coat proteins that assemble into viral particles, but lacks any viral genetic material (see, e.g., Miyanohara et al., *J. Virol.*, 59: 176-180 (1986), Gheysen et al., *Cell*, 59: 103-112 (1989), and Buonaguro et al., *ASHI Quarterly*, 29: 78-80 (2005)).

Preferably, the adenoviral vector is replication-deficient, such that the replication-deficient adenoviral vector requires complementation of at least one replication-essential gene function of one or more regions of the adenoviral genome for propagation (e.g., to form adenoviral vector particles).

The replication-deficient adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad)). See Morsy et al., *Proc. Natl. Acad. Sci. USA*, 95: 965-976 (1998); Chen et al., *Proc. Natl. Acad. Sci. USA*, 94: 1645-1650 (1997); and Kochanek et al., *Hum. Gene Ther.*, 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The late regions of the adenoviral genome include the L1, L2, L3, L4, and L5 regions. The adenoviral vector also can have a mutation in the major late promoter (MLP), as discussed in International Patent Application Publication WO 2000/000628, which can render the adenoviral vector replication-deficient if desired.

The E1 region comprises the E A and E1B subregions, and one or more deficiencies in replication-essential gene functions in the E1 region can include one or more deficiencies in replication-essential gene functions in either or both of the E1A and E1B subregions, thereby requiring complementation of the deficiency in the E1A subregion and/or the E1B subregion of the adenoviral genome for the adenoviral vector to propagate (e.g., to form adenoviral vector particles).

The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the deficiency in the E2A subregion and/or the E2B subregion of the adenoviral genome for the adenoviral vector to propagate (e.g., to form adenoviral vector particles).

The E3 region does not include any replication-essential gene functions, such that a deletion of the E3 region in part or in whole does not require complementation of any gene functions in the E3 region for the adenoviral vector to propagate (e.g., to form adenoviral vector particles). In the context of the invention, the E3 region is defined as the region that initiates with the open reading frame that encodes a protein with high homology to the 12.5K protein from the E3 region of human adenovirus 28 (NCBI reference sequence FJ824826) and ends with the open reading frame that encodes a protein with high homology to the 14.7K protein from the E3 region of human adenovirus 28 (NCBI reference sequence FJ824826). The E3 region may be deleted in whole or in part, or retained in whole or in part. The size of the deletion may be tailored so as to retain an adenoviral vector whose genome closely matches the optimum genome packaging size. A larger deletion will accommodate the insertion of larger heterologous nucleic acid sequences in the adenoviral genome. In one embodiment of the invention, the L4 polyadenylation signal sequences, which reside in the E3 region, are retained.

The E4 region comprises multiple open reading frames (ORFs). An adenoviral vector with a deletion of all of the open reading frames of the E4 region except ORF6, and in some cases ORF3, does not require complementation of any gene functions in the E4 region for the adenoviral vector to propagate (e.g., to form adenoviral vector particles). Conversely, an adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the deficiency in the E4 region (specifically, of ORF6 and/or ORF3 of the E4 region) for the adenoviral vector to propagate (e.g., to form adenoviral vector particles).

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region. In other words, the adenoviral vector requires, at most, complementation of a deficiency in one or more early regions of the adenoviral genome for propagation.

The replication-deficient adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenoviral vector can be deficient in other respects that are not replication-essential. For example, the adenoviral vector can have a partial or entire deletion of the adenoviral early region known as the E3 region, which is not essential for propagation of the adenoviral genome.

In one embodiment, the adenoviral vector is replication-deficient and requires, at most, complementation of the E1 region of the adenoviral genome, for propagation (e.g., to form adenoviral vector particles). Thus, the replication-deficient adenoviral vector requires complementation of at least one replication-essential gene function of the E1A subregion and/or the E1B subregion of the adenoviral genome (denoted an E1-deficient adenoviral vector) for propagation (e.g., to form adenoviral vector particles). The adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). Such an adenoviral vector requires, at most, complementation of a deficiency in the E1 region of the adenoviral genome for propagation.

In one embodiment, the adenoviral vector is replication-deficient and requires, at most, complementation of the E2 region, preferably the E2A subregion, of the adenoviral genome, for propagation (e.g., to form adenoviral vector particles). Thus, the replication-deficient adenoviral vector requires complementation of at least one replication-essential gene function of the E2A subregion of the adenoviral genome (denoted an E2A-deficient adenoviral vector) for propagation (e.g., to form adenoviral vector particles). The adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector). Such an adenoviral vector requires, at most, complementation of a deficiency in the E2 region of the adenoviral genome for propagation.

In one embodiment, the adenoviral vector is replication-deficient and requires, at most, complementation of the E4 region of the adenoviral genome, for propagation (e.g., to form adenoviral vector particles). Thus, the replication-deficient adenoviral vector requires complementation of at least one replication-essential gene function of the E4 region of the adenoviral genome (denoted an E4-deficient adenoviral vector) for propagation (e.g., to form adenoviral vector particles). The adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector). Such an adenoviral vector requires, at most, complementation of a deficiency in the E4 region of the adenoviral genome for propagation.

In one embodiment, the adenoviral vector requires complementation of the E1 and E2 (e.g., E2A) regions of the adenoviral genome for propagation (denoted an E1/E2-deficient adenoviral vector), wherein the adenoviral vector also can be deficient in at least one gene function of the E3 region (denoted an E1/E2/E3-deficient adenoviral vector). Such an adenoviral vector requires, at most, complementation of a deficiency in the E1 region and a deficiency in the E2 region of the adenoviral genome for propagation.

In one embodiment, the adenoviral vector is replication-deficient and requires, at most, complementation of the E1 and E4 regions of the adenoviral genome for propagation (e.g., to form adenoviral vector particles). Thus, the replication-deficient adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). Such an adenoviral vector requires, at most, complementation of a deficiency in the E1 region and a deficiency in the E4 region of the adenoviral genome for propagation.

In a preferred embodiment, the adenoviral vector requires, at most, complementation of a deficiency in the E1 region of the adenoviral genome for propagation, and does not require complementation of any other deficiency of the adenoviral genome for propagation. In another preferred embodiment, the adenoviral vector requires, at most, complementation of a deficiency in both the E1 and E4 regions of the adenoviral genome for propagation, and does not require complementation of any other deficiency of the adenoviral genome for propagation.

The adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviruses or adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome, but does not restore the replication-essential function to the deficient region. The spacer also can contain an expression cassette. More preferably, the spacer comprises a polyadenylation sequence and/or a gene that is non-native with respect to the adenovirus or adenoviral vector. The use of a spacer in an adenoviral vector is further described in, for example, U.S. Pat. No. 5,851,806 and International Patent Application Publication WO 1997/021826.

The replication-deficient adenoviral vector of the invention can be produced in complementing cell lines that provide gene functions not present in the replication-deficient adenovirus or adenoviral vector, but required for viral propagation, at appropriate levels in order to generate high titers of viral vector stock. Such complementing cell lines are known and include, but are not limited to, 293 cells (described in, e.g., Graham et al., *J. Gen. Virol.*, 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 1995/34671 and Brough et al., *J. Virol.*, 71: 9206-9213 (1997)). Other suitable complementing cell lines to produce the replication-deficient adenoviral vector of the invention include complementing cells that have been generated to propagate adenoviral vectors encoding transgenes whose expression inhibits viral growth in host cells (see, e.g., U.S. Patent Application Publication 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenoviral vector. Alternatively, the inventive adenoviral vector can comprise a non-native replication-essential gene that complements for the one or more replication-essential gene functions lacking in the inventive replication-deficient adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenoviral vector, or an adenovirus of a different species than the inventive adenoviral vector).

An example of an E1/E3-deficient serotype 28 adenoviral vector comprising a serotype 45 hexon protein and a serotype 45 fiber protein as described herein comprises the nucleic acid sequence of SEQ ID NO: 10. Using the publicly available genome information for Ad28, however, one of ordinary skill in the art would be able generate other Ad28 vectors with similar deficiencies and/or modifications using routine methods known in the art and/or described herein.

The adenoviral vector can further comprise one or more exogenous or non-native nucleic acids, which can be positioned at any suitable place in the adenoviral vector. By removing all or part of the adenoviral genome, for example, the E1, E3, and E4 regions of the adenoviral genome, the resulting adenoviral vector is able to accept inserts of exogenous nucleic acid sequences while retaining the ability to be packaged into adenoviral capsids. An exogenous nucleic acid sequence can be inserted at any position in the adenoviral genome so long as insertion in the position allows for the formation of adenovirus or the adenoviral vector particle. The exogenous nucleic acid sequence preferably is positioned in the E1 region, the E3 region, or the E4 region of the adenoviral genome. In embodiments where the adenoviral vector comprises multiple exogenous nucleic acid sequences (e.g., 2, 3, 4 or more exogenous nucleic acid sequences), at least one exogenous nucleic acid sequence is positioned in the E1 region, and at least one exogenous nucleic acid sequence is positioned in the E4 region. For example, when the adenoviral vector comprises three exogenous nucleic acid sequences, two exogenous nucleic acid sequences can be positioned in the E1 region, and one exogenous nucleic acid sequence can be positioned in the E4 region.

An "exogenous" or "non-native" nucleic acid sequence is any nucleic acid sequence (e.g., DNA, RNA, or cDNA sequence) that is not a naturally occurring nucleic acid sequence of an adenovirus in a naturally occurring position. Thus, the non-native nucleic acid sequence can be naturally found in an adenovirus, but located at a non-native position within the adenoviral genome and/or operably linked to a non-native promoter. The terms "non-native nucleic acid sequence," "heterologous nucleic acid sequence," and "exogenous nucleic acid sequence" are synonymous and can be used interchangeably in the context of the invention. The non-native nucleic acid sequence preferably is DNA and preferably encodes a protein (i.e., one or more nucleic acid sequences encoding one or more proteins). The adenoviral vector can contain more than one (e.g., two, three, four, five, or more) non-native nucleic acid sequences.

The non-native nucleic acid sequence can encode a therapeutic protein that can be used to prophylactically or therapeutically treat a mammal for a disease or disorder. Examples of suitable therapeutic proteins include cytokines, toxins, tumor suppressor proteins, growth factors, hormones, receptors, mitogens, immunoglobulins, neuropeptides, neurotransmitters, and enzymes. Alternatively, the non-native nucleic acid sequence can encode an antigen of a pathogen (e.g., a bacterium or a virus), and the adenoviral vector can be used as a vaccine.

In a first embodiment, the non-native nucleic acid sequence corresponds to a nucleic acid sequence encoding a single chain variable anti-PSMA, anti-PSCA, anti-MUC1, anti-CD19, anti-ROR1, anti-mesothelin, anti-CD2, anti-CD123, anti-MUC16, anti-Her2/Neu, anti-L1 CAM, or anti-BCMA. The administration of an adenoviral vector comprising one or more of these particular non-native nucleic acid sequences to a T cell results in a chimeric antigen receptor (CAR), wherein the specificity of the antibody associated with activating signaling mediated through intracytoplasmic sequence from CD28, CD3zeta, and/or 4-1BB (CD137) is grafted onto the T cell.

In a second embodiment, the non-native nucleic acid sequence corresponds to a nucleic acid sequence encoding $\alpha\beta$ or $\gamma\delta$ T cell receptor (TCR), such as a TCR specific for a cancer or infectious disease epitope. In particular, the TCR can be specific for a cancer or infection disease epitope restricted to an MHC-1 allele or MHC-like structure.

In a third embodiment, the non-native nucleic acid sequence corresponds to a wild-type human nucleic acid sequence, such as a wild-type human gene to treat human genetic disorder leading to T cell immunodeficiency (e.g., severe combined immunodeficiency (SCID)).

In a fourth embodiment, the non-native nucleic acid sequence can be used for gene editing technology. For example, the non-native nucleic acid sequence can encode a programmable DNA endonuclease or a donor DNA sequence, or be transcribed to produce a guide RNA sequence. The donor DNA sequence can be a therapeutic gene corresponding to a CAR, TCR, or wild-type human gene sequence.

The invention encompasses the use of any suitable programmable DNA endonuclease including, but not limited to CRISPR/Cas9, meganuclease (e.g., MegaTAL or ARCUS™ meganuclease), TALENS, zinc finger nuclease (ZFN), and Cpf1.

The targeted T cells can have one or more genes inactivated or knocked out through the non-homologous end joining (NHEJ) DNA repair mechanism occurring after a DNA cut mediated by the programmable DNA endonuclease. The programmable DNA endonucleases can cut DNA at a specific location, activating DNA repair mechanisms. During NHEJ repair, there can be a random insertion of a few nucleic acids, leading to inactivation of the targeted gene.

For instance, α and/or β chains of the TCR can be targeted by programmable gene editing technologies for T cells (e.g., CAR T cells) to no longer express their endogenous TCR. These TCR-deficient T cells allow administration of the T cells to any patients since these T cells cannot induce graft versus host disease, which is mediated by T cell TCR cross-reactivity with allogeneic HLA alleles from the recipient.

Other T cell genes that can be targeted with gene editing include immune check point pathways, such as PD-1, CTLA-4, BTLA, KIR, LAG3, Tim3 and/or Adenosine 2a receptor (A2aR). Many of these pathways are on their own therapeutic targets since they have been shown to be engaged by tumor microenvironment (TME) to decrease the killing activity of tumor-specific T cells. Engineered CAR T cells also are subject to the TME mediated immune exhaustion, such that the inactivation of the immune check points gene in CAR T cell therapeutics likely will reduce their susceptibility to TME mediated immunosuppression and sustain their anti-tumor efficacy in vivo. With the same idea to sustain CAR T cell function in patient, the T cells can be inactivated for MHC-I and II genes to limit host versus graft allogenic responses leading to the premature elimination of CAR T cells. Furthermore, some enzymes targeted by chemotherapeutic agents, like deoxycytidine kinase (dCK) can be knocked out for CAR T cells to resist to purine nucleotide analogues treatment (PNA). Such editing allows CAR T cell to be combined with standard of care chemotherapeutics like PNA. Additionally, since some tumor associated antigens (TAA), like CD52, can be found at the surface of healthy T cells, CAR T cells can be genetically edited to no longer express the targeted TAA so that CAR T cells do not target and kill each other during the ex vivo production process.

In a fifth embodiment, the non-native nucleic acid sequence can be transcribed to produce a siRNA sequence. T cells (e.g., CAR T cells) can be generated using siRNA to prevent the expression of one or more specific proteins (e.g., such as those described herein) in the T cell to increase functionality. Multiple gene specific siRNA could be introduced in T cells (e.g., CAR T cells) via a T cell transducing vector. In contrast to gene editing, the inactivation will be at the mRNA level and, thus, a transient approach.

In a sixth embodiment, the non-native nucleic acid sequence can be a suicide gene, such as a suicide gene encoding CD20, rimiducid inducible caspase-9, or herpes simplex virus-thymidine kinase. As noted above, the adenoviral vector can contain more than one non-native nucleic acid sequence, wherein one of the non-native nucleic acid sequences encodes therapeutic material (e.g., for the production of TCR or CAR engineered T cells) and another non-native nucleic acid sequence is a suicide gene. The inclusion of the suicide gene could be used to inactivate the CAR T cells (in the event that a complication called cytokine release syndrome caused by large production of cytokines like IL-6, IL-10, and IFNγ due to the massive destruction of tumor cells by the CAR T cells is triggered). The suicide gene also could be used in the event that CAR T cells begin targeting healthy tissues, such that the CAR T cells need to be inactivated to prevent damage to healthy tissue.

The non-native nucleic acid sequence can be in the form of a transgene. The term "transgene" is defined herein as a non-native nucleic acid sequence that is operably linked to appropriate regulatory elements (e.g., a promoter), such that the non-native nucleic acid sequence can be expressed to produce a protein (e.g., peptide or polypeptide). The regulatory elements (e.g., promoter) can be native or non-native to the adenovirus or adenoviral vector.

The type of promoter will depend on the particular non-native nucleic acid sequence. For example, CAR engineered T cells have to be present for an extended length of time (e.g., about a month) to significantly reduce tumor size and/or change the course of the disease or infection (e.g., towards cure or remission). Thus, promoters that provide a strong expression of the CAR gene for an extended period of time are preferred. However, for a gene editing approach, nuclease, guide RNA, or donor DNA do not have to be present in the T cell nucleus for the same length of time to achieve the desired targeted somatic genetic modification. Thus, promoters that provide moderate and short term expression of the gene editing technology are preferred. Examples of suitable promoters include, but are not limited to, the CD3, CD4, CD8, EF-1, PGK, RSV, Beta-Actin, CMV, MCK, UB, and HIV-LTR promoters.

The invention also provides a cell comprising the adenoviral vector. The cell can be any suitable cell (e.g., a mammalian cell, such as a human cell) including a T cell (e.g., an activated T cell).

The invention provides a composition comprising the adenoviral vector or cell described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenoviral vector or cell. Any suitable carrier can be used within the context of the invention, and such carriers are well known in the art. The choice of carrier will be determined, in part, by the particular use of the composition (e.g., administration to a mammal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenovirus or adenoviral vector is part of a composition formulated to protect the adenovirus or adenoviral vector from damage prior to administration. For example, the composition can be formulated to reduce loss of the adenovirus or adenoviral vector on devices used to prepare, store, or administer the adenovirus or adenoviral vector, such as glassware, syringes, or needles. The composition can be formulated to decrease the light sensitivity and/or temperature sensitivity of the adenovirus or adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector, and facilitate its administration. Formulations for adenovirus or adenoviral vector-containing compositions are further described in, for example, U.S. Pat. Nos. 6,225,289, 6,514,943, and International Patent Application Publication WO 2000/034444.

The composition also can be formulated to enhance transduction efficiency. In addition, one of ordinary skill in the art will appreciate that the adenoviral vector can be present in a composition with other therapeutic or biologically-active agents. For example, factors that control inflammation, such as ibuprofen or steroids, can be part of the composition to reduce swelling and inflammation associated with in vivo administration of the adenoviral vector. If the adenoviral vector is used to deliver an antigen-encoding nucleic acid sequence to a host, immune system stimulators or adjuvants, e.g., interleukins, lipopolysaccharide, double-stranded RNA, and/or TNFSF14/LIGHT (see, e.g., Zhang et al., *J. Virol. Methods*, 153(2): 142-148 (2008)) can be administered to enhance or modify any immune response to the antigen. Antibiotics, i.e., microbicides and fungicides, can be utilized to treat existing infection and/or reduce the risk of future infection, such as infection associated with gene transfer procedures.

The invention further provides a method of transducing T cells, which method comprises contacting the T cells with an adenoviral vector described herein, thereby transducing the T cells with the vector. The adenoviral vector can be contacted with the T cells in vitro, ex vivo, or in vivo. In one embodiment, the T cells are isolated from a patient (e.g., a healthy donor or a patient suffering from cancer and/or infection), contacted with the adenoviral vector, and (re) introduced into a patient.

The T cells can be activated prior to contacting the T cells with the vector. Activation of the T cells can occur by contacting the T cells with one or more (e.g., 1, 2, 3, 4, or 5) anti-CD3, anti-CD28, and/or anti-CD137 antibodies and/ or one or more (e.g., 1, 2, 3, 4, or 5) costimulatory molecules. Suitable costimulatory molecules include, but are not limited to, CD28, CD137/4-1BB, CD40, CD40L, ICOS, OX40, CD2, LFA1, galectin 9, GITR, and combinations thereof. The antibodies and/or costimulatory molecules can be in solution or coated onto a plate, dish, flask, or any type of plastic-ware used for stimulation, or on beads (e.g., Dynabeads® magnetic beads).

The T cells (e.g., activated T cells) can be cultured in a serum-free medium prior to contact with the adenoviral vector to expand the number of T cells. In one embodiment, the serum-free medium comprises a cytokine selected from the group consisting of IL-2, IL-7, IL-12, IL-15, IL-21, and combinations thereof. The expansion of the T cells can occur in any suitable container, such as plastic-ware or in a bag used for wave bio-reactors in the case of activating beads. The T cells can be contacted with the adenoviral vector 1-15 (e.g., 1, 2, 3, 4, 5, 6, 7, 8, 9, 10, 11, 12, 13, 14, 15, and ranges thereof) days after the T cells are activated.

The T cells can be isolated from a patient suffering from cancer or an infection. Non-limiting examples of specific types of cancers include cancer of the head and neck, eye, skin, mouth, throat, esophagus, chest, bone, lung, colon, sigmoid, rectum, stomach, prostate, breast, ovaries, kidney, liver, pancreas, brain, intestine, heart or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocyctic leukemia, acute undifferentiated leukemia, chronic myelocytic leukemia, chronic lymphocytic leukemia, hairy cell leukemia, or multiple myeloma. See, e.g., *Harrison's Principles of Internal Medicine*, Eugene Braunwald et al., eds., pp. 491 762 (15th ed. 2001). Non-limiting examples of an infection (e.g., a bacterial or viral infection) include HIV, HSV1, HSV2, EBV, CMV, HCV, HBV, tuberculosis, and parasitic infections.

The adenoviral vector can be administered in any suitable dosage. The adenoviral vector can be administered at a multiplicity of infection (MOI) of 100-100000 (e.g., 100, 200, 300, 400, 500, 600, 700, 800, 900, 1000, 2000, 3000, 4000, 5000, 6000, 7000, 8000, 9000, 10000, 15000, 20000, 25000, 30000, 40000, 45000, 50000, 55000, 60000, 65000, 70000, 75000, 80000, 85000, 90000, 95000, 100000 or ranges thereof) total particles (PU) per T cell, desirably about 4000-40000 PU per T cell, with a transduction efficiency of the T cells of about 40% to 100% (e.g., 40%, 42%, 45%, 47%, 50%, 52%, 55%, 57%, 60%, 62%, 65%, 67%, 70%, 72%, 75%, 77%, 80%, 82%, 85%, 87%, 90%, 92%, 95%, 97%, 100%, or ranges thereof).

After transduction of the adenoviral vector, the cells can be expanded for 1-10 (e.g., 1, 2, 3, 4, 5, 6, 7, 8, 9, 10, or ranges thereof) days and desirably 3-5 days prior to being formulated for therapeutic administration. For example, the T cells can be formulated in a pharmaceutical composition comprising the T cells and a pharmaceutically acceptable carrier as described herein. The T cells then can be administered to a patient (e.g., the patient from which the T cells were isolated) in any suitable manner. In one embodiment, the T cells are administered parenterally (e.g., subcutaneously, intravenously, intraarterially, intramuscularly, intradermally, interperitoneally, and intrathecally). In a particular embodiment, the T cells are administered intravenously in an autologous or allogeneic manner to patients. The patients can be any suitable mammal (e.g., mouse, rat, hamster, guinea pig, rabbit, cat, dog, pig, cow, horse, or primate, such as a human). Thus, the invention also provides a method of treating or inhibiting cancer or an infection by administering the transduced T cells to a patient.

The following examples further illustrate the invention but, of course, should not be construed as in any way limiting its scope.

Example 1

This example demonstrates the identification of adenoviral vectors with enhanced transduction of T cells.

T cells were thawed in a 37° C. water bath and immediately removed from the vial and added to a 50 mL conical tube. 15 mL media (RPMI+10% FBS+2 mM L-Glutamine) was added, dropwise, to the cells. The cell suspension was centrifuged at room temperature, 1600 rpm, for 10 minutes and the media was removed from the cell pellet, leaving approximately 1 mL remaining in the tube. Another 15 mL of media was added to resuspend the cell pellet. The cell suspension was centrifuged at room temperature, 1600 rpm, for 10 minutes. Media was removed and the cell pellet was resuspended in 5 mL fresh media. Cells were then counted and seeded into T25 flasks from 1e6 cells/mL to 2e6 cells/mL, total of 3-7 mL per flask. IL-2 was added to each flask at 100 U/mL (1.3E5 IU in one 10 μg vial after resuspending in 1 mL PBS).

The cells were then activated with Dynabeads® magnetic beads at a bead-to-cell ratio of 1:1 per Invitrogen Dynabeads® Human T-Activator Cd3/CD28 protocol (25 μl per 1e6 T cells). The magnetic beads were washed prior to use by adding 900 μl of the magnetic beads to a 15 mL conical tube followed by 2 mL of Dulbecco's PBS (DPBS). The tube was vortexed and then centrifuged at room temperature, 2500 rpm for 5 minutes. Following centrifugation, the DPBS was removed from the magnetic beads pellet and 900 μl of media was added to resuspend the magnetic beads pellet. The magnetic beads were then added to cells at 25 μl per 1e6 cells.

Initial screening was performed using donor T cells. GFP transgene-expressing vectors were chosen in order to evaluate the percentage of cell transduction for each vector construct. The amount of vector used for all evaluations was quantitated by the number of total particles (PU) per cell. In all studies, GFP expression is driven by an identical expression cassette driven by the hCMV promoter. The GFP-expressing vectors from both rare human and nonhuman origin were evaluated for transduction of T cells using UV microscope and flow cytometry. Initial screening was performed using a UV microscope for the GFP expression and a relative transduction score was given over the period of time of observation (observed for 19 days) (FIG. 1). A "++" relative score was given to the Ad5 sample at day 1 post transduction and all other observations were compared to this initial benchmark. An observation of GFP positive cells above the Ad5 percentage was given as "+++" or "++++" depending on GFP expression levels. An observation below the Ad5 transduction level was given a + or zero dependent on results observed.

From this initial observational screen, the vectors were categorized into three groups. Group 1 and Group 2 correspond to vectors with transduction efficiencies equal to or better than Ad5, respectively, as determined by GFP expression levels. Group 3 corresponds to vectors with lower transduction efficiency in comparison to the Ad5 vector benchmark.

Group 1: ++ Adef, Adf.F(F2KpK7); Adef.F(RGD); Ad28ef, Ad28ef.F(5S); GC44ef (see, e.g., U.S. Pat. No. 9,233,153); and GC45ef (see, e.g., U.S. Patent Application Publication 2014/0248308)

Group 2: +++ or ++++Ad28ef.F(26SK); Ad28ef.H(45)F (45SK); Ad28ef.F(H14CRGD); Ad35ef; and Ad14ef Group 3: +Ad35f.F(sK[C7]-HIRGD); Ad35f.F(s25k-RGD); Ad35f.F(s25k); SAV38ef; and Ad41ef The name of each adenoviral vector first identifies the serotype of the vector followed by ef, f, or L denoting GFP expression (ef and f) or luciferase expression (L), followed by the identification, in parenthesis, of any modifications (i.e., chimeric protein or addition of RGD or pK7) to the fiber protein F or hexon protein H of the adenoviral vector.

For example, Ad28ef.F(26SK) of Group 2 is a vector serotype 28 adenoviral vector comprising at least a portion of an adenovirus serotype 26 fiber protein in place of at least a portion of a corresponding endogenous serotype 28 fiber protein as described herein (e.g., an E1-deleted Ad28 vector with an Ad26 fiber shaft and fiber knob). Ad28ef.H(45)F (45SK) is a serotype 28 adenoviral vector comprising (i) at least a portion of an adenovirus serotype 45 hexon protein in place of at least a portion of a corresponding endogenous serotype 28 hexon protein and (ii) at least a portion of an adenovirus serotype 45 fiber protein in place of at least a portion of a corresponding endogenous serotype 28 fiber protein as described herein (e.g., an E1/E3-deleted Ad28/Ad45 hexon chimera and Ad28/Ad45 fiber chimera) (see, e.g., U.S. Patent Application Publication 2015/0167018). Ad28ef.F(HI4CRGD) is a serotype 28 adenoviral vector comprising a fiber protein containing a high affinity RGD ligand as described herein (e.g., an E1-deleted Ad28 with RGD in the fiber protein).

Secondary screening was performed using donor T cells. For the secondary screening, vectors from Group 1 and Group 2 were chosen to quantify the relative transduction efficiencies using flow cytometry. In the secondary screening, the T cells were transduced with 5000 PU per cell and harvested 48 hours post-transduction, and the samples were processed and analyzed by flow cytometry. GFP expression was measured with a BD FACS Canto II instrument and the data were analyzed using FlowJo software (FIG. 2). Four vectors were identified as high performing vectors for gene delivery to T cells. Four vectors from Group 1 (Adf.F (F2KpK7), Adef.F(RGD), Ad28ef, Ad28ef.F(5S)) were not included in the secondary screen due to nonavailability of the vector stocks even though those vectors transduction efficiencies were comparable to Ad5 based on the initial screen.

Results of these analyses demonstrated that adenoviral vectors are able to efficiently transduce T cells, and identified four vector designs with enhanced performance for gene delivery to T cells: Ad28ef.F(26SK); Ad28ef.H(45)F (45SK); Ad35ef; and Ad28ef.F(HI4CRGD).

Example 2

The example demonstrates the optimal multiplicity of infection (MOI) for adenoviral vector transduction of T cells.

T cells were thawed as described above. At 7 days post thaw, cells were reactivated with Dynabeads® magnetic beads. Eleven days post thaw the cells were infected. Cells were seeded at 1e6 cells/mL, 1 mL per well in a 12-well plate. All Luciferase and GFP vectors were infected, in duplicate, at MOI's of 4,000 PU/cell and 40,000 PU/cell. One lot of each type of vector was also infected, in duplicate, at 400,000 PU/cell. Cells were harvested 48 hours post infection, with cell counts performed on one replicate of each vector tested (FIG. 3). The luciferase vectors were analyzed for luciferase expression (FIG. 4), and the GFP vectors were subject to FACS analysis (FIG. 5).

Additionally, a second set of T cells were thawed as described above. Three days post thaw, cells were seeded at 1e6 cells/0.5 mL in 0.5 mL per well in a 12-well plate and infected in duplicate with GFP vectors at MOI's of 5,000 PU/cell, 10,000 PU/cell, 20,000 PU/cell and 40,000 PU/cell. Following infection, the plates were incubated at 37° C. for 90 minutes. After the incubation, 0.5 mL of media was added to each well. Cells were harvested 48 hours post infection, with cell counts performed on one replicate for each vector tested. Samples were subject to FACS analysis (FIG. 6).

These data show that MOI's of 40,000 and 20,000 particles per cell gave the highest transduction efficiency as measured by flow cytometry, with good cell viabilities (87.5%/87%, respectively).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A serotype 28 adenoviral vector comprising (i) at least a portion of an adenovirus serotype 26 fiber protein in place of at least a portion of a corresponding endogenous serotype 28 fiber protein and (ii) an exogenous nucleic acid sequence.

2. The vector of claim 1, which requires complementation of a deficiency in one or more early regions of the adenoviral genome for propagation and does not require complementation of any other deficiency of the adenoviral genome for propagation.

3. The vector of claim 1, wherein the vector comprises an RGD or pK7 modification to the knob.

4. The vector of claim 1, wherein the exogenous nucleic acid sequence encodes single chain variable anti-PSMA.

5. The vector of claim 1, wherein the exogenous nucleic acid sequence encodes an αβ T cell receptor (TCR).

6. The vector of claim 5, wherein the TCR is specific for a cancer or infectious disease epitope.

7. The vector of claim 1, wherein the exogenous nucleic acid sequence encodes CRISPR/Cas9, meganuclease, TALENS, zinc finger nuclease (ZFN), or Cpf1 DNA endonuclease.

8. The vector of claim 1, wherein the exogenous nucleic acid sequence is transcribed to produce a guide RNA sequence or siRNA sequence.

9. The vector of claim 1, wherein the exogenous nucleic acid sequence encodes rimiducid inducible caspase-9 or herpes simplex virus-thymidine kinase.

10. The vector of claim 1, wherein vector comprises a promoter operably linked to the exogenous nucleic acid sequence.

11. The vector of claim 10, wherein the promoter is the CD3, CD4, CD8, EF-1, PGK, RSV, Beta-Actin, CMV, MCK, UB, or HIV LTR promoter.

12. An isolated host cell comprising
(a) the vector of claim 1.

13. The cell of claim 12, which is an activated T cell.

14. A composition comprising (i) the adenoviral vector of claim 1 and (ii) a pharmaceutically acceptable carrier.

15. A method of transducing T cells comprising contacting the T cells with
(a) the vector of claim 1,
thereby transducing T cells with the vector.

16. The method of claim 15, wherein the T cells are activated prior to contacting the T cells with the vector.

17. The method of claim 16, wherein the T cells are activated by contacting the T cells with anti-CD3 antibodies and a costimulatory molecule.

18. The method of claim 17, wherein the costimulatory molecule is CD28, CD137/4-1BB, CD40, CD40L, ICOS, OX40, CD2, LFA1, galectin 9, GITR, or a combination thereof.

19. The method of claim 16, wherein the activated T cells are cultured in serum-free medium prior to contact with the vector.

20. The method of claim 19, wherein the serum-free medium comprises a IL-2, IL-7, IL-12, IL-15, IL-21, or a combination thereof.

21. The method of claim 15, wherein the T cells are from a patient with cancer.

22. The method of claim 15, wherein the T cells are contacted with the vector 1-15 days after the T cells are activated.

23. The vector of claim 1, wherein the exogenous nucleic acid sequence encodes single chain variable anti-MUC1.

24. The vector of claim 1, wherein the exogenous nucleic acid sequence encodes single chain variable anti-CD19.

25. The vector of claim 1, wherein the exogenous nucleic acid sequence encodes single chain variable anti-ROR1.

26. The vector of claim 1, wherein the exogenous nucleic acid sequence encodes single chain variable anti-mesothelin.

27. The vector of claim 1, wherein the exogenous nucleic acid sequence encodes single chain variable anti-CD2.

28. The vector of claim 1, wherein the exogenous nucleic acid sequence encodes single chain variable anti-CD123.

29. The vector of claim 1, wherein the exogenous nucleic acid sequence encodes single chain variable anti-MUC16.

30. The vector of claim 1, wherein the exogenous nucleic acid sequence encodes single chain variable anti-Her2/Neu.

31. The vector of claim 1, wherein the exogenous nucleic acid sequence encodes single chain variable anti-L1CAM.

32. The vector of claim 1, wherein the exogenous nucleic acid sequence encodes single chain variable anti-BCMA.

33. The vector of claim 1, wherein the exogenous nucleic acid sequence encodes a γδ T cell receptor (TCR).

\* \* \* \* \*